US012674795B2

(12) United States Patent
Wong et al.

(10) Patent No.: US 12,674,795 B2
(45) Date of Patent: Jul. 7, 2026

(54) METHOD FOR PERITONEAL METASTATIC CELL DETECTION AND ISOLATION THEREOF

(71) Applicant: THE UNIVERSITY OF HONG KONG, Hong Kong (CN)

(72) Inventors: Sze Tsai Alice Wong, Hong Kong (CN); Ho Cheung Anderson Shum, Hong Kong (CN); Shanshan Li, Shenzhen (CN); Ka Man Ip, Hong Kong (CN); Kei Shuen Tang, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 1287 days.

(21) Appl. No.: 17/607,669

(22) PCT Filed: Apr. 24, 2020

(86) PCT No.: PCT/CN2020/086655
§ 371 (c)(1),
(2) Date: Oct. 29, 2021

(87) PCT Pub. No.: WO2020/224450
PCT Pub. Date: Nov. 12, 2020

(65) Prior Publication Data
US 2022/0221444 A1 Jul. 14, 2022

Related U.S. Application Data

(60) Provisional application No. 62/842,689, filed on May 3, 2019.

(51) Int. Cl.
| | | |
|---|---|---|
| *G01N 33/57545* | (2026.01) |
| *G01N 33/50* | (2006.01) |
| *G01N 33/5753* | (2026.01) |
| *G01N 33/57535* | (2026.01) |
| *G01N 33/5755* | (2026.01) |
| *G01N 33/57555* | (2026.01) |

(52) U.S. Cl.
CPC ..... *G01N 33/5011* (2013.01); *G01N 33/5753* (2026.01); *G01N 33/57535* (2026.01); *G01N 33/57545* (2026.01); *G01N 33/5755* (2026.01); *G01N 33/57555* (2026.01)

(58) Field of Classification Search
None
See application file for complete search history.

(56) References Cited

FOREIGN PATENT DOCUMENTS

CN 101443660 A 5/2009

OTHER PUBLICATIONS

Edwards et al.(Oncotarget 8:83585-601) (Year: 2017).*
Carroll et al (Cancer Research 78(13) pp. 3560-3572) (Year: 2018).*
(Continued)

*Primary Examiner* — Christopher M Gross

(57) ABSTRACT

Provided herein is a method for the detection and isolation of metastatic cells from a sample obtained from a subject. Also provided is a device comprising a microchip for use in the method. Also provided is a method of isolating the metastatic cells for culture and characterization. Provided herein is a kit for the method therein.

13 Claims, 52 Drawing Sheets

(56)                References Cited

OTHER PUBLICATIONS

Shan-Shan Li et al., Abstract 5885: Sialyl Lewis X-P-selectin connection between ovarian tumor-mesothelium in early stage metastasis, Cancer Research, Jul. 1, 2017, 5885-5885, vol. 77, No. 13_Supplement, American Association for Cancer Research.
Li SS et al., "Sialyl Lewisx-P-selectin cascade mediates tumor-mesothelial adhesion in ascitic fluid shear flow", Nature Communications, vol. 10, No. 1, Jun. 3, 2019 (Jun. 3, 2019).
Gebauer F. et al., "Selectin binding is essential for peritoneal carcinomatosis in a xenograft model of human pancreatic adenocarcinoma in pfp-/rag2-mice", GUT, vol. 62, No. 5, Jul. 26, 2012 (Jul. 26, 2012), pp. 741-750 see p. 748, paragraph 3, p. 749, discussion.
Wicklein D. et al., "E- and P-selectin are essential for peritoneal carcinomatosis in a xenograft model of human pancreatic adenocarcinoma", Oncology Research and Treatment, vol. 37, No. Supplement 1, Feb. 22, 2014 (Feb. 22, 2014).
Schröder C. et al., "E- and P-selectin determine peritoneal spread of ovarian cancer in a xenograft model", Oncology Research and Treatment, vol. 37, No. Supplement 1, Feb. 22, 2014 (Feb. 22, 2014).
Edwards EE et al., "P- but not E- or L-selectin-mediated rolling adhesion persistence in hemodynamic flow diverges between metastatic and leukocytic cells", Oncotarget, vol. 8, No. 48, Jun. 28, 2017 (Jun. 28, 2017).
Bose S. et al., "Microfluidic patterning of P-selectin for cell separation through rolling", 15th International Conference on Miniaturized Systems for Chemistry and Life Sciences, Seattle, Washington, USA, Oct. 16, 2008 (Oct. 16, 2008).
Bose S. et al., "Microfluidic devices for rapid label-free separation of cells", 15th International Conference on Miniaturized Systems for Chemistry and Life Sciences, Seattle, Washington, USA, Oct. 6, 2011 (Oct. 6, 2011).
Siegel, R. L., Miller, K. D. & Jemal, A. Cancer Statistics, 2019. CA: Cancer J Clin 69, 7-34 (2019).
Lengyel, E. Ovarian cancer development and metastasis. Am J Pathol 177, 1053-1064 (2010).
Massague, J. & Obenauf, A. C. Metastatic colonization by circulating tumour cells. Nature 529, 298-306 (2016).
Kipps, E., Tan, D. S. & Kaye, S. B. Meeting the challenge of ascites in ovarian cancer: new avenues for therapy and research. Nat Rev Cancer 13, 273-282 (2013).
McEver, R. P. & Zhu, C. Rolling cell adhesion. Ann Rev Cell Dev Biol 26, 363-396 (2010).
Laubli, H. & Borsig, L. Selectins promote tumor metastasis. Semin Cancer Biol 20, 169-177 (2010).
Friederichs, J. et al. The CD24/P-selectin binding pathway initiates lung arrest of human A125 adenocarcinoma cells. Cancer Res 60, 6714-6722 (2000).
Dimitroff, C. J., Lechpammer, M., Long-Woodward, D. & Kutok, J. L. Rolling human bone-metastatic prostate tumor cells on human bone marrow endothelium under shear flow is mediated by E-selectin. Cancer Res 64, 5261-5269 (2004).
Gebauer, F. et al. Selectin binding is essential for peritoenal carcinomatosis in a xenograft model of human pancreatic adenocarcinoma in pfp-/rag2-mice. Gut 62, 741-750 (2013).
Carroll, M. J. et al. Alternatively-activated macrophages upregulate mesothelial expression of P-selectin to enhance adhesion of ovarian cancer cells. Cancer Res 78, 3560-3573 (2018).
Nagy, J. A., Herzberg, K. T., Dvorak, J. M. & Dvorak, H. F. Pathogenesis of malignant ascites formation: initiating events that lead to fluid accumulation. Cancer Res 53, 2631-2643 (1993).
Chau, W. K., Ip, C. K., Mak, A. S., Lai, H. C. & Wong, A. S. c-Kit mediates chemoresistance and tumor-initiating capacity of ovarian cancer cells through activation of Wnt/beta-catenin-ATP-binding cassette G2 signaling. Oncogene 32, 2767-2781 (2013).
Ip, C. K. et al. Stemness and chemoresistance in epithelial ovarian carcinoma cells under shear stress. Sci Rep 6, 26788 (2016).

Nagy, J. A. et al. Pathogenesis of ascites tumor growth: vascular permeability factor, vascular hyperpermeability, and ascites fluid accumulation. Cancer Res 55, 360-368 (1995).
Lawrence, M. B., Kansas, G. S., Kunkel, E. J. & Ley, K. Threshold levels of fluid shear promote leukocyte adhesion through selectins (CD62L,P,E). J Cell Biol 136, 717-727 (1997).
Yanez-Mo, M. et al. Peritoneal dialysis and epithelial-to-mesenchymal transition of mesothelial cells. N Engl J Med 348, 403-413 (2003).
Varki, A. Selectin ligands. Proc Natl Acad Sci USA 91, 7390-7397 (1994).
Steele, I. A. et al. Induction of FGF receptor 2-IIIb expression and response to its ligands in epithelial ovarian cancer. Oncogene 20, 5878-5887 (2001).
Brokaw, J. et al. IGF-I in epithelial ovarian cancer and its role in disease progression. Growth Factors 25, 346-354 (2007).
Sawada, K. et al. c-Met overexpression is a prognostic factor in ovarian cancer and an effective target for inhibition of peritoneal dissemination and invasion. Cancer Res 67, 1670-1679 (2007).
Ellerbroek, S. M. et al. Phosphatidylinositol 3-kinase activity in epidermal growth factor-stimulated matrix metalloproteinase-9 production and cell surface association. Cancer Res 61, 1855-1861 (2001).
De Vries, T., Knegtel, R. M., Holmes, E. H. & Macher, B. A. Fucosyltransferases: structure/function studies. Glycobiology 11, 119R-128R (2001).
Lofling, J. & Holgersson, J. Core saccharide dependence of sialyl Lewis X biosynthesis. Glycoconj J 26, 33-40 (2009).
Yin, G. et al. Constitutive proteasomal degradation of TWIST-1 in epithelial-ovarian cancer stem cells impacts differentiation and metastatic potential. Oncogene 32, 39-49 (2013).
Zhang, S. et al. Identification and characterization of ovarian cancer-initiating cells from primary human tumors. Cancer Res 68, 4311-4320 (2008).
Vathipadiekal, V. et al. Identification of a potential ovarian cancer stem cell gene expression profile from advanced stage papillary serous ovarian cancer. PloS One 7, e29079 (2012).
Baccelli, I. et al. Identification of a population of blood circulating tumor cells from breast cancer patients that initiates metastasis in a xenograft assay. Nat Biotechnol 31, 539-544 (2013).
Dieter, S. M. et al. Distinct types of tumor-initiating cells form human colon cancer tumors and metastases. Cell Stem Cell 9, 357-365 (2011).
Pang, R. et al. A subpopulation of CD26+ cancer stem cells with metastatic capacity in human colorectal cancer. Cell Stem Cell 6, 603-615 (2010).
Elmasri, V. M., Casagrande, G., Hoskins, E., Kimm, D. & Kohn, E. C. Cell adhesion in ovarian cancer. Cancer Treat Res 149, 297-318 (2009).
Inoue, M., Fujita, M., Nakazawa, A., Ogawa, H. & Tanizawa, O. Sialyl-Tn, sialyl-Lewis Xi, CA 19-9, CA 125, carcinoembryonic antigen, and tissue polypeptide antigen in differentiating ovarian cancer from benign tumors. Obstet Gynecol 79, 434-440 (1992).
Escrevente, C. et al. Different expression levels of alpha3/4 fucosyltransferases and Lewis determinants in ovarian carcinoma tissues and cell lines. Int J Oncol 29, 557-566 (2006).
Wang, P. H. et al. Altered mRNA expressions of sialyltransferases in ovarian cancers. Gynecol Oncol 99, 631-639 (2005).
Saldova, R. et al. Ovarian cancer is associated with changes in glycosylation in both acute-phase proteins and IgG. Glycobiology 17, 1344-1356 (2007).
Zhou, Q. et al. The selectin GMP-140 binds to sialylated, fucosylated lactosaminoglycans on both myeloid and honmyeloid cells. J Cell Biol 115, 557-564 (1991).
Toppila, S. et al. Enzymatic synthesis of alpha3'sialylated and multiply alpha3fucosylated biantennary bolylactosamines. A bivalent [sialyl diLex]-saccharide inhibited lymphocyte-endothelium adhesion organ-selectively. Eur J Biochem 261, 208-215 (1999).
Phillips, M. L. et al. ELAM-1 mediates cell adhesion by recognition of a carbohydrate ligand, sialyl-Lex. Science 250, 1130-1132 (1990).
Listinsky, J. J., Siegal, G. P. & Listinsky, C. M. Alpha-L-fucose: a potentially critical molecule in pathologic processes Including neoplasia. Am J Clin Pathol 110, 425-440 (1998).

(56) References Cited

OTHER PUBLICATIONS

Aruffo, A. et al. CD62/P-selectin recognition of myeloid and tumor cell sulfatides. Cell 67, 35-44 (1991).

Sako, D. et al. A sulfated peptide segment at the amino terminus of PSGL-1 is critical for P-selectin binding. Cell 83, 323-331 (1995).

Rodgers, S. D., Camphausen, R. T. & Hammer, D. A. Tyrosine sulfation enhances but is not required for PSGL-1 rolling adhesion on P-selectin. Biophys J 81, 2001-2009 (2001).

Spentzos, D. et al. IGF axis gene expression patterns are prognostic of survival in epithelial ovarian cancer. Endocr Relat Cancer 14, 781-790 (2007).

Takahari, D. et al. Relationships of insulin-like growth factor-1 receptor and epidermal growth factor receptor expression to clinical outcomes in patients with colorectal cancer. Oncology 76, 42-48 (2009).

Varki A, Kannagi R, Toole BP. Glycosylation Changes in Cancer. In: Varki A, Cummings RD, Esko JD, et al., editors. Essentials of Glycobiology. 2nd edition. Cold Spring Harbor (NY): Cold Spring Harbor Laboratory Press; 2009. Chapter 44.

Gomes, C. et al. Expression of ST3GAL4 leads to SLe(x) expression and induces c-Met activation and an invasive phenotype in gastric carcinoma cells. PloS One 8, e66737 (2013).

Padro, M., Cobler, L., Garrido, M. & de Bolos, C. Down-regulation of FUT3 and FUT5 by shRNA alters Lewis antigens expression and reduces the adhesion capacities of gastric cancer cells. Biochim Biophys Acta 1810, 1141-1149 (2011).

Yung, S., Li, F. K. & Chan, T. M. Peritoneal mesothelial cell culture and biology. Perit Dial Int 26, 162-173 (2006). 55. Gokturk, H. S. et al. The role of ascitic fluid viscosity in the differential diagnosis of ascites. Can J Gastroenterol 24, 255-259 (2010).

Gokturk, H. S. et al. The role of ascitic fluid viscosity in the differential diagnosis of ascites. Can J Gastroenterol 24, 255-259 (2010).

Chen, S., Alon, R., Fuhlbrigge, R. C. & Springer, T. A. Rolling and transient tethering of leukocytes on antibodies reveal specializations of selectins. Proc Natl Acad Sci USA 94, 3172-3177 (1997).

Gyorffy, B., Lanczky, A. & Szallasi, Z. Implementing an online tool for genome-wide validation of survival-associated biomarkers in ovarian-cancer using microarray data from 1287 patients. Endocr Relat Cancer 19, 197-208 (2012).

* cited by examiner i.p. injection
Selp$^{WT}$
Selp$^{-/-}$

Orthotopic injection
Selp$^{WT}$
Selp$^{-/-}$

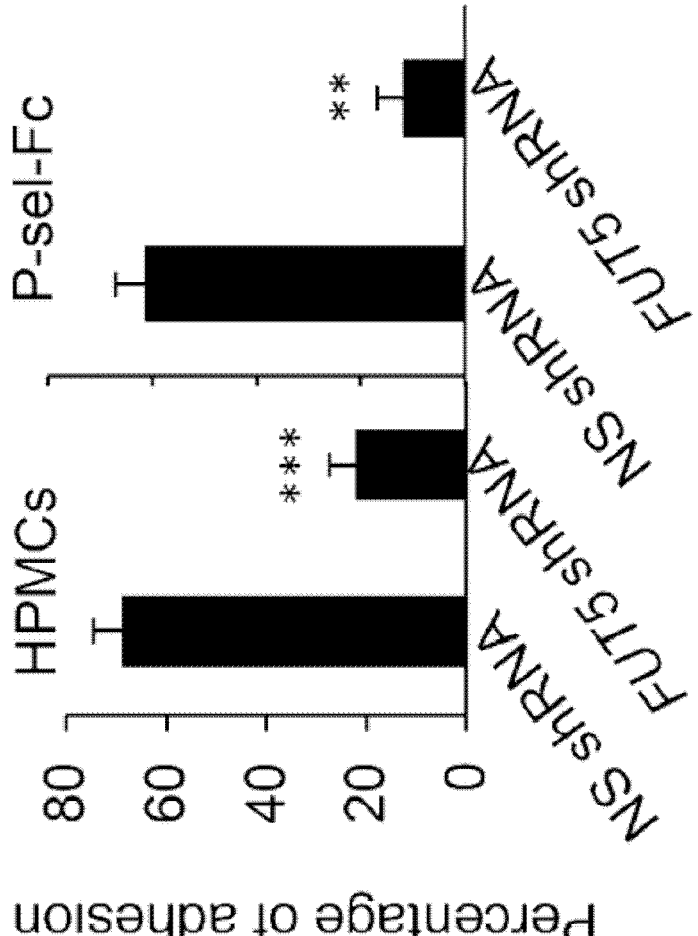
FIG. 6C
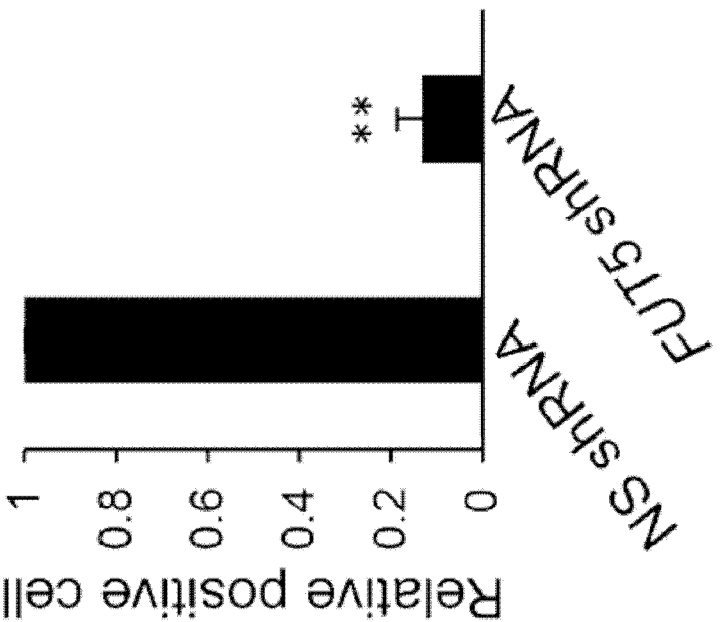

Channel height: 250 µm 4.0 mm

Inlet

Outlet 2.2mm 25.0 mm

127°

$$\tau = \frac{6Q\mu}{h^2 w}$$

$\tau$ – Shear stress (dyne/cm$^2$)

$Q$ – Flow rate (ml/sec)

$\mu$ – viscosity (g/cm·sec)

$h$ – Height of channel (cm)

$w$ – Width of channel (cm)

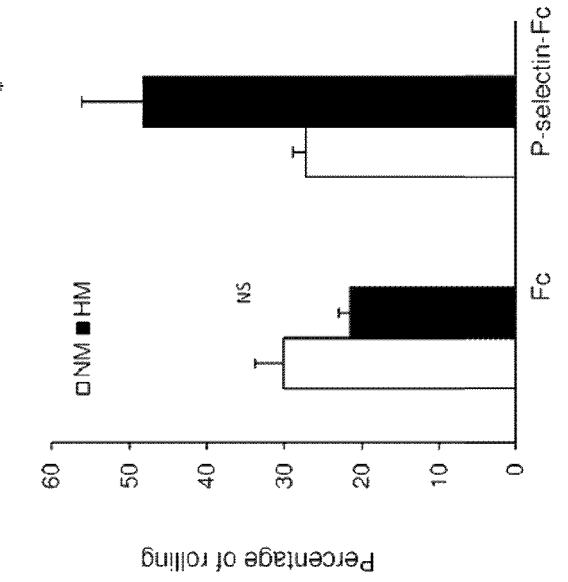
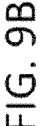
FIG. 9B
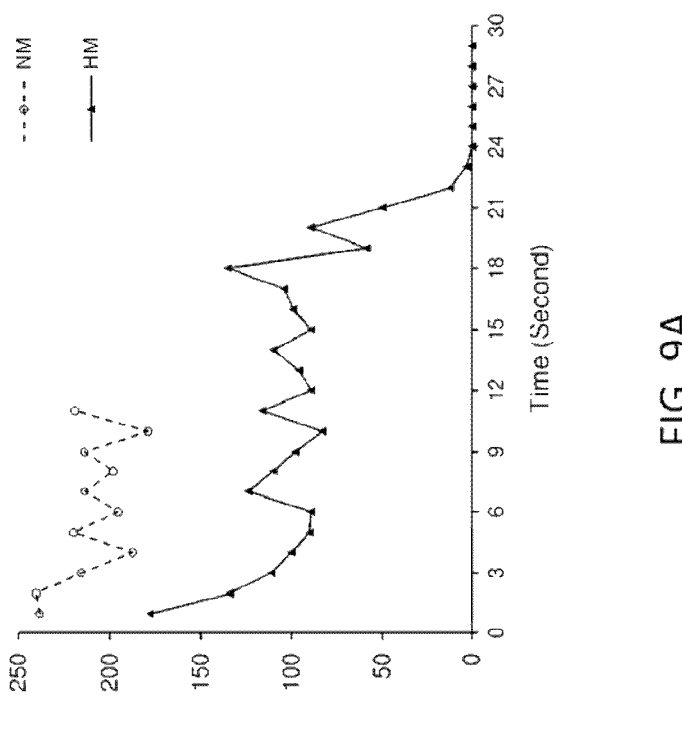
FIG. 9A

| | Fc | P-selectin-Fc |
|---|---|---|
| A78 (Pleural fluid, lung cancer) | 0.02 | 18.87 |
| A81 (Ascites, colon cancer) | 0 | 81.39 |
| A82 (Ascites, breast cancer) | 0 | 15.17 |
| A17 (Ascites, ovarian cancer) | 0 | 50.57 |
| A42 (Ascites, ovarian cancer) | 0 | 30.00 |
| A80 (Ascites, ovarian cancer) | 0 | 45.45 |

FIG. 11

Antibodies and recombinant proteins

| Antibody | Catalog no., source | Concentration |
|---|---|---|
| Anti-β-actin | A5060, Sigma-Aldrich | 1:5000 |
| Anti-CA19-9 | ab15146, Abcam | 1:100 |
| HECA-452 | 550407, BD Biosciences | FC:10 µg mL$^{-1}$, WB:1:50 |
| CSLEX-1 | 551344, BD Biosciences | 10 µg mL$^{-1}$ |
| Anti-IGF-1R β | 3027, Cell Signaling | 1:1000 |
| Anti-IGF-1R α (N-20) | SC-712, Santa Cruz Biotechnology | 1:1000 |
| Anti-phospho-IGF-1R β | 3024s, Cell Signaling | 1:1000 |
| Anti-E-selectin | 555648, BD Biosciences | 20 µg mL$^{-1}$ |
| Anti-L-selectin | 555522, BD Biosciences | 20 µg mL$^{-1}$ |
| Anti-P-selectin | 555542, BD Biosciences | 20 µg mL$^{-1}$ |
| Alexa Fluor 488 goat anti-rat IgM | A-21212, Life technology | 1:500 |
| Alexa Fluor 488 goat anti-mouse IgG, IgM | A-10667, Life technology | 1:500 |
| Alexa Fluor 488 goat anti-human IgG | A-11013, Life technology | 1:500 |
| Mouse IgG | I5381, Sigma-Aldrich | Same as target antibodies |
| Mouse IgM | 555581, BD Biosciences | Same as target antibodies |
| Goat anti-Rat IgM Secondary Antibody, HRP | 31476, Invitrogen | 1:100000 |
| Goat anti-mouse IgG (H+L)-HRP conjugated | 170-6516, Bio-Rad | 1:3000 |
| Goat anti-rabbit IgG (H+L)-HRP conjugated | 170-6515, Bio-Rad | 1:2500 |

Recombinant proteins

| Recombinant protein | Catalog no., source | Working concentration |
|---|---|---|
| Recombinant Human E-Selectin Fc Chimera | 724-ES, R&D systems | 1~5 µg mL$^{-1}$ |
| Recombinant Human P-Selectin Fc Chimera | 137-PS, R&D systems | 1~5 µg mL$^{-1}$ |
| Recombinant Human L-Selectin Fc Chimera | 728-LS, R&D systems | 1~5 µg mL$^{-1}$ |
| Recombinant Human IgG1 Fc | 110-HG, R&D systems | Same as selectin-Fc |
| Human Fibronectin | 354008, Corning | 10 µg mL$^{-1}$ |

FIG. 12

Biochemical inhibitors

| Inhibitor | Description | Catalog no., source | Concentration |
|---|---|---|---|
| Genistein | Protein tyrosine kinase inhibitor | 345834, Calbiochem | 50 μM |
| AG1024 | IGF-1R inhibitor | 121767, Calbiochem | 10 μM |
| AG1478 | EGFR inhibitor | 65855, Calbiochem | 200 nM |
| K252a | Met inhibitor | 420298, Calbiochem | 50 nM |
| SU5402 | FGF-1R inhibitor | 572630, Calbiochem | 50 μM |

FIG. 13

DNA primers

| Gene | Forward 5' – 3' | Reverse 5' – 3' |
|---|---|---|
| Primers for quantitative real-time PCR: | | |
| *E-selectin* | CAGCAAAGGTACACACACCTG | CAGACCCACACATTGTTGACTT |
| *P-selectin* | TCCTCACAGCCACCTAGGAA | GGAAACAGGGTTGGTCCAGA |
| *L-selectin* | TCTGTTACACAGCTTCTTGCCA | GGCCCATAGTACCCCACATC |
| *B4GalT4* | GTGGGCCACCAGTAACTACTT | TCGTGGATGCTTCATTAGTCAGA |
| *ST3Gal3* | GCCTGCTGAATTAGCCACCAA | GCCCACTTGCGAAAGGAGT |
| *ST3Gal4* | CCACTTCGACCCCAAAGTAGA | CGCACCCGCTTCTTATCACT |
| *FUT5* | GAGGGCGAAGGGTATGTGTG | GCATCGCAACACATCCACAG |
| *GAPDH* | GGAGCGAGATCCCTCCAAAAT | GGCTGTTGTCATACTTCTCATGG |
| *CD24* | CTCCTACCCACGCAGATTTATTC | AGAGTGAGACCACGAAGAGAC |
| *IGF-1R* | TGTCCAGGCCAAAACAGGA | CAACCCTCCCACGATCAACA |
| *N-cadherin* | AATCGTGTCTCAGGCTCCAA | TGGGATTGCCTTCCATGTCT |
| *Vimentin* | CCCTCACCTGTGAAGTGGAT | TGACGAGCCATTTCCTCCTT |

| Gene | Forward 5' – 3' | Reverse 5' – 3' |
|---|---|---|
| Primers for genotyping: | | |
| *Selp*[WT] | TTGTAAATCAGAAGGAAGTGG | AGAGTTACTCTTGATGTAGATCTCC |
| *Selp*[Mutant] | CTGAATGAACTGCAGGACGA | ATACTTTCTCGGCAGGAGCA |
| *Rag2*[WT] | ATCAATGGTTCACCCCTTTG | TCATGTGAAAGCAGTTCAGGAC |
| *Rag2*[Mutant] | CCGCCATATGCATCCAAC | CAGCGCTCCTCCTGATACTC |

| Gene target | Sequence 5' – 3' |
|---|---|
| shRNA for knockdown: | |
| *FUT5* | CCGGCACTGCCGACTCCAGTGTGTACTCGAGTACACACTGGAGTCGGCAGTGTTTTTG |

FIG. 14

Supplementary Table 4 Metastasis in $Selp^{WT}$ and $Selp^{-/-}$ mice

|  | $Selp^{WT}$ | $Selp^{-/-}$ |
|---|---|---|
| Metastases (no.) | $45 \pm 6$ | $11 \pm 2$ (orthotopic) * |
|  | $103 \pm 6$ | $47 \pm 3$ (i.p.) ** |
| Ascites volume (mL) | $0.5 \pm 0.06$ | $0.1 \pm 0.02$ (orthotopic) ** |
|  | $0.6 \pm 0.07$ | $0.2 \pm 0.02$ (i.p.) * |

Results are represented with mean $\pm$ SEM. n = 6 mice (orthotopic) or 9 mice (i.p.) from two independent experiments. Statistical analysis using unpaired Student's $t$ test. ns, not significant. *, $P < 0.05$; **, $P < 0.01$.

FIG. 15

Supplementary Table 5 Metastasis in mice with NS or FUT5 shRNA transduced M-CSCs

|  | NS shRNA | FUT5 shRNA |
|---|---|---|
| Metastases (no.) | 24 ± 6 | 4 ± 3 (orthotopic) * |
| | 40 ± 9 | 13 ± 5 (i.p.) * |
| Ascites volume (mL) | 0.9 ± 0.26 | 0.1 ± 0.07 (orthotopic) * |
| | 0.6 ± 0.02 | 0.2 ± 0.07 (i.p.) * |

Results are represented with mean ± SEM. n = 3 mice (orthotopic) or 6 mice (i.p.) from two independent experiments. Statistical analysis using unpaired Student's $t$ test. ns, not significant. *, $P <$ 0.05.

FIG. 16

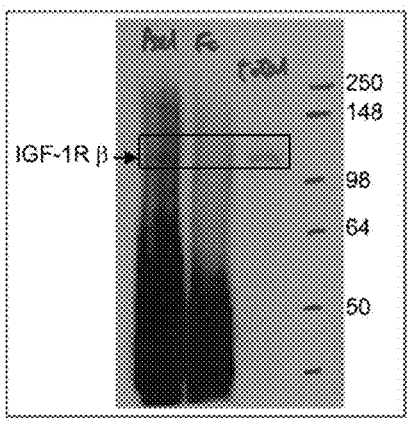
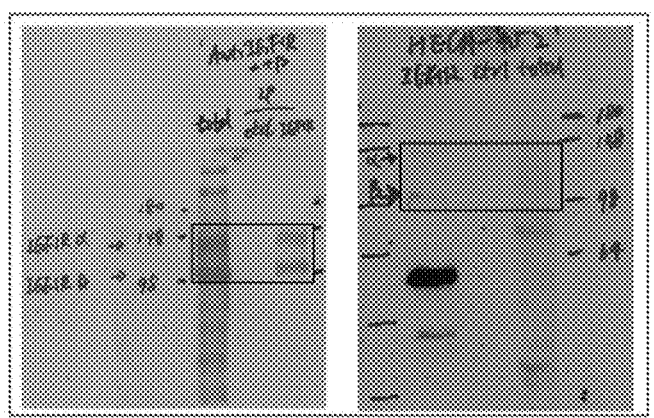
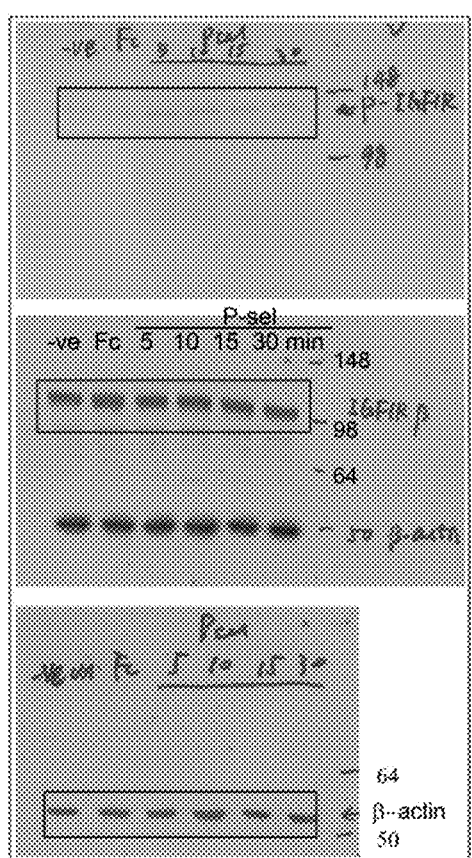
FIG. 25

(a)
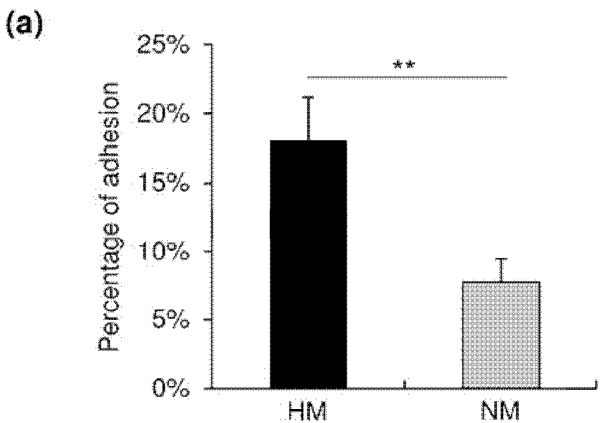
Metastatic potential: HM > NM
Reference: in vivo experiment
(b)
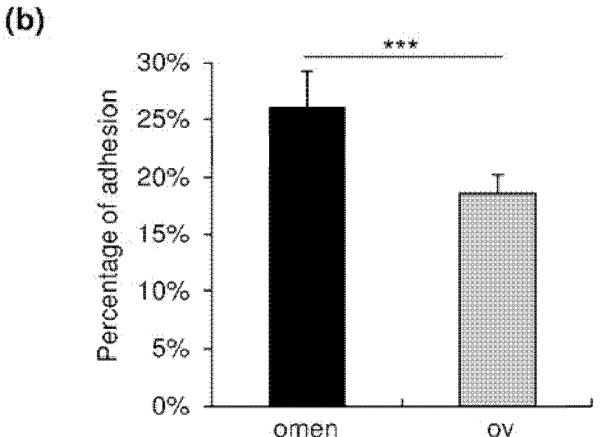
Metastatic potential: omen > ov
Reference: in vivo experiment
(c)
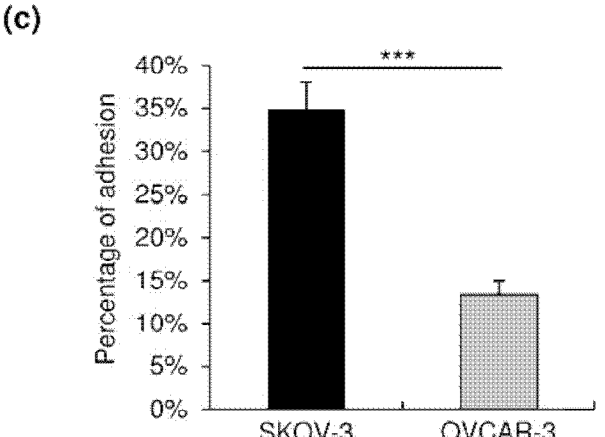
Metastatic potential: SKOV-3 > OVCAR-3
Reference: Journal of Cell Science (2014) 127, 2621–2626 doi:10.1242/jcs.144378
FIG. 27

(a)
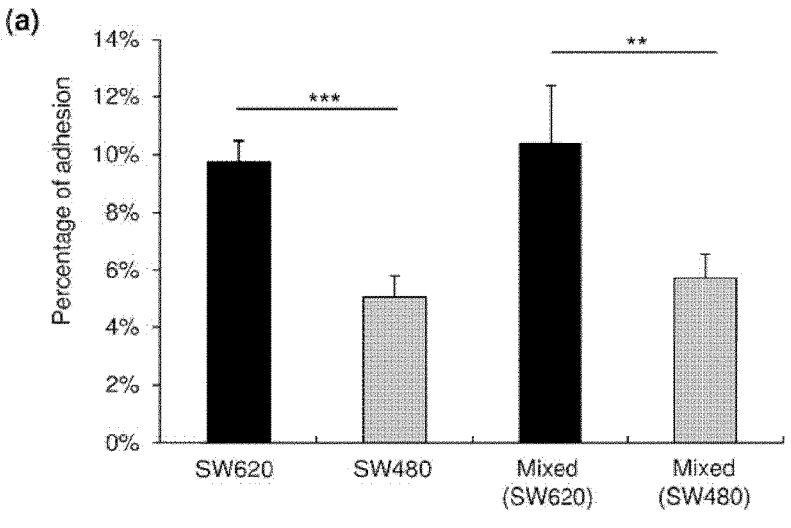
Metastatic potential: SW620 > SW480
Reference: Anticancer Res. 2018 Nov;38(11):6133-6138. doi: 10.21873/anticanres.12965.
(b)
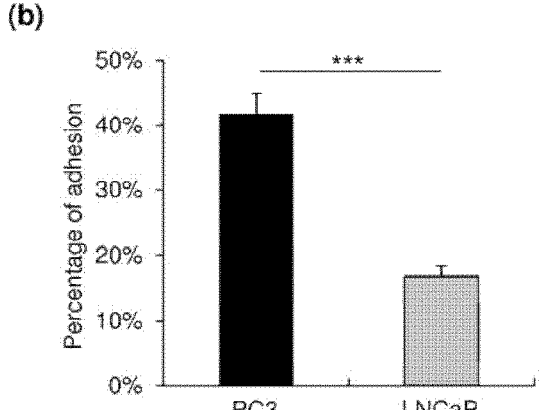
Metastatic potential: PC3 > LNCaP
Reference: Gene. 2001 Nov 14;279(1):17-31.
(c)
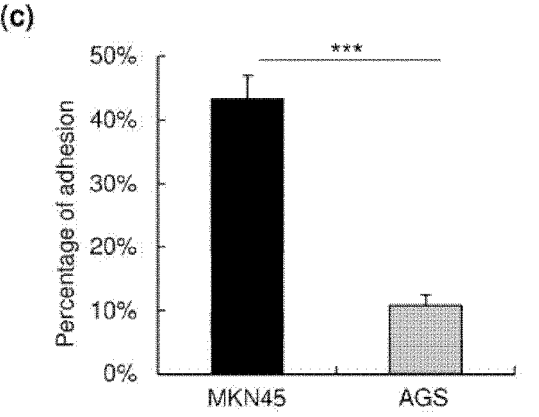
Metastatic potential: MKN45 > AGS
Reference: Sci Rep. 2018 Jan 16;8(1):825. doi: 10.1038/s41598-017-19025-y.
FIG. 28

(a)
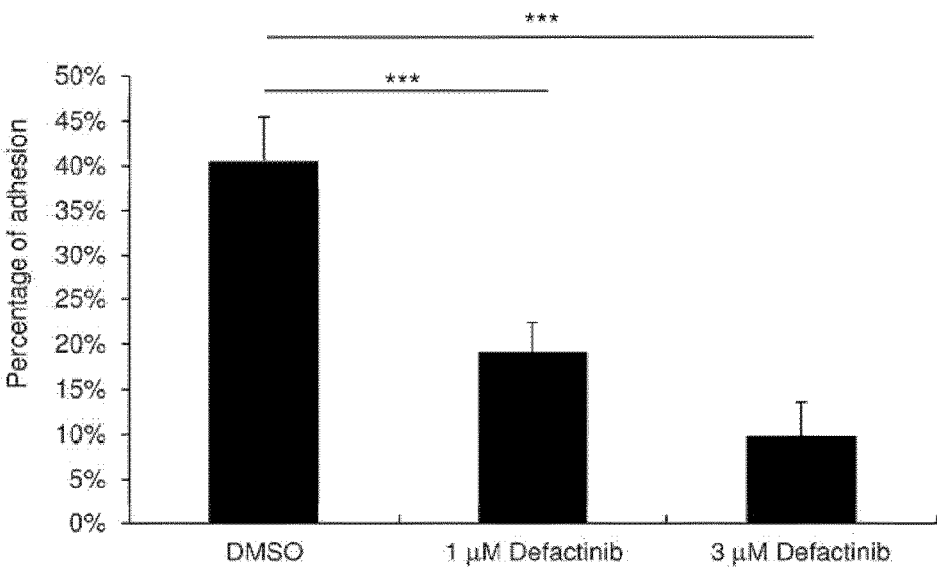
Defactinib: a focal adhesion kinase inhibitor
Clinical Trials: Phase I in ovarian cancer, Phase II in non-small cell lung cancer
(b)
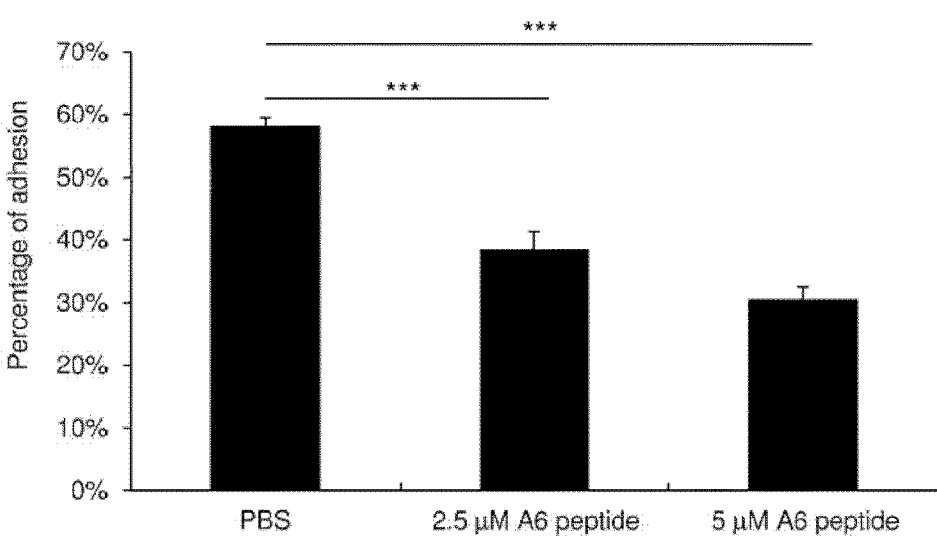
A6 peptide (Ac-KPSSPPEE-NH2): derived from the biologically active connecting peptide domain of human urokinase plasminogen activator, block CD44-mediated cascade
Clinical Trials: Phase II in ovarian cancer
FIG. 29

METHOD FOR PERITONEAL METASTATIC CELL DETECTION AND ISOLATION THEREOF

CROSS-REFERENCE TO RELATED PATENT APPLICATIONS

This application is a U.S. National Stage Application under 35 U.S.C. § 371 of International Patent Application No. PCT/CN2020/086655 filed Apr. 24, 2020, which claims the benefit of priority of U.S. Patent Application No. 62/842,689 filed May 3, 2019, both of which are incorporated by reference in their entireties. The International Application was published on Nov. 12, 2020, as International Publication No. WO/2020/224450A1.

The present application claims priority to U.S. provisional application Ser. No. 62/842,689, filed May 3, 2019 which is incorporated by reference in its entirety.

1. FIELD

Provided herein is a method for the detection and isolation of metastatic cells from a sample obtained from a subject. Also provided is a device comprising a microchip for use in the method. Also provided is a method of isolating the metastatic cells for culture and characterization. Provided herein is a kit for the method therein.

2. BACKGROUND

Peritoneal metastasis originating from gastrointestinal and gynecological malignancies are associated with poor prognosis and rapid disease progression. It is one of the leading causes of gastrointestinal and gynecological cancer-related mortality with the mean survival period estimated to be less than several months. The poor prognosis is principally due to a lack of effective methods to detect disseminated tumors at the earliest stage when tumor cells are few and tiny. Assessment of early peritoneal dissemination is beneficial to prolong survival. However, current strategies for the detection of peritoneal metastasis are limited to invasive pathological analysis and imaging approaches with low sensitivity and specificity. Furthermore, the ability to detect, isolate, propagate, and molecularly characterize peritoneal metastasis cells will be of great value for clinical practice and basic medical research. It is still challenging to identify peritoneal metastasis subpopulations from mixed cells of disease suspected tissues due to the lack of metastasis-specific biomarker.

The disease is often discovered with the accumulation of ascites, occurring generally with significant tumor burden which is more difficult to treat. Current strategies for the detection of peritoneal metastasis are limited to invasive pathological analysis and imaging approaches with low sensitivity and specificity. Furthermore, the ability to detect, isolate, propagate, and molecularly characterize peritoneal metastasis subpopulations could further the discovery of metastasis-related biomarkers and advance the knowledge of metastasis biology. This is also important to avoid the current problems of over-diagnosis and over-treatment of indolent cancer and under-treatment of aggressive cancer. However, the method to capture and isolate of peritoneal metastatic subpopulations is still lacking.

Peritoneal metastasis is difficult to diagnose in the early stages of the disease via clinical and instrumental techniques. It can be entirely asymptomatic in its early stages, symptoms show with the development of significant tumor burden. Tumor cells obtained via biopsy or surgical procedures can be used for histological analysis to collect pathological features. However, the invasive and risky sample collection procedure makes serial biopsies unfeasible. Furthermore, the diagnosis greatly on physicians, which may have inter-physician variability.

Imaging

Despite significant advancement of imaging technologies, ultrasound, CT scan, magnetic resonance imaging (MRI), positron emission tomography (PET) imaging, assessment of the peritoneal metastasis is still challenging. Because of the complexity of peritoneal anatomy and the overlap of imaging features, these imaging approaches have limited sensitivity and accuracy in detecting small peritoneal implants and evaluation of the extent of the disease. Moreover, high cost of imaging equipment and the requirement of clinical radiologists have limited the application.

Liquid Biopsy

Liquid biopsy is a minimal invasive technique to detect of molecular biomarkers in blood, which has the potential for real-time evaluation of the tumor progression, response to therapy, presence of minimal residual disease. Liquid biopsy markers including circulating tumor cells (CTCs), circulating tumor DNA (ctDNA) and extracellular vesicles (EVs). Most liquid biopsy techniques focus on blood-borne metastasis, few studies have addressed its application in the early detection of peritoneal metastasis. Although considerable effort has been made to identify novel biomarkers, relatively few identified candidates have been subjected to rigorous validation.

While multiple serum tumor markers: carcinoembryonic antigen (CEA), alpha fetoprotein (AFP), carbohydrate antigen CA 19-9, and CA 125, are elevated in most patients with peritoneal metastasis, it is not specific to distinguish between localized or diffuse peritoneal disease and indicate the risk of peritoneal metastasis.

Various techniques have been developed for the identification and enrichment of CTCs which have been recognized as the origin of metastatic disease. CTCs are rare in blood of patients with blood-borne metastatic disease, and even lower concentrations of CTCs present in patients with peritoneal metastasis. For instance, CTCs are less likely present in patients with colorectal cancer compared with those with breast and prostate cancer, even rare in ovarian and pancreatic cancers. Thus, few studies have addressed its application in peritoneal metastasis till now.

3. SUMMARY

The present disclosure relates to a method for diagnosing peritoneal cancer or metastatic primary tumors in a subject, as well as to a method for providing a prognosis to a subject diagnosed with a primary tumor to develop metastases, in particular peritoneal cancer, comprising the step of determining the binding of a peritoneal cells to P-selectin or E-selectin. Further, the disclosure relates to a diagnostic kit, comprising at least one substance for detection of the binding of peritoneal cells to P-selectin, either alone or in combination with E-selectin for the diagnosis or prognosis of peritoneal cancer and/or metastatic primary tumors.

A method for the detection and isolation peritoneal metastasis cells is disclosed herein. The method comprises introducing the tumor cell sample into the inlet of the microfluidic device wherein channel bottom coated with P-selectin recombinant protein, flowing the sample at desired wall shear stresses, and separating the peritoneal metastatic cells from the other cells in the sample as the peritoneal metastatic cells are captured by P-selectin under flow condition.

The present method serves as a peritoneal metastasis risk prediction platform which can be used in early metastasis detection. This method also enables the isolation of metastatic subpopulations, thus can be widely used in studies related to peritoneal metastasis and, particularly, is suitable for studies related to anti-metastasis effects on cancer cells.

The inventors discovered the differential binding capability of peritoneal metastatic cells and non-metastatic cells on P-selectin under flow and as the first time identified P-selectin as a potential peritoneal metastasis-specific biomarker. The inventors further disclosed a method to identify and isolate peritoneal metastasis cells with a microfluidic chip.

P-selectin is a calcium-dependent carbohydrate-binding molecule that mediates transient heterotypic cell-cell interaction under hydrodynamic flow. The inventors identified P-selectin expressed on peritoneal mesothelium as the functional adhesion molecule mediating tumor cells attachment on the peritoneum and it is a peritoneal metastasis-specific biomarker that can be applied in the identification of peritoneal metastatic cells in disease suspicious samples. Disclosed herein is a method to detect and selectively captured peritoneal metastasis from disease suspected sample through a microfluidic system.

Also provided herein is additional biomarker coating (e.g. E-selectin) and flow condition to achieve more effective detection and isolation system. In certain embodiments, benign tumor cells are used as control and test the efficacy of this method using samples from various types of cancer.

Provided herein is a method for detecting peritoneal metastatic cells in a sample obtained from a subject comprising: (a) contacting peritoneal metastatic cells and peritoneal non-metastatic cells in the sample with P-selectin; and (b) detecting selective binding of the peritoneal metastatic cells to the P-selectin.

In certain embodiment, the peritoneal metastatic cells are from gastrointestinal cancer or gynecological cancer.

In certain embodiment, the gynecological cancer is ovarian cancer, uterine cancer, cervical cancer or vaginal cancer.

In certain embodiment, the gastrointestinal cancer is liver cancer, colon cancer, prostate cancer, bladder cancer and rectal cancer.

In certain embodiment, the method further comprising a step of isolating the peritoneal metastatic cells.

In certain embodiment, the method further comprising a step of culturing the peritoneal metastatic cells.

In certain embodiment, the method further comprises characterizing the peritoneal metastatic cells.

Provided herein is a method for detecting peritoneal metastatic cells in a sample obtained from a subject comprising: (a) introducing the sample into an inlet of a microfluidic device wherein the microfluidic device comprises a channel that is coated with P-selectin; (b) flowing the sample at an effective wall shear stresses; (c) separating the peritoneal metastatic cells from non-peritoneal metastatic cells, wherein the peritoneal metastatic cells binds to P-selectin; and (d) detecting the peritoneal metastatic cells.

In certain embodiment, the effective wall shear stresses is about 0.1 dyne/cm2.

In certain embodiment, the device is a microfluidic chip.

In certain embodiment, the peritoneal metastatic cells are detected by a label.

In certain embodiment, the peritoneal metastatic cells are from gastrointestinal cancer or gynecological cancer.

In certain embodiment, the gynecological cancer is ovarian cancer, uterine cancer, cervical cancer or vaginal cancer.

In certain embodiment, the gastrointestinal cancer is liver cancer, colon cancer, prostate cancer, bladder cancer and rectal cancer.

In certain embodiment, the method further comprising a step of isolating the peritoneal metastatic cells.

In certain embodiment, the method further comprising a step of culturing the peritoneal metastatic cells.

Provided herein is a device for separating peritoneal metastatic cells in a sample obtained from a subject comprising: (a) introducing the sample into an inlet of a microfluidic device wherein the microfluidic device comprises a channel that is coated with a detectable P-selectin; (b) separating the peritoneal metastatic cells from non-peritoneal metastatic cells in the sample by selective binding of the peritoneal metastatic cells to the detectable P-selectin.

In certain embodiment, the effective wall shear stresses is about 0.1 dyne/cm2.

In certain embodiment, the device is a microfluidic chip.

In certain embodiment, the peritoneal metastatic cells are detected by a label.

In certain embodiment, the peritoneal metastatic cells are from gastrointestinal cancer or gynecological cancer.

In certain embodiment, the gynecological cancer is ovarian cancer, uterine cancer, cervical cancer or vaginal cancer.

In certain embodiment, the gastrointestinal cancer is liver cancer, bladder cancer and rectal cancer.

In certain embodiment, the method further comprising a step of isolating the peritoneal metastatic cells.

In certain embodiment, the method further comprising a step of culturing the peritoneal metastatic cells.

Provided herein is a method of screening anti-metastatic drugs comprising: (a) contacting metastatic cells with a test agent; (b) selective binding of the treated metastatic cells to P-selectin; and (c) detecting metastatic cells contacted with the test agent that does not selectively bind to the P-selectin, wherein metastatic cells that does not bind to the P-selectin indicates that the cells were contacted with a test agent that has anti-metastatic property.

In certain embodiment, the peritoneal metastatic cells are detected by a label.

In certain embodiment, the peritoneal metastatic cells are from gastrointestinal cancer or gynecological cancer.

In certain embodiment, the gynecological cancer is ovarian cancer, uterine cancer, cervical cancer or vaginal cancer.

In certain embodiment, the gastrointestinal cancer is liver cancer, bladder cancer and rectal cancer.

In certain embodiment, the method further comprising a step of isolating the peritoneal metastatic cells.

In certain embodiment, the method further comprising a step of culturing the peritoneal metastatic cells.

Provided herein is a kit for detecting peritoneal metastatic cells in a sample obtained from a subject, said kit comprising a microfluidic chip and a detectable P-selectin.

4. DESCRIPTION OF THE FIGURES

FIG. 1A-1G Isolation and characterization of metastatic cancer stem cells. (A) Isolation of ovarian metastatic cancer stem cells. Blue circle, primary tumor. Red star, metastasis. (B, C) NOD/SCID mice engrafted with M-CSCs or NM-CSCs via (B) orthotopic or (C) i.p. injection. Left: representative bioluminescence image. Right: representative views of metastases in the peritoneal cavity. Arrows, metastases. Scale bar, 1 cm. n=5 (orthotopic) or 3 mice (i.p) per group. (D, E) Representative image (D) of and H&E staining (E) of primary tumors from mice orthotopically transplanted with M-CSCs or NM-CSCs. Arrows, tumors. Scale bars=1 cm (D) or 50 μm (E). (G) Representative view of metastasis in mice engrafted with M-CSCs of patient samples. Arrows, metastases. Scale bar, 1 cm. n=7 mice, samples collected from three patients. (H) Gene expression patterns of M-CSCs and NM-CSCS compared to metastatic (Met.) versus non-metastatic (Non-Met.) tumors from TCGA RNA-seq data of ovarian cancer patients. Left: heat map representing genes in M-CSC and NM-CSCs. Rows represent different genes and column represents each sample. Blue: downregulation; Red: upregulation. Right: Gene Set Enrichment Analysis of differentially up-regulated genes in M-CSCs samples against the ranked gene list (from up- to down-regulated) in TCGA metastatic ovarian tumors. X-axis from left to right: ordered genes from up- to down-regulation in TCGA metastatic tumors. Experiments were conducted two (a-f) or three (g, n=3 per group) times independently. Results are represented with mean±SEM. Statistical analysis using unpaired Student's t test ns, not significant. **, P<0.01.

FIG. 2A-2C Differential capabilities of M- and NM-CSCs in rolling adhesion on HPMCs. (A) Percentage of tethering of M-CSCs and NM-CSCs on HPMCs. (B) CSCs rolling velocities on HPMCs monolayers. Each dot represents individual cancer spheroid. Dash lines: median velocity of two cell lines. (C) Percentage of adhesion of M-CSCs and NM-CSCs on HPMCs under different shear stress. Results are representative of three independent experiments. Error bars indicate SEM of the mean. n=44/49 (0.03), 35/43 (0.04), 54/30 (0.05), 52/74 (0.07), 51/28 (0.1), 92/103 (0.15). Statistical analysis using chi-square test (A, C) and one-tailed unpaired Student's t test (B). ns, not significant. *, P<0.05; , P<0.01; *, P<0.001.

FIG. 3A-3K P-selectin regulates metastatic progression of M-CSCs. (A) Cell surface expression of selectins on HPMCs. E-selectin (E-sel), P-selectin (P-sel), L-selectin (L-sel). (B) Human omentum tissues stained with anti-selectin antibodies. Scale bar, 50 μm. (C, D) Rolling velocity (C), adhesion percentage (D) of M-CSCs on HPMCs pre-incubated with anti-selectins antibodies or IgG at 0.05 dynes cm$^{-2}$. n=59, 45, 83, 48. (E) Percentage of CSCs adhesion onto selectin recombinant proteins or Fc at 0.05 dynes cm$^{-2}$. n=35/39, 46/45, 52/63, 54/52. (F) Percentage of patient ascites-derived tumors adhesion onto selectins at 0.05 dynes cm-2. n=100, 131, 160, 247, tumor samples collected from 3 patients. Data (mean±SEM) from one of three independent experiments, chi-square test (D-F). (G, H) P-selectin wild type (Selp$^{WT}$) or knockout (Selp$^{-/-}$) Rag2 deficiency mice orthotopically (G) or i.p. (H) inoculated with M-CSCs cells. Arrows: metastases. Scale bar, 1 cm. n=6 mice (orthotopic) or 9 mice (i.p.) from two independent experiments. (I, J) Representative image (I) and H&E staining (I) of primary tumors in the ovary. Arrows, tumors. Scale bars=1 cm (I) or 50 μm (J). (K) Fluorescent signal of tumor cells adherent on mouse peritoneum. M-CSCs derived from SKOV-3 (left, n=3 mice) and patient samples (right, n=6 mice, tumor samples collected from two patients). Data (mean±SEM) from two independent experiments, unpaired Student's t test (I, K). ns, not significant. *, P<0.05; **, P<0.01.

FIG. 4A-4J sLe$^x$ mediates M-CSCs interaction with P-selectin on HPMCs. (A-E) Percentage of M-CSCs adhesion to HPMCs or P-selectin-Fc after treatment (A) Neuraminidase treatment n=73/35, 46/108. (B) Fucosidase treatment n=98/153, 67/64. (C) NaClO3 treatment n=49/65, 35/89. (D) Anti-sLe$^x$ treatment n=108/68, 89/71. (E) Anti-sLe$^a$ treatment. n=108/68, 89/71. (F) Cell surface expression of sLe$^x$ on CSCs. Left: representative images of flow cytometry. Right: relative positive cell plot n=3. (G-J) Percentage of M-CSCs adhered to HPMCs or P-selectin-Fc after treatment. (G) Trypsin treatment. n=32/36; 28/68. (H) PPMP treatment n=77/37, 54/46. (I) OSGE treatment. n=42/109, 54/95. (J) PNGase treatment. n=42/31, 54/31. Data (mean±SEM) from one of three independent experiments, chi-square test (A-E, G-J) or from three biological replicates, unpaired Student t test (F). ns, not significant. *, P<0.05; **, P <0.01.

FIG. 5A-5F The sLe$^x$-containing P-selectin ligand is IGF-1R-dependent (A, B) Percentage of adherent M-CSCs after treatment with RTK inhibitors on HPMCs. Genistein, general RTK inhibitor; AG1024, IGF-1R inhibitor; AG1478, EGFR inhibitor; K252a, c-Met inhibitor; SU5402, FGF-1R inhibitor. n=39, 36, 56, 20, 24, 24. (B) Percentage of M-CSCs adhesion to HPMCs or P-selectin-Fc after anti-IGF-1R treatment. n=45/71, 70/72. Data (mean±SEM) from one of three independent experiments, chi-square test (A, B). (C) Presence of IGF-1R in the M-CSCs protein lysate pulled down with P-selectin-Fc. (D) Detection of HECA-452 antigen on IGF-1R of M-CSCs. (E) P-selectin binding on M-CSCs activates the phosphorylation of IGF-1R. (F) mRNA expression of CD24 (left) and IGF-1R (right) in M-CSCs and NM-CSCs. Data (mean±SEM) from three biological replicates, n=3, unpaired Student t test. ns, not significant; *, P<0.05; , P<0.01; *, P<0.001.

FIG. 6A-6G FUT5 is critical for ovarian cancer progression. (A) mRNA expression of glycogenes related with sLe$^x$ biosynthesis. Left: schematic image indicating sLe$^x$ biosynthesis. sLe$^x$ is synthesized by sequential addition of N-acetylglucosamine (GalNAc), galactose (Gal), sialic acid (NeuAc), and fucose (Fuc) to the backbone catalyzed by N-acetylglucosaminyltransferases (GnTs), β1,4-Galactosyl-transferase (B4GalT1-4), α 2,3-Sialyltransferases (ST3Gal3, 4, 6) and a, 1,3-Fucosyltransferase (FUT3-7, 9). Middle: mRNA expression of glycogenes in M-CSCs and NM-CSCs. n=3 per group. Right: mRNA expression of glycogenes in normal human ovarian surface epithelial (OSE) cells and M-CSCs collected from ovarian cancer patients (OvCa). n=2 patients (OSE) or n=4 (OvCa). Data represent as mean±SEM, unpaired Student's t test. (B) Detection of HECA-452 antigen on FUT5 knockdown M-CSCs. Data (mean±SEM) from three biological replicates, n=3, unpaired Student's t test. (C) Percentage of FUT5 knockdown M-CSCs adhered onto HPMCs or P-selectin-Fc. n=64/55, 67/35. Data (mean±SEM) from one of three independent experiments, chi-square test. (D) Metastasis in mice with NS or FUT5 shRNA transduced M-CSCs orthotopic (upper) or i.p. (lower) xenograft model. Arrows: metastases. Scale bar, 1 cm. n=3 mice (orthotopic) or 6 mice (i.p.). (E, F) Representative images (E) and H&E staining (F) of primary tumors in mice. Arrows, tumors. Scale bars=1 cm (E) or 50 μm (F). (G) FUT5 mRNA expression of in primary tumors. n=3 mice per group. Data (mean±SEM) from three biological replicates, n=3, unpaired Student's t test. Experiments were conducted two (D-F) or three (A-C, G) times independently. ns, not significant. *, P<0.05. , P<0.01; *, P<0.001.

FIG. 7 Schematic of sLe$^x$-P-selectin binding in peritoneal metastasis.

FIGS. 8A-B (A) Schematic diagram of tumor cells flowing through a microchannel with metastatic cells selectively captured on P-selectin coated channel bottom. (B) The geometric pattern of the microfluidic channel (Left) and the equation for the conversion of volumetric flow rate to wall shear stress within the channel (right).

FIG. 9A-9E show results of flow adhesion assay. (A) Transient velocities of representative cells on P-selectin recombinant protein. Triangles represent a rolling adhesion highly metastatic (HM) cells; Circles represent a non-interaction non-metastatic (NM) cells quickly passed through the channel. Under shear stress of 0.1 dyne/cm$^2$, HM cells showed steady rolling before firm adhesion on P-selectin substrate. (B) Rolling percentage of NM and HM cells on P-selectin recombinant protein. (C) Cumulative frequency rolling velocity histograms. (D) Adhesion percentage of NM and HM cells on P-selectin recombinant protein. HM or NM cells were introduced into flow chambers pre-coated with 1 g/ml P-selectin-Fc chimera or Fc control at shear stress of 0.1 dyne/cm2. Cell movement was observed under microscope and captured with high speed camera. Cancer cells rolling velocity was calculated by dividing moving distance with duration. Rolling was defined as cancer cells moving under critical velocity (50% of hydrodynamic flow rate) and did not stop during observation. Adhesion was defined as cancer cells stop moving for more than one second during recording. The rolling or adhesion fraction was quantified through dividing the number of rolling or adhesive cells by the total number of cells traveled into the field of observation area for 30 seconds. (E) Adhesion percentage of NM and HM cells on P-selectin-Fc chimera at shear stress of 0.05-0.15 dyne/cm2. Data are presented as mean±S.E.; *P<0.05, **P<0.01.

HM cells has distinct binding capability on P-selectin recombinant protein under flow. Compared with NM cells, HM exhibited higher rolling frequency P-selectin (77.2%) (9B), with lower velocity (9C), subsequently remarkably higher adhesion capability on P-selectin (about 6 folds higher than NM) (9D). The differential binding property between metastatic cells with non-metastatic cells got more obvious with the increase of wall shear stress, NM cells were all washed away at a shear stress above 0.1 dyne/cm$^2$ (9E), indicating greater capacity of HM cells to support P-selectin-mediated rolling adhesion over a broader range of shear stress.

FIG. 10A-10B show EDTA detachment assay. Captured metastatic cells were easily detached from the channel bottom through perfusing EDTA solution. (A) A brightfield microscope image of captured HM cells. White dots are tumor cells attached on channel bottom. (B) A brightfield microscope image of channel after EDTA detachment. HM cells in binding buffer were initially introduced into the channels coated with P-selectin recombinant protein at a shear stress of 0.1 dynes/cm2 for 1 min followed by perfusion with PBS for 1 min at the same shear stress. Then perfuse the channel with 5 mM EDTA solution at a shear of stress 1 dynes/cm$^2$ for 1 min. The microfluidic channel before or after EDTA detachment was observed under a microscope. Scale bar, 50 μm.

FIG. 11 shows adhesion percentage of primary tumor cells on P-selectin recombinant protein under flow.

FIG. 12 shows a table with antibodies and recombinant proteins.

FIG. 13 shows a table with biochemical inhibitors.

FIG. 14 shows a table with DNA primers.

FIG. 15 shows a table with Metastasis in Selp$^{WT}$ and Selp$^{-/-}$ mice.

FIG. 16 shows a table with meatstatsis in mice with NS or FUT5 shRNA transduced M-CSCs.

Figure 17:
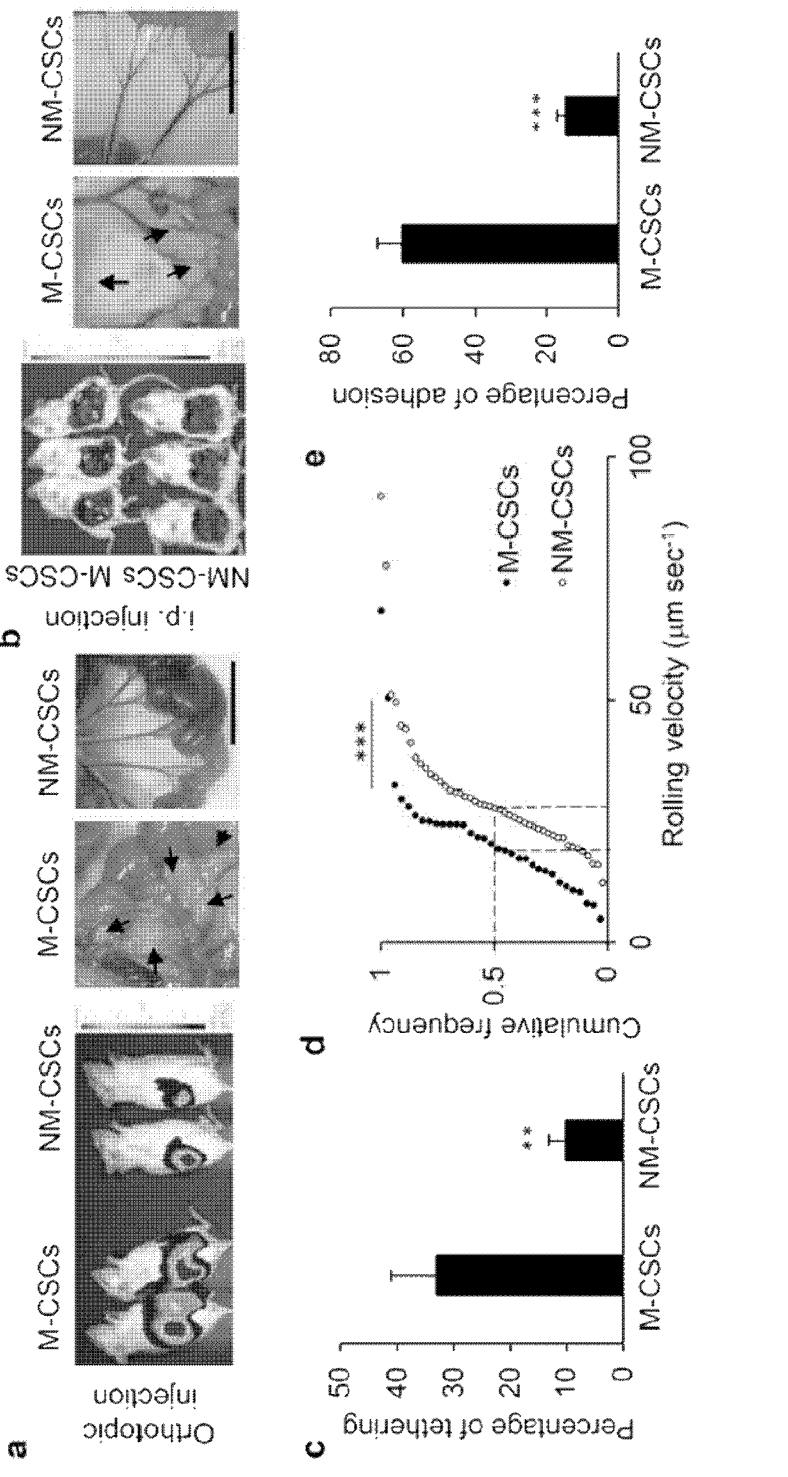

FIG. 17 shows Characterization of HEYA8 M-CSCs. NOD/SCID mice engrafted with HEYA8 M-CSCs or NM-CSCs via orthotopic (a) or i.p. (b) injection. N=3 mice per group, In vivo tumor xenograft experiments were conducted twice. Left: representative bioluminescence image. Right: representative views of metastases in the peritoneal cavity.

Scale bar, 1 cm. c Percentage of tethering of HEYA8 M-CSCs and NM-CSCs on HPMCs at 0.05 dyne cm-2. d Cancer spheroids rolling velocities on HPMCs at 0.05 dyne cm-2. e Percentage of HEYA8 M-CSCs and NM-CSCs adhered onto HPMCs. n=31/45. Data (mean±SEM) from one of three independent experiments. Statistical analysis using chi-squared test (c, e) and one-tailed unpaired Student's t test (d). , P<0.01; *, P<0.001.

Figure 18:
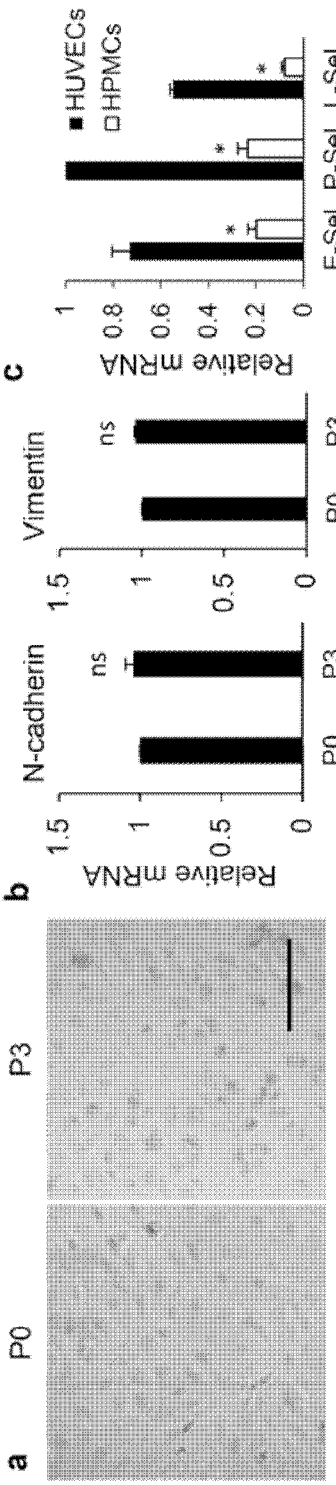

FIG. 18 shows Morphology and gene expression of HPMCs. a Representative brightfield images of HPMCs at low passages (passage 0 and 3). Scale bar, 100 mm. b The mRNA expression of EMT markers in different passages of HPMCs. c The mRNA expression of selectins in HPMCs and HUVECs. Data (mean±SEM) from two biological replicates, n=2, paired (b) or unpaired (c) Student's t test. ns, not significant; *, p<0.05.

Figure 19:
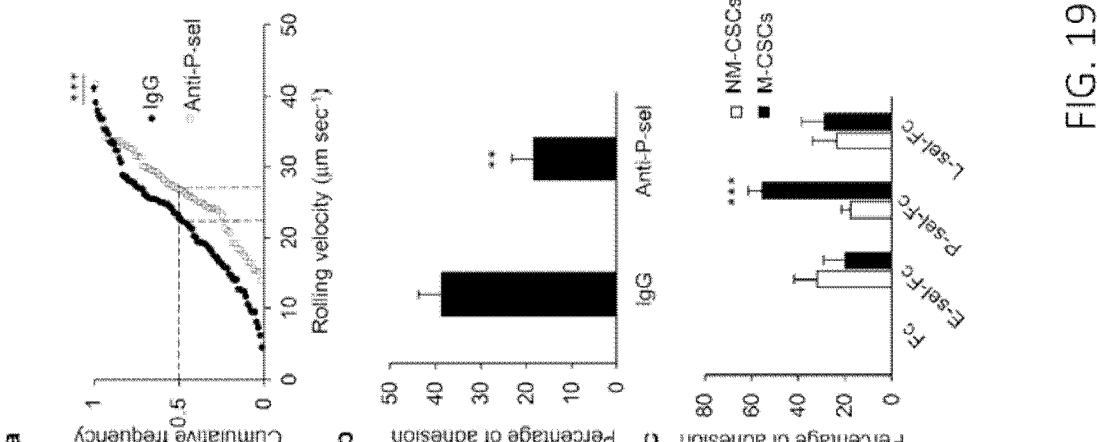

FIG. 19 shows P-selectins mediates HEYA8 M-CSC-HPMC interaction. a, b Cumulative frequency (a) and adhesion percentage (b) of HEYA8 M-CSCs on HPMCs blocked with anti-P-selectin at 0.05 dyne cm-2. n=93/65. c Percentage of HEYA8 M-CSCs and NM-CSCs adhered onto selectins at 0.05 dyne cm-2. n=36/76, 20/22, 65/97, 21/17. Data (mean±SEM) from one of three independent experiments. Statistical analysis using unpaired Student's t test (a) and chi-squared test (b, c). , p<0.01; *, p<0.001.

Figure 20:
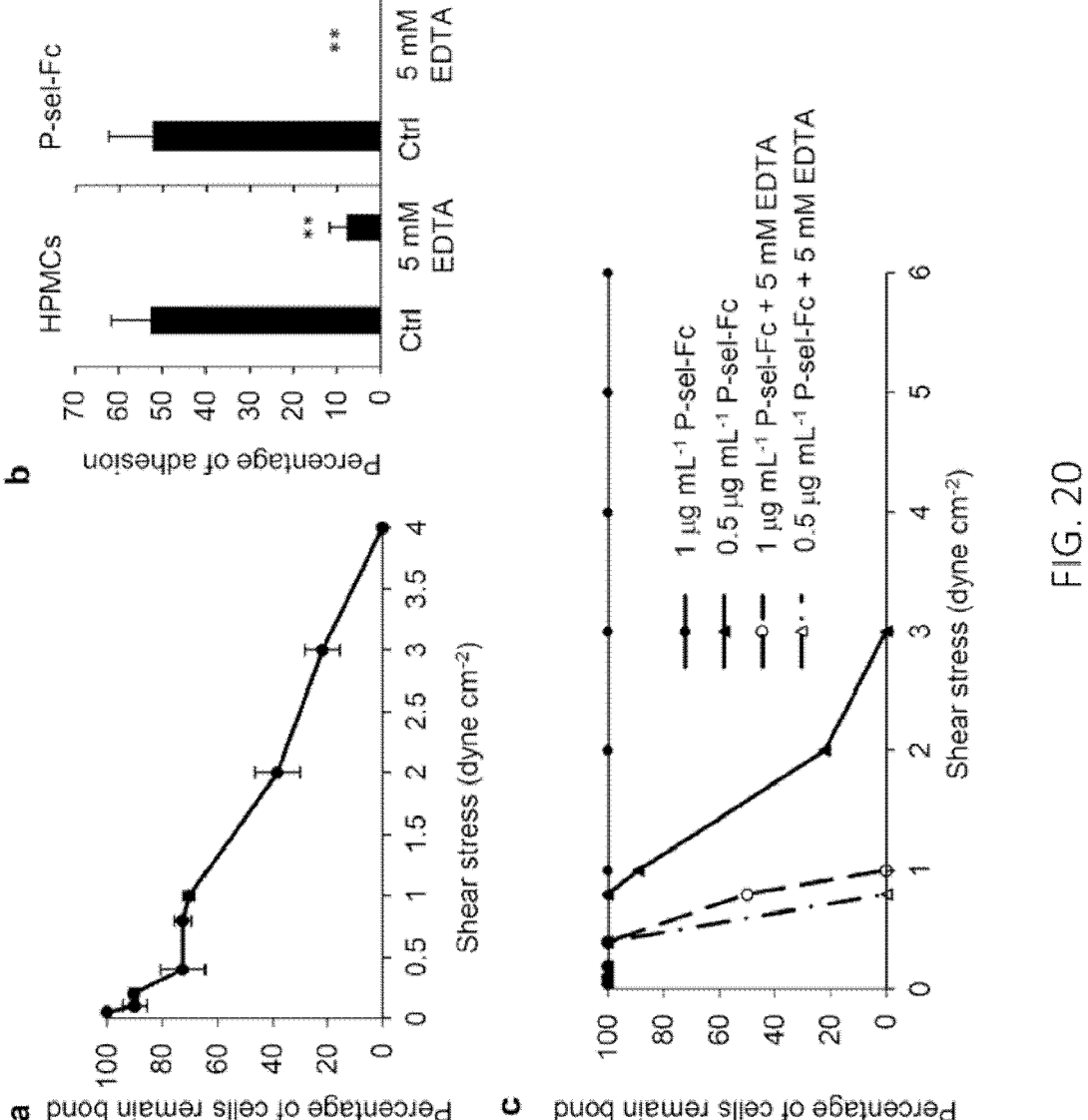

FIG. 20 shows the P-selectin-mediated binding is shear-resistant and Ca2+-dependent. a Detachment of SKOV-3 M-CSCs on HPMCs. b Percentage of SKOV-3 M-CSCs adhered on HPMCs or P-selectin-Fc in the presence or absence of in EDTA at 0.05 dyne cm-2. n=31/58, 21/11. Data (mean±SEM) from one of two independent experiments, chi-square test. **, p<0.01. c Detachment of SKOV-3 M-CSCs on P-selectin-Fc the presence or absence of EDTA.

Figure 21:
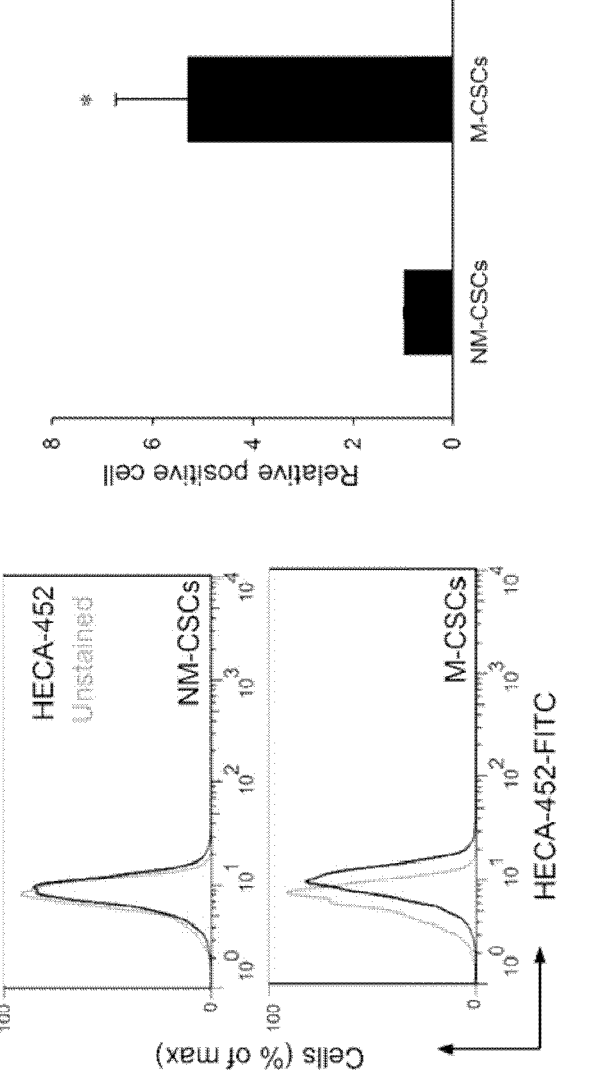

FIG. 21 shows sLea/x expression on HEYA8 M-CSCs and NM-CSCs cells. Left: representative images of flowcytometry. Right: relative positive cell plot. Data (mean±SEM) from three biological replicates, n=3, unpaired Student t test. *, p<0.05.

Figure 22:
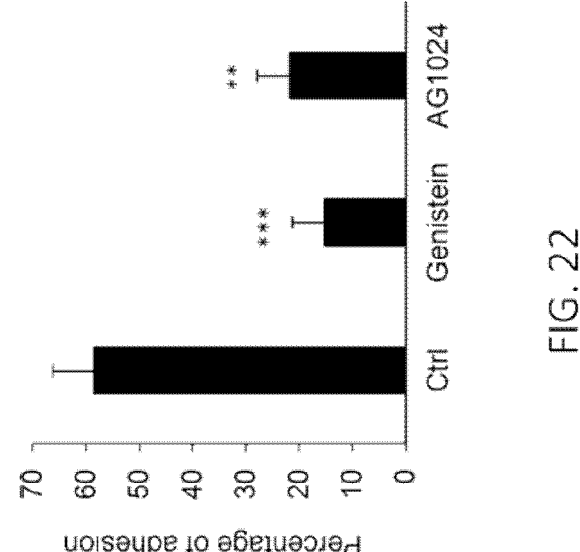

FIG. 22 shows Percentage of adherent M-CSCs on P-selectin-Fc after inhibitor treatment. SKOV-3 M-CSCs were treated with or without general RTK inhibitors genistein or IGF-1R inhibitor AG1024 before perfusion on P-selectin-Fc recombinant protein. n=41, 33, 46. Data (mean±SEM) from one of three independent experiments, chi-square test. , P<0.01; *, P<0.001.

Figure 23:
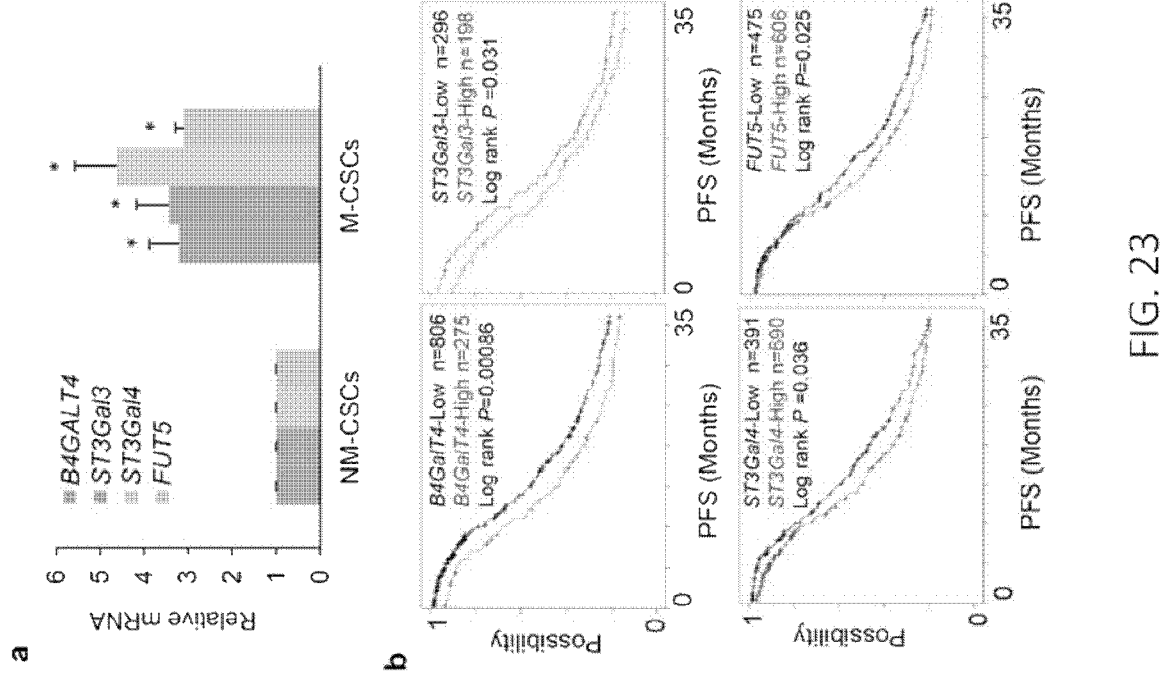

FIG. 23 shows the correlation between glycosyltransferases with metastatic properties and patient prognosis. a The mRNA expression of glycogenes in HEYA8 M-CSCs and NM-CSCs. Data (mean±SEM) from three biological replicates, n=3, unpaired Student t test. *, P<0.05. b Kaplan-Meier progression-free survival (PFS) analysis of B4GalT4, ST3Gal3, ST3Gal4 and FUT5 expression in advanced-stage ovarian cancer patients with high (red) and low (black) expression levels of specific genes. Statistical analysis using log-rank test.

Figure 24:
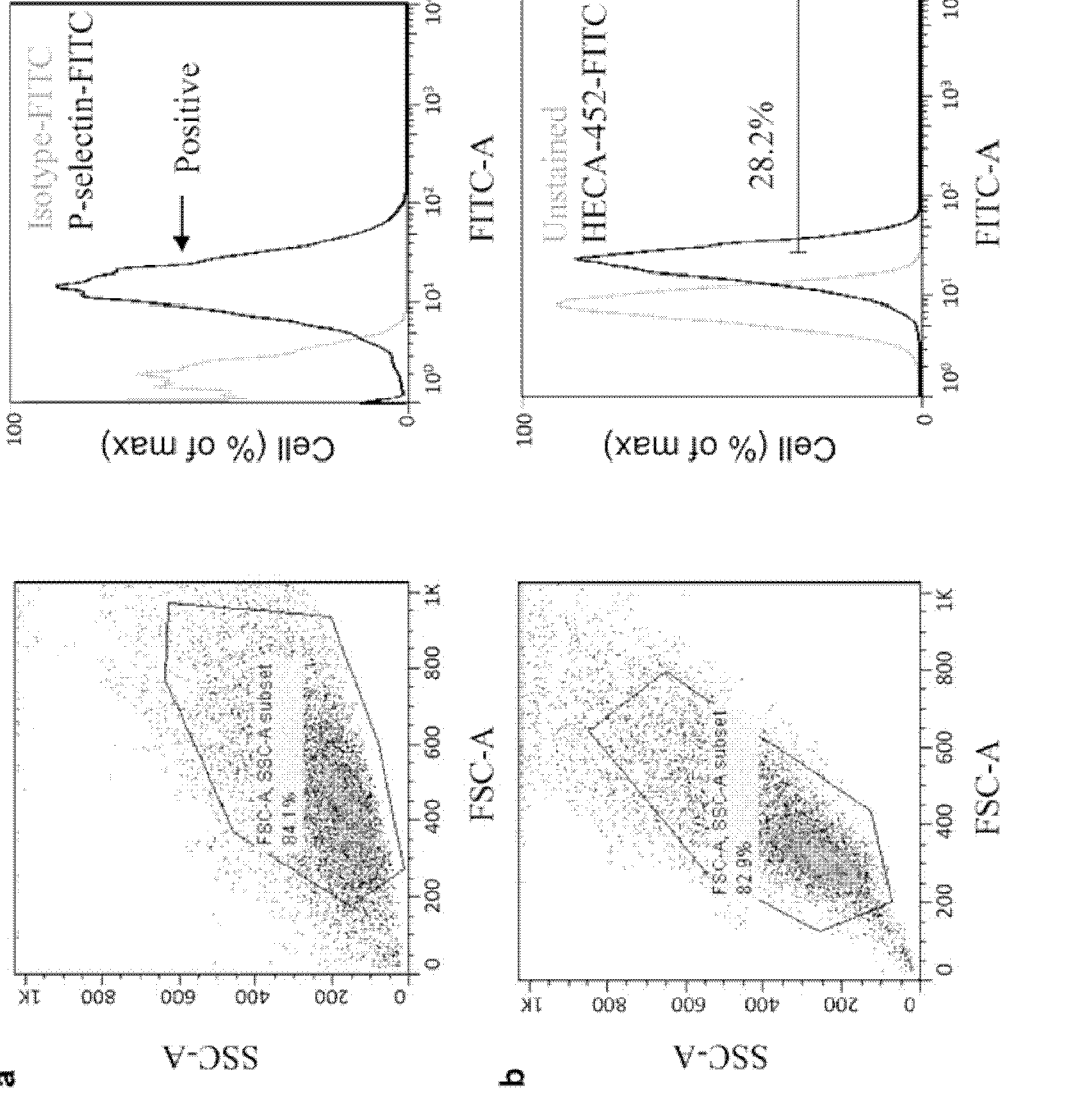

FIG. 24 shows gating strategies for flow cytometry analysis. a Representative gating strategy for cell surface staining of selectin on HPMCs. b Representative gating strategy for cell surface staining of HECA-452 on SKOV-3 M-CSCs.

FIG. 25 shows scans of the full blots from the Western blot.

Figure 26:
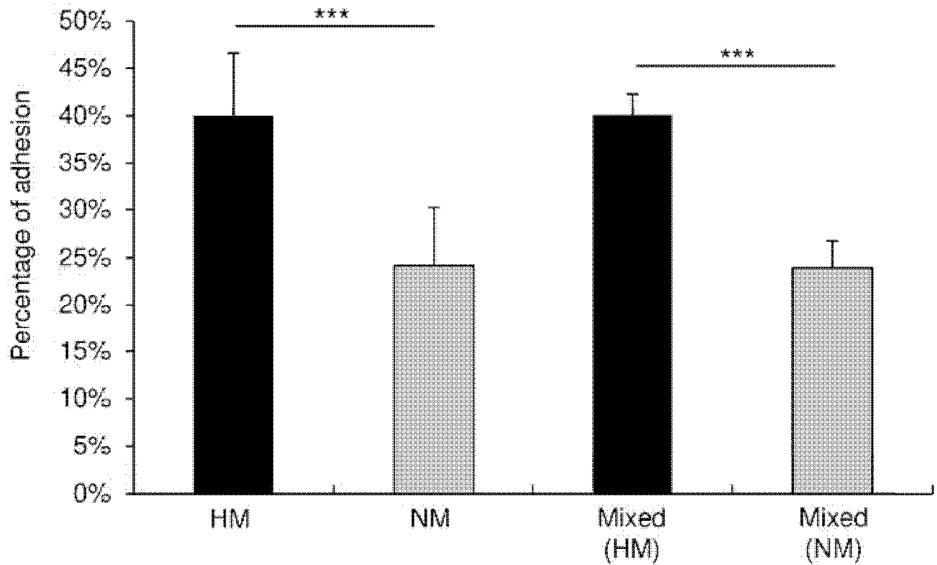

FIG. 26 shows differential capture of highly metastatic and non-metastatic SKOVip1 cells with microfluidic chip. Highly metastasis (HM) SKOVip1 and non-metastatic (NM) SKOVip1 cell were perfused into the microfluidic chip at a shear stress of 0.1 dynes/cm2. In the mixed samples, HM and NM cells were mixed in 1:1 ratio, only one of them was fluorescently labeled and counted. Cells were labeled with CMFDA Celltracker (2.5 mg/mL). The motion of the cells was observed under fluorescent microscope and captured for 30 s at a speed of 1 image/s. 4 random areas for each sample were selected for data analysis. ***P<0.001.

FIG. 27 shows differential capture of ovarian cancer cell lines with different metastatic potential. (a) Highly metastasis (HM) HeyA8 and non-metastatic (NM) HeyA8 cells; (b) Omentum derived (omen) and ovary derived (ov) OVSAHO cells; (c) SKOV-3 and OVCAR-3 cells were perfused into the microfluidic chip at a shear stress of 0.1 dynes/cm2. Cells were labeled with CMFDA Celltracker (2.5 mg/mL). The motion of the cells was observed under fluorescent microscope and captured for 30 s at a speed of 1 image/s. 4 random areas for each sample were selected for data analysis. P<0.01; *P<0.001.

FIG. 28 shows differential capture of colorectal and prostate cancer cells with different metastatic potential. (a) SW620 and SW480 colorectal cancer cells alone, or mixed in 1:1 ratio; (b) LNCaP and PC3 prostate cancer cells; (c) MKN45 and AGS gastric cancer cells were perfused into the microfluidic chip at a shear stress of 0.1 dynes/cm2. Cells were labeled with CMFDA Celltracker (2.5 mg/mL). The motion of the cells was observed under fluorescent microscope and captured for 30 s at a speed of 1 image/s. 4 random areas for each sample were selected for data analysis. P<0.01; *P<0.001.

FIG. 29 shows microfluidics chip as an anti-metastasis drug screening platform. Highly metastasis SKOVip1 cells were treated with (a) Defactinib, or DMSO (as solvent control); (b) A6 peptide, or PBS (as solvent control) for 24 h. Cells were then perfused into the microfluidic chip at a shear stress of 0.1 dynes/cm2. Cells were labeled with CMFDA Celltracker (2.5 mg/mL). The motion of the cells was observed under fluorescent microscope and captured for 30 s at a speed of 1 image/s. 4 random areas for each sample were selected for data analysis. ***P<0.001.

5. DETAILED DESCRIPTION

Organ-specific colonization suggests that specific cell-cell recognition is essential. Yet, very little is known about this particular interaction. Moreover, tumor cell lodgement requires binding under shear stress, but not static, conditions. Here, we successfully isolate the metastatic populations of cancer stem/tumor-initiating cells (M-CSCs). We show that the M-CSCs tether more and roll slower than the non-metastatic (NM)-CSCs, thus resulting in the preferential binding to the peritoneal mesothelium under ascitic fluid shear stress. Mechanistically, this interaction is mediated by P-selectin expressed by the peritoneal mesothelium. Insulin-like growth factor receptor-1 carrying an uncommon non-sulfated sialyl-Lewis$^x$ (sLe$^x$) epitope serves as a distinct P-selectin binding determinant. Several glycosyltransferases, particularly at 1,3-fucosyltransferase with rate-limiting activity for sLe$^x$ synthesis, are highly expressed in M-CSCs. Tumor xenografts and clinical samples corroborate the relevance of these findings. These data advance our understanding on the molecular regulation of peritoneal metastasis and support the therapeutic potential of targeting the sLe$^x$-P-selectin cascade.

Ovarian cancer has the lowest 5-year survival rate (<25%) among all gynecological malignancies due to extensive peritoneal metastatic lesions[1]. Despite not as common as blood-borne metastasis, treatment of peritoneal metastasis is notoriously challenging because of the rapid growth of metastasis in the peritoneal cavity in a positive feed-forward manner[2]. Current treatment is dissatisfying and little overall clinical benefits for patients have been achieved over the last several decades. Unraveling the underlying molecular mechanisms regulating this process will conceivably benefit the development of effective treatment strategies.

The barriers to metastasis are distinct in different organs, suggesting that specific recognition between cancer cells and peritoneal mesothelium is critical for the peritoneum-specific colonization[3]. Moreover, tumor cell lodgment in the peritoneum is consistently exposed to shear forces generated by ascitic flow[4]. However, due to the difficulty in manipulating the dynamic flow conditions, the role of mechanical force in this adhesion has been largely neglected. Thus, the adhesion molecules and the underlying signaling operating the adhesion of cancer cells under ascitic flow remain a gap in knowledge.

Selectins (E-, P-, and L-selectin) are a family of calcium-dependent glycoproteins that are the prime glycan receptors on shear-resistant interactions as described to date[5]. Although the structures of the three selectins are highly similar, their tissue distribution and binding kinetics are different, reflecting their divergent roles in various pathophysiological processes, including tumor metastasis. Thus, the selective binding between selectin and its ligand determines the metastatic destination. Tumor cells exploit the selectin-glycan binding for the initial cell-cell interaction, including tethering and rolling, under shear stress which further triggers the molecular signaling that facilitates cellular firm adhesion[6]. Such interaction has been extensively studied in blood-borne metastasis[7,8]. In contrast, selectins are expressed on peritoneal mesothelial cells, suggesting that similar receptor/ligand cascade initiated by selectin-mediated interaction may promote tumor cell peritoneal targeting[9,10]. However, the detailed underlying mechanism governing adhesion for peritoneal metastasis is poorly understood. The difference in the peritoneal shear stress (~0.1 dyne cm$^{-2}$; at least 10-fold lower than that of the vascular shear stress)[11] suggests that the biology of peritoneal dissemination is different from that of blood-borne metastasis and probably different molecular mechanisms are involved.

We discuss a preferential binding of metastatic cancer stem/tumor-initiating cells (M-CSCs) to the peritoneal mesothelium than the non-metastatic (NM)-CSCs. We also provide evidence that P-selectin is a key molecule on the peritoneal mesothelium that mediates the binding through a unique sialyl-Lewis$^x$ (sLe$^x$) containing insulin-like growth factor receptor-1 (IGF-1R) ligand under ascitic flow-induced shear stress.

Patient Samples

For detecting cancer, a test sample is obtained from a patient. The patient may or may not have cancer. In this case, the methods of the invention are used to diagnose or detect whether the patient has cancer, or a particular type of cancer, or has a propensity for developing cancer, or a particular type of cancer. Alternatively, the methods of the invention can be used with patients that are known to have cancer, or a particular type of cancer. In this case, the prognosis of cancer, or a particular type of cancer, can be monitored. Complementary such approaches are utilized for any of various specific cancers, including ovarian cancer, breast cancer, lung cancer, etc. such as and including as described further below and herein.

With regard to disease or cancer for assessment, the test sample obtained from the patient can be any tissue, pathology or bodily fluid sample. For example, the test sample can be a blood sample, a serum sample, a plasma sample, a urine sample, a cervical secretion sample, a vaginal secretion sample, an ovarian fluid or tissue sample, an ascites fluid sample, a plural ascites fluid sample, a saliva sample, a cerebrospinal fluid sample, or a tissue sample. In many embodiments, the sample is a serum sample.

Detection of binding can be direct, for example, by detection of a label attached to a molecule that binds to antibodies or other proteins or polypeptides. Detection can be indirect, for example, by detecting a labeled secondary antibody that can bind to human antibodies. The bound label can be observed using any available detection method. For example, an array scanner can be employed to detect fluorescently labeled molecules that are bound to array. In experiments illustrated herein a ScanArray 5000 (GSI Lumonics, Watertown, Mass.) confocal scanner was used. The data from such an array scanner can be analyzed by methods available in the art, for example, by using ImaGene image analysis software (BioDiscovery Inc., El Segundo, Calif.).

In general, as illustrated herein, detection of increased P-selectin binding by antibodies (or other binding entities) in a patient's serum is an indicator that the patient may have cancer, including as described herein ovarian cancer, breast cancer, lung cancer. Comparison of the levels of P-selectin binding over time provides an indication of whether the cancer is progressing toward metastasis, whether a patient is responding to a selected treatment or whether the cancer is in remission. Hence, also provided herein are methods for monitoring the progression of cancer in a patient.

According to one aspect, the biological sample may be a fluid or solid body sample from a patient, specifically a sample of blood, serum, plasma, urine, tissue, bone, cartilage, organs, etc. This tissue sample may be a sample of a primary tumor, and the control may be either a sample of a non-metastatic tumor tissue or a standard. These samples may be taken and if necessary prepared according to methods known to a person skilled in the art. In certain embodiment, the methods of expanding cells in a microfluidic device (or "chip") are disclosed. The microfluidic device can include a microfluidic channel and a sequestration pen fluidically connected to the channel, with the sequestration pen configured to support the culture and expansion of cells. In certain embodiments, the microfluidic device can be a nanofluidic device. The sequestration pen can have a volume, for example, of about 0.5×106 to about 5.0×106 cubic microns, or about 0.5×106 to about 2.0×106 cubic microns. Furthermore, the microfluidic device can have more than one microfluidic channel and a plurality of sequestration pens fluidically connected to each microfluidic channel, with each sequestration pen of the plurality configured to support the culture and expansion of cells. The cells may be metastatic or non-metastatic cells. One or more surfaces of the sequestration pen(s) can be conditioned.

The methods of expanding cells can include: introducing one or more cells into the sequestration pen in the microfluidic device; and contacting the one or more cells with a marker, P-selectin or E-selectin. In some embodiments, 20 or fewer, 10 or fewer, 6 to 10, 5 or fewer, about 5, about 4, about 3, about 2, or 1 cells are introduced into the sequestration pen. If the microfluidic device includes a plurality of sequestration pens, one or more cells (e.g., 20 or fewer, 10 or fewer, 6 to 10, 5 or fewer, about 5, about 4, about 3, about 2, or 1 cells) can be introduced into each of one or more sequestration pens. The methods of expanding cells can further include perfusing culture medium through the microfluidic channel of the microfluidic device. The perfusion can be continuous or intermittent and can last for a period of time sufficient to allow the one or more cells introduced into the sequestration pen (or sequestration pens) to undergo at least one round of mitotic cell division. Specific binding of peritoneal cells to the markers disclosed herein may be determined by flow adhesion assay. Transient velocities of peritoneal metastatic cells and peritoneal non-metastatic cells was calculated by dividing moving distance with duration. Rolling was defined as cancer cells moving under critical velocity (50% of hydrodynamic flow rate) and did not stop during observation. Adhesion was defined as cancer cells stop moving for more than one second during recording. The rolling or adhesion fraction is then quantified. Metastatic cells have distinct binding capability on P-selectin under flow.

In one embodiment, the metastatic cells are obtained from a solid tumor sample of a subject. The solid tumor sample can be a fine needle aspirate (FNA) or a tumor biopsy (e.g., a core biopsy). The solid tumor can be a breast cancer, genitourinary cancer (e.g., a cancer originating in the urinary tract, such as in the kidney (e.g., renal cell carcinoma), ureter, bladder, or urethra; cancer of the male reproductive tract (e.g., testicular cancer, prostate cancer, or a cancer of the seminal vesicles, seminal ducts, or penis); or of the female reproductive tract (e.g., ovarian cancer, uterine cancer, cervical cancer, vaginal cancer, or a cancer of the fallopian tubes)), a cancer of the nervous system (e.g., neuroblastoma, retinal blastoma), intestinal cancer (e.g., colorectal cancer), lung cancer, melanoma, or another type of cancer. In specific embodiments, the solid tumor can be a medullary breast cancer, a mesothelioma, or a melanoma.

The sample can be from a subject, such as a subject that is suffering from cancer (e.g., any type of cancer described herein or known in the art). The sample can be a peripheral blood sample or a derivative thereof (e.g., a sample of PBMCs). Alternatively, the sample can be a solid tumor biopsy. In some embodiments, a peripheral blood sample is processed to enrich for cells. In other embodiments, a tumor sample is processed to enrich cells. In still other embodiments, a tumor sample is processed to enrich for peritoneal cells.

In certain embodiments, culture medium is perfused through the microfluidic channel of the microfluidic device for a period of at least 24 hours (e.g., at least 48, 72, 96, 110, or more hours, or any number therebetween). In certain embodiments, the culture medium includes mammalian serum, which can be a human serum (e.g., Human AB serum), optionally in combination with a bovine serum (e.g., fetal bovine serum or calf serum).

Kit

Provided is a diagnostic kit used to determine the specific binding of peritoneal cells in a sample to the markers according to the disclosure in biological samples, namely by comparing binding of the peritoneal cells in a sample of interest that contains the marker or markers with controls or standards, specifically with respect to increased expression of the marker(s). The diagnostic kit is therefore particularly well-suited for the early detection of metastatic primary tumors, which in turn allows rapid and targeted therapy. Thus this diagnostic kit-as well as to claimed method-can also be used e.g. to distinguish between non-metastatic and metastatic peritoneal cells. The diagnostic kit should preferably contain e.g. one or more labels that react with the marker/marker or cells according to the disclosure.

The disclosure provides a kit for diagnosing or monitoring cancer in an individual wherein the P-selectin binding profile of a test sample from said individual is determined and comparing the measured profile with a profile of normal patient or profile of a patient with a family history of cancer.

The present disclosure further pertains to a packaged pharmaceutical or diagnostic composition such as a kit for detecting, controlling, preventing or treating a neoplasia (e.g., ovarian cancer, breast cancer, lung cancer) or other disorder. In one exemplary embodiment, the kit or container holds an array or library of P-selectin for detecting cancer and instructions for using the array or library of P-selectin for detecting the cancer. The array includes at least one P-selectin that is bound by antibodies present in serum samples of a cancer patient.

The kits can also comprise containers with tools useful for administering the compositions of the invention. Such tools include syringes, swabs, catheters, antiseptic solutions and the like.

Microfluidic Device

Any of the methods of described herein may be performed using a microfluidic device that has one or more inner surfaces (e.g., a substrate surface, a cover surface, and/or the surfaces of the circuit material) that have been conditioned or coated so as to present a layer of organic and/or hydrophilic molecules that provides the primary interface between the microfluidic device and cells grown therein. For example, the flow path and the sequestration pen(s) can be treated with a coating solution that bonds to one or more inner surfaces and presents and organic and/or hydrophilic layer of molecules. Thus, the coating solution can comprise a coating agent that binds to the one or more inner surfaces, such as serum, serum albumin (e.g., BSA), polymer, detergent, enzymes, or any combination thereof.

In certain embodiments, the microfluidic device can comprise an inner substrate surface (and/or an inner cover surface and/or inner surfaces of the circuit material) that comprise a coating material. In some embodiments, the coating material includes molecules having a linking group and an alkyl moiety. The linking group can be covalently bonded to the inner substrate surface, and can be, for example, a siloxy linking group. The alkyl moiety can be, for example, an unsubstituted alkyl moiety or a substituted alkyl moiety, such as a fluoroalkyl moiety or a perfluoroalkyl moiety. The alkyl moiety can include a linear chain of carbons comprising at least 10 carbon atoms (e.g., at least 12, 14, 16, 18, 20, 22, or more carbon atoms). The molecules of the coating material can form a densely-packed monolayer structure covalently bound to the inner substrate surface (and/or the inner cover surface and/or the inner surfaces of the circuit material).

In some embodiments, the coating material comprises molecules having a linking group and a cationic moiety and/or an anionic moiety, wherein the linking group is covalently bonded to the inner substrate surface (and/or the inner cover surface and/or the inner surfaces of the circuit material). The cationic moiety can include a quaternary ammonium group. The anionic moiety can include a phosphonic acid, carboxylic acid, or sulfonic acid. In some related embodiments, the coating material can comprise molecules having a linking group and a zwitterionic moiety, wherein the linking group is covalently bound to the inner substrate surface (and/or the inner cover surface and/or the inner surfaces of the circuit material). The zwitterionic moiety is selected from carboxybetaines, sulfobetaines, sulfamic acids, and amino acids. In some embodiments, the cationic, anionic, or zwitterionic moieties are capable of ionically bonding with a blocking agent).

In some embodiments, the coating material comprises a polymer comprising alkylene ether moieties, saccharide moieties, or amino acid moieties. For example, the coating material can comprise dextran or polyethylene glycol (PEG). Alternatively, or in addition, the coating material can comprise protein polymers (e.g., proteins that maintain cell growth).

Microfluidic device is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow path, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 μL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 μL. The microfluidic circuit may be configured to have a first end fluidically connected with a first port (e.g., an inlet) in the microfluidic device and a second end fluidically connected with a second port (e.g., an outlet) in the microfluidic device.

A "microfluidic channel" or "flow channel" as used herein refers to flow path of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the microfluidic device.

As used herein, a "flow path" or "flow region" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device. The micro-object may still be capable of motion within an in situ-generated capture structure.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. One of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

The markers and/or cells that are useful in the present disclosure can have linkers, labels, linking moieties and/or other moieties attached to them. The labels most commonly employed for these studies include radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The P-selectin and/or cells can also be labeled with a radioactive element or with an enzyme. The radioactive label can be detected by any of the currently available counting procedures. Enzyme labels are likewise useful, and can be detected by any of the art-recognized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. U.S. Pat. Nos. 3,654,090; 3,850, 752; and 4,016,043 are referred to by way of example for their disclosure of alternate labeling material and methods.

Data Analysis/Review/Transmission

In another embodiment, a result obtained using the methods described herein is used for detection/treatment/prevention of early stage diseases and/or neoplasia of an individual, for example, a patient. In a further embodiment, the method of detection/treatment/prevention of early stage diseases and/or neoplasia includes reviewing or analyzing data relating to the presence of, for example, circulating antibodies that react with cancer-related epitopes in a sample. A conclusion is then provided to a patient, a health care provider or a health care manager, the conclusion being based on the review or analysis of data regarding a disease diagnosis or early stage disease detection. It is envisioned that in another embodiment that providing a conclusion to a patient, a health care provider or a health care manager includes transmission of the data over a network.

6. MATERIALS AND METHODS

6.1 Cells and Cell Culture

Human ovarian cancer cell lines SKOV-3 and HEYA8 (kind gifts from Dr. N. Auersperg at University of British Columbia and Dr. J Liu at MD Anderson Cancer Center, respectively) were maintained in Medium 199:MCDB105 containing 5% FBS. CSCs were enriched from luciferase-labeled SKOV-3 and HEYA8 through several generations of serum-free low adherent culture and stem-like properties were characterized as described[12]. HEK293 cells (CRL-1573, ATCC) were cultured in DMEM medium containing 10% FBS. HUVECs (CC-2519, Clonetics) were cultured in F12K supplemented with 10% FBS, 20 µg mL$^{-1}$ endothelial cells growth supplement, 90 U mL$^{-1}$ heparin and 1% penicillin and streptavidin. Primary tumor samples were obtained from ovarian cancer patients with informed consent and approval by the Taipei Medical University Institutional Review Board and isolated as described[25]. The use of human tumor surgical specimens and tissue samples was approved by the Institutional Ethical Review Board at the University of Hong Kong. Normal human ovarian surface epithelial (OSE) cells were derived from surface scrapings of normal ovaries from women with nonmalignant gynecological diseases. HPMCs isolated from dialysate effluent from peritoneal dialysis from patients with nonmalignant disorders[47] were maintained in Medium 199:MCDB105 supplemented with 10% FBS, 1% penicillin and streptavidin. HPMCs within 3 passages were used to ensure genetic stability of the culture.

Isolation of M-CSCs

CSCs (1×10$^5$) were injected into the ovary of NOD/SCID mouse (female, 6-8 weeks of age) to allow the formation of primary tumor and intraperitoneal dissemination. M-CSCs were collected from the ascites, whereas NM-CSCs were collected from the tumor burden remained in the ovary at 3 weeks' post inoculation. M-CSCs or NM-CSCs were maintained in serum-free medium in low adherent culture dishes as early described. To further verify the tumorigenesis and metastasis potential of the isolated populations, NM-CSCs or M-CSCs were orthotopically (1×10$^5$) or intraperitoneally (5×10$^5$) injected into NOD/SCID mice. Tumor burden was monitored by bioluminescence imaging and mice were harvested at 3-4 weeks post-inoculation. All animal experiment protocols were approved by the Committee on the Use of Live Animals in Teaching and Research at the University of Hong Kong.

Antibodies

The antibodies or recombinant proteins used in the flow cytometry, Western blot, IHC or microfluidic perfusion assays are detailed in the FIG. 12.

RNA Sequencing and TCGA Data Analysis

Total RNA extracted from three pairs of M-CSCs and NM-CSCs were sent to Beijing Genomics Institute (BGI) for RNA-sequencing (RNA-seq). Differential gene expression between M-CSCs and NM-CSCs was determined by a moderated t-test with limma software. 200 genes were identified up-regulated in the M-CSCs compared with NM-CSCs (log 2(fold-change)>1 and P<0.05), and 216 genes were identified down-regulated (log 2(fold-change)<−1 and P<0.05). Hierarchical clustering was conducted on expression profile of 416 differentially expressed genes (DEG) and a high degree of internal consistency was discovered within each sample group. To discover whether M-CSCs could reflect the clinical metastatic process, we computed the fold-change of these genes in metastatic and non-metastatic tumors from The Cancer Genome Atlas (TCGA) ovarian cancer RNA-seq data. To quantify the consistence, we conduct the Gene Set Enrichment Analysis of DEG in M-CSCs samples against the ranked gene list (from up- to down-regulated) in TCGA ovarian metastatic tumors.

Flow Cytometry

Cultured adherent cells or tumor spheroids were detached with 2 mM EDTA PBS, suspended in PBS and counted. Cells were incubated with primary antibodies, selectin-Fc chimeras (5 µg mL$^{-1}$ in 1 mM CaCl$_2$, 1 mM MgCl$_2$, PBS binding buffer) or isotype control per the manufacturer's instructions. The primary antibody or recombinant protein were stained with appropriate Alexa Fluor 488 secondary antibodies. Events were collected on FACS AriaIII (BD Biosciences). Data were analyzed using FlowJo software (Tree Star Inc.) with gating strategy shown in FIG. 24.

Microfluidics CSCs Perfusion Assay

Microfluidic chips were fabricated as described[13]. To coat microfluidic channels with selectin recombinant proteins, channels were incubated with 1 µg mL$^{-1}$ selectin-Fc recombinant proteins in PBS at 4° C. overnight. To coat microfluidic channels with HPMCs, channels were incubated with 10 µg mL$^{-1}$ human fibronectin in serum free medium overnight at 4° C. After wash, the channels were introduced with HPMCs suspension (3.5×10$^6$ mL$^{-1}$) and cultured overnight under C02 incubator at 37° C. To functionally block selectins, HPMCs were incubated with 20 µg mL$^{-1}$ anti-E-selectin, anti-P-selectin, anti-L-selectin or isotype antibody at room temperature for 1 h before the assays.

CSCs of 70-100 µm diameter were collected with cell strainer, fluorescently labeled with CMFDA Celltracker (2.5 µg mL$^{-1}$, C7025, Life Technologies) as per manufacturer's instructions for assays. Fluorescently labeled CSCs resuspended in binding buffer (1500 spheroids mL$^{-1}$) were perfused into the microfluidic channel through a syringe pump (LongerPump) under desired shear stresses. The viscosity of the binding buffer (0.9 cp) is within the range of viscosity (0.95±0.15 cp) of ascitic fluid in patients with various ascitic etiologies[48]. The motion of cancer spheroids was observed under fluorescent microscope (Nikon ECLIPSE Ti) and serial time lapse images (1 image sec$^{-1}$) were captured for 30 sec. More than three randomly chosen areas (4× objective) were captured for each treatment.

The motion of cancer spheroids under flow was analyzed offline using Image J (National Institutes of Health) and used for the classification of interactions as described[49]. Briefly, cancer spheroids that tethered to the surface, then detached in the flow were defined as tethering. Cancer spheroids that moved at a velocity below the hydrodynamic velocity for more than one spheroid diameter were defined as rolling. Cancer spheroids that remained stationary for more than one frame during recording were determined as adhesion. Percentage of tethering or adhesion was calculated by dividing the number of tethering or adherent spheroids by the total number of spheroids flew through the field of observation in the 30 sec duration.

In some experiments, M-CSCs were incubated with or without neuramidase (100 mU, N2876, Sigma-Aldrich), α1-3,4 fucosidase (150 mU, P0769S, New England Bio-Labs), OSGE (100 µg mL$^{-1}$, CLE100, Cedarlane) or PNGase (10 U mL$^{-1}$, P0704S, New England BioLabs) according to the manufacturer's instructions for 1 h at 37° C. prior staining. To inhibit sulfation, M-CSCs were incubated with sodium chlorate (25 mM, 403016, Sigma-Aldrich) in serum-free medium for 48 h. To functionally block sLe$^x$, $sLe^a$ or IGF-1R on M-CSCs, M-CSCs were incubated with CSLEX-1 (10 μg mL$^{-1}$, 551344, BD Biosciences), anti-CA19-9 (10 μg mL$^{-1}$, ab15146, Abcam), anti-IGF-1R (2 μg mL$^{-1}$, 24-60, Invitrogen) or isotype antibodies for 1 h at 37° C., respectively. To remove cell surface glycoprotein, M-CSCs were incubated with Trypsin/EDTA solution (0.05%, 25300054, Gibco) for 5 min and neutralized with the complete medium. To inhibit glycolipid synthesis, M-CSCs were cultured with or without DL-PPMP (2.5 μM, sc-205655, Santa Cruz) in serum-free medium for 5 days. To test the involvement of RTKs in mediating CSCs adhesion, M-CSCs were treated with or without small molecule inhibitors as indicated in the FIG. 13 before perfusion. All CSC perfusion experiments were repeated with HPMCs isolated from at least 3 different patients.

Adhesion of Tumor Cells to the Mouse Peritoneum

M-CSCs (1×10$^7$) derived from SKOV-3 and ovarian cancer patients were fluorescently labeled with CMFDA and i.p. injected into NOD/SCID mice. To inhibit P-selectin, KF38789 (1 mg kg$^{-1}$, 2748, Tocris) or vehicle control were injected into the peritoneal cavity of mice 1 h prior to cell injection. Mice were sacrificed after 16 h and the peritoneal cavity was washed with PBS to remove non-adherent cells. Fluorescent signal from adherent tumor cells was acquired in the IVIS Spectrum and peritoneum, mesentery, and omentum were lysed with 1% NP-40 and fluorescence was measured with VICTOR (PerkinElmer).

P-Selectin Knockout Rag2 Immunodeficiency Mice

C57BL/6 Selp$^{-/-}$ (JAX #002289, The Jackson Laboratory) was crossbred with Rag2$^{-/-}$ (JAX #008449, The Jackson Laboratory) mice to generate Selp$^{+/-}$ Rag2$^{+/-}$ heterozygous offspring. The heterozygous offspring were further crossbred and to generate homozygous P-selectin wild type (Selp$^{WT}$ Rag2$^{-/-}$) and P-selectin knockout (Selp$^{-/-}$ Rag2$^{-/-}$) mice which were verified and selected with genotyping in the Jackson Lab. PCR genotyping of the Selp and Rag2 mutant was conducted with primers described in FIG. 14. The homozygous strains were maintained by breeding between the mice with the same genotypes respectively. SKOV-3 M-CSCs were orthotopically inoculated (3×10$^6$) or i.p. injected (5×10$^6$) into Selp$^{WT}$Rag2$^{-/-}$ or Selp$^{-/-}$ Rag2$^{-/-}$ mice (female, 6-8 weeks of age) and tumor metastatic progression was monitored as described.

Western Blot

Proteins (20 μg) were resolved on SDS-polyacrylamide gels and transferred to the nitrocellulose membrane (Bio-Rad). Target proteins were detected using specific primary antibodies overnight at 4° C. The primary antibodies were detected with appropriate horseradish peroxidase conjugated secondary antibodies and visualized with enhanced chemiluminescence (PerkinElmer). Scans of the full blots are shown in FIG. 25.

Pull Down Assay

M-CSCs were lysed in ice cold lysis buffer (50 mM Tris pH 7.4, 150 mM NaCl, 1 mM CaCl$_2$, and 1% Triton X-100, and protease inhibitors cocktail (phosphatase inhibitors 1 mM Na$_3$VO$_4$, 1 mM NaF and protease inhibitors 1 μg mL$^{-1}$ pepstatin, 2 μg mL$^{-1}$ leupeptin, 4 μg mL$^{-1}$ aprotinin, 20 μg mL$^{-1}$ PMSF)). 1 mg of cell lysate was precleared with 40 μL of Protein A/G Agarose beads for 1 h at 4° C. with agitation. Precleared lysate was incubated with 2 μg Fc or P-selectin-Fc chimera and 20 μl per tube Protein A/G agarose beads at 4° C. overnight with agitation. Precipitated beads were collected and washed with ice-cold lysis buffer. The P-selectin-Fc interacting proteins were eluted with elution buffer (50 mM Tris pH 7.4, 10 mM EDTA, 0.1% Triton, protease inhibitors cocktail) on ice for 5 min. The eluate was collected and denatured by boiling with laemmli sample buffer for 10 min. Interaction of IGF-1R with P-selectin was detected by Western blot.

Immunoprecipitation

Extracellular protein was extracted with 2 mM EDTA, 150 mM NaCl, 1% NP40, 50 mM Tris pH 7.4, and protease inhibitor cocktail. Anti-IGF-1R (sc-463, Santa Cruz Biotechnology) was immobilized on cyanogen bromide (CNBr)-activated sepharose (GE Healthcare) according to manufacturer's instruction. CNBr-activated sepharose without coupling antibody was used as a negative control. Cell lysates were precleared with CNBr-activated sepharose for 2 h followed by overnight incubation with anti-IGF-1R or isotype control conjugated beads at 4° C. The immunoprecipitates were washed with ice-cold lysis buffer and eluted with 0.1% TFA and neutralized with 1 M Tris pH 8.8. The modification of $sLe^{a/x}$ on IGF-1R was detected via Western blot.

Histological Analysis

Tissues were fixed in 4% paraformaldehyde, embedded in paraffin and stained with hematoxylin and eosin. Immunohistochemistry detection was conducted on 5 μm formalin-fixed, paraffin-embedded human omentum tissue section collected form patients with nonmalignant disorders. Heat-induced antigen retrieval was conducted in pH 6.0 sodium citrate buffer. Monoclonal mouse anti-E-selectin, anti-P-selectin and anti-L-selectin antibodies were used at 1:50 dilution. The streptavidin-biotin immunoperoxidase Histostain SP Bulk kit (Invitrogen) and ImmPACT AEC peroxidase substrate kit (Vector Laboratories) were applied for detection and hematoxylin was used as the nuclear counterstain.

RNA Extraction, Reverse Transcription, and PCR

Total RNA was extracted with Trizol and 500 μg of RNA was reverse transcribed to cDNA using the first-stranded cDNA synthesis kit (Invitrogen). Specific genes were amplified and quantitated by real-time PCR using primers described in FIG. 14. Real-time PCR was performed using the StepOnePlus real-time detection system and the Power SYBR Green PCR Master Mix (Applied Biosystems). Fluorescent measurements were recorded during each annealing step. The PCR quality and specificity were verified by melting curve analysis and gel electrophoresis. Relative expression was determined by normalizing to the GAPDH endogenous control. These experiments were carried out in duplicate and independently repeated three times.

FUT5 Stable Knockdown by shRNA

Lentivirus carrying shRNA targeting FUT5 (sequence described in the FIG. 14) or nonspecific (NS) shRNA were generated by co-transfection of HEK293 cells with the constructs and lentiviral packaging plasmids (Sigma-Aldrich) per the manufacturer's instructions. M-CSCs were transduced with the viral particle containing media and cells were selected with 1 μg mL$^{-1}$ puromycin (Calbiochem) 24 h post-transduction for 3 days. The knockdown efficiency was verified by q-PCR Statistical Analysis Results represent mean±SEM. The significance of differences between categorical variables were determined using the chi-square test. Ordinal variables were assessed using the one-tailed Student's t test.

Data Availability

The RNA sequencing data have been deposited in the NCBI Trace Archive under the accession code PRJNA530706. All the other data supporting the findings of this study are available within the article and its supplementary information files or from the corresponding author upon reasonable request.

Kaplan-Meier Analysis

Progression-free survival (PFS) analysis was performed in an integrative ovarian cancer datasets[1]. Patients with advanced-stage (FIGO stage III-IV) ovarian cancer (all clinical subtypes) were divided into low- and high-expression groups according to the mRNA level of specific genes. The risk differences of two groups were estimated using the log-rank test. The cutoff point giving the most pronounced P value was selected.

Figure 1A:
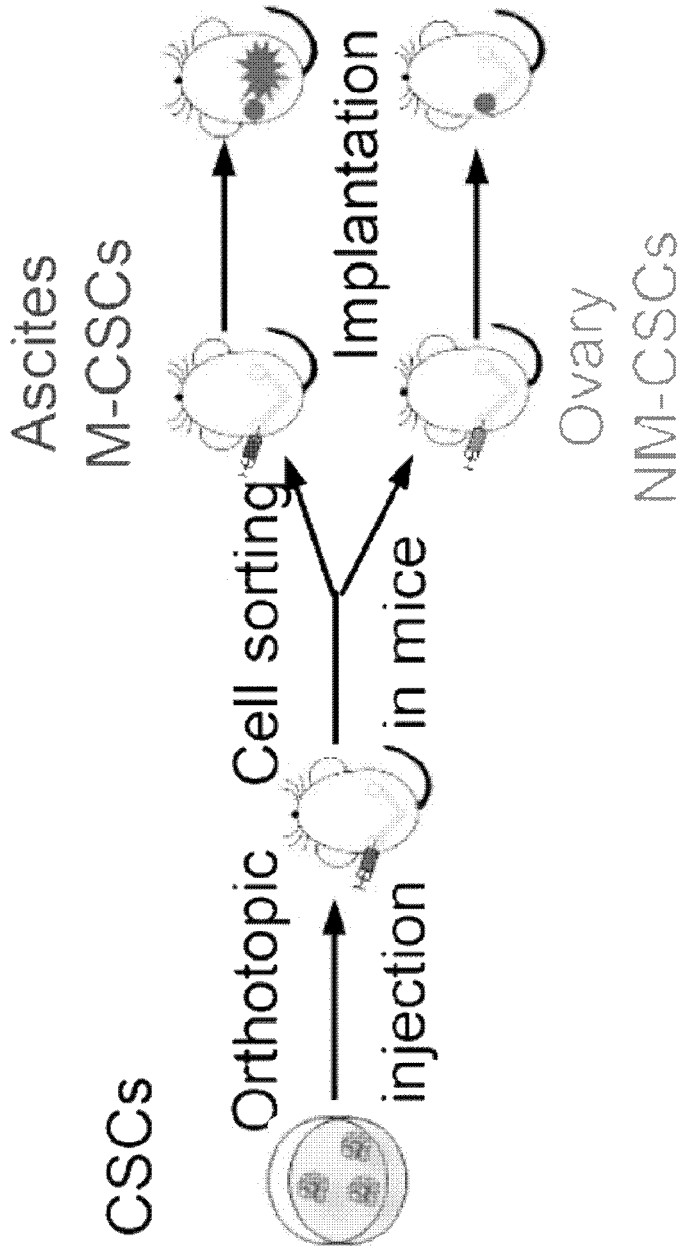
Figure 1B:
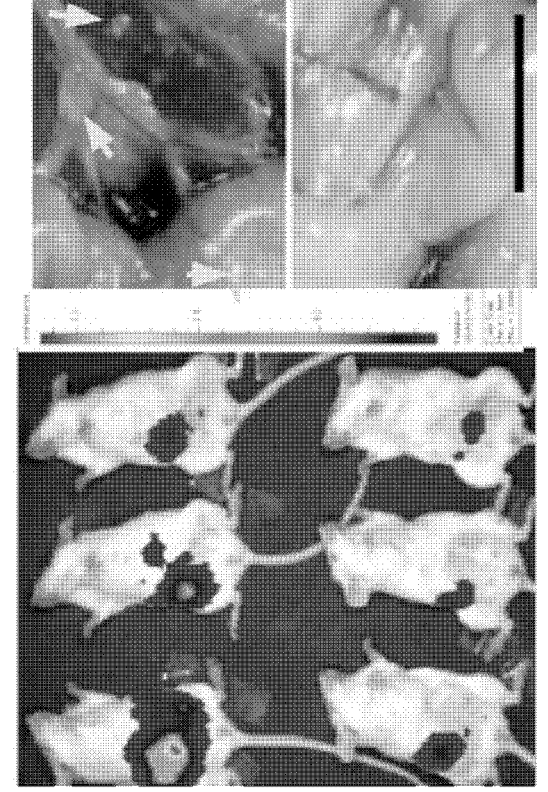
Figure 1C:
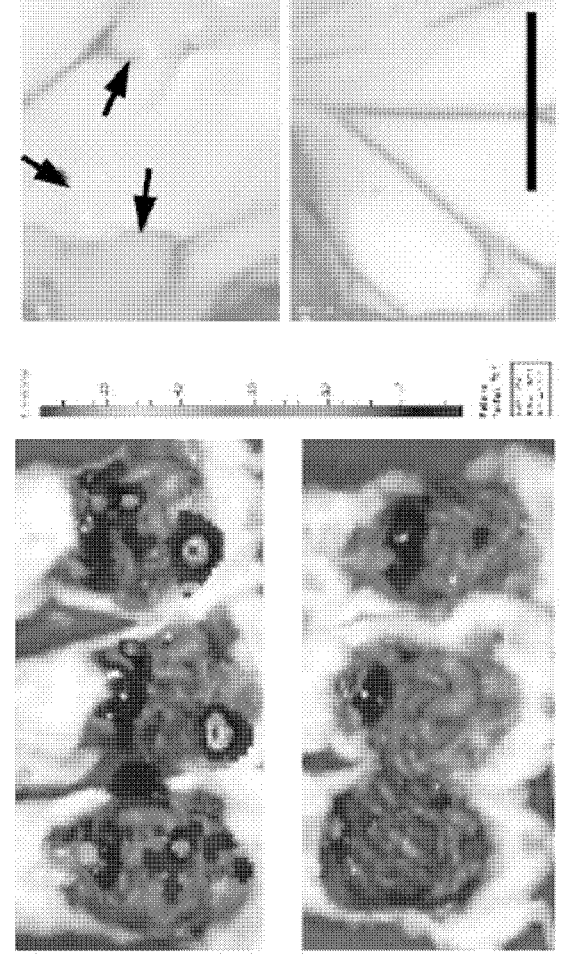
Figure 1E:
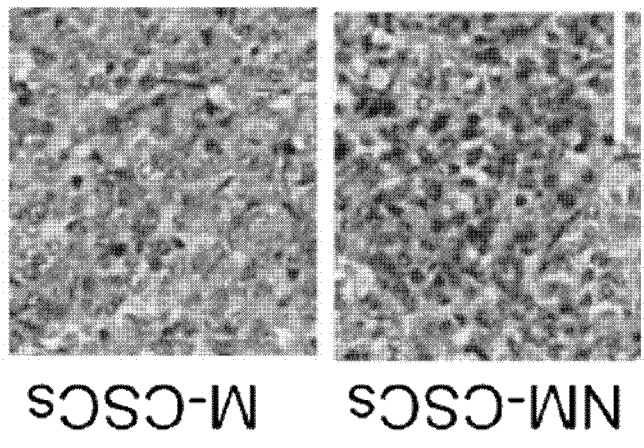
Figure 1D:
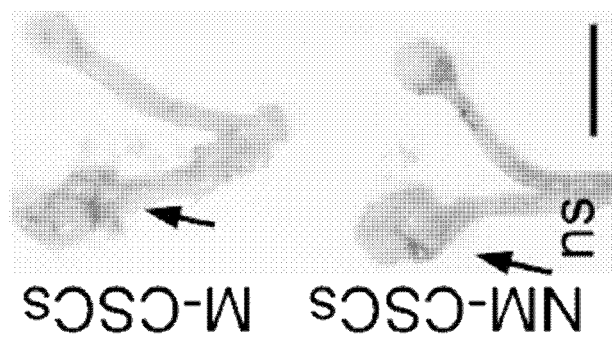
Figures 1F, 1G:
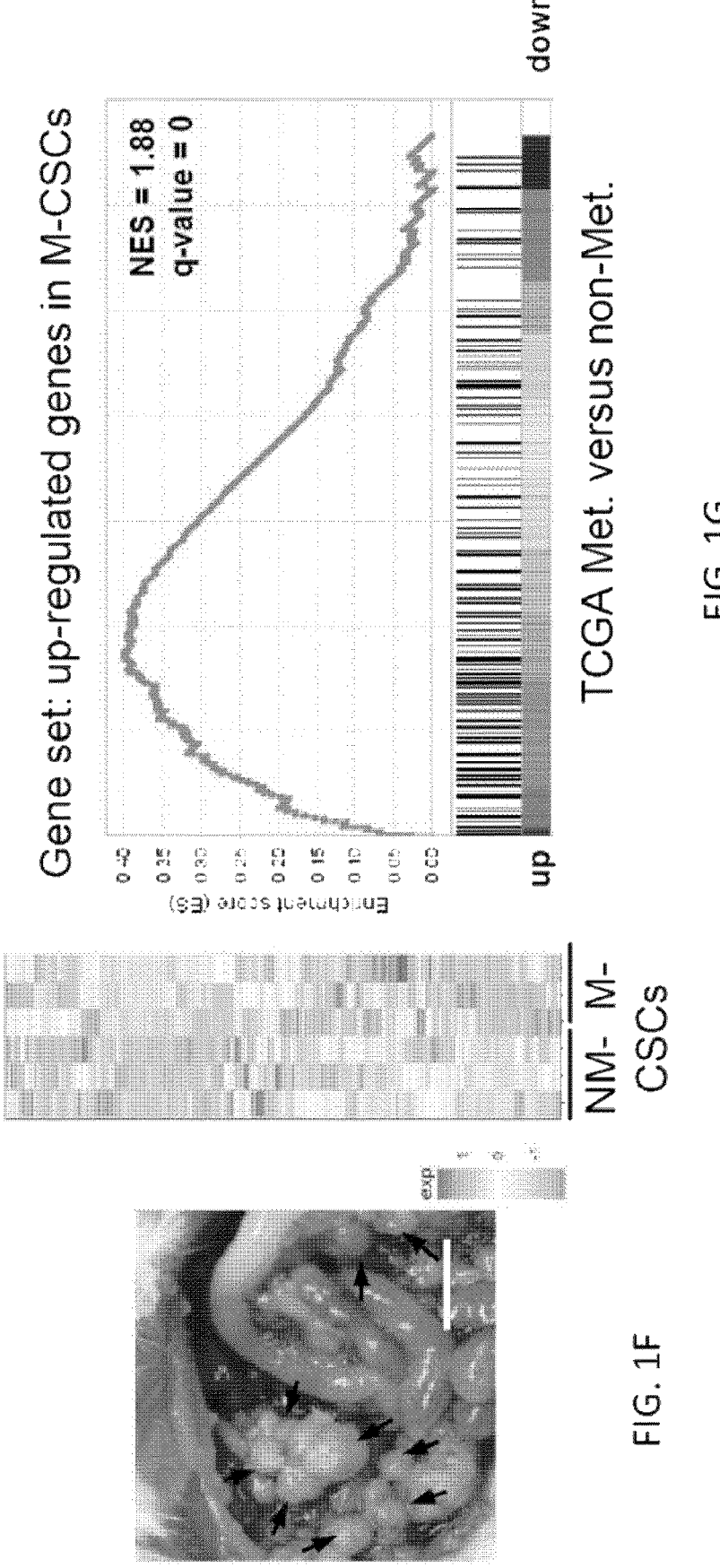

7. RESULTS 7.1 Establishment of M-/NM-CSC models. To explore the limiting factors that determine the metastatic success of ovarian cancer, we reasoned that metastatic colonization is a highly inefficient process and is accomplished by only a subset of cancer stem/tumor-initiating cells (CSCs)[3]. We have previously isolated CSCs[12]. Using in vivo selection by orthotopic implantation of CSCs into the bursa of the mouse ovary, we further isolated the highly metastatic population of CSCs (M-CSCs) in SKOV-3 (FIG. 1A), which consistently metastasized to the peritoneum, recapitulating the clinical progression of human ovarian cancer, when implanted either by orthotopic or intraperitoneal (i.p.) injection (FIG. 1B-E). Conversely, non-metastatic (NM)-CSCs, which are equally tumorigenic (FIG. 1D, E), did not metastasize in both models (FIG. 1B-E, Table 1). Similar metastatic abilities were observed in CSCs-enriched cultures generated from primary ovarian cancer samples (FIG. 1F, Table 1). Moreover, M-CSCs had a gene expression profile similar to the metastatic tumors in ovarian cancer patients (FIG. 1G), suggesting that the in vitro M-CSCs could closely reflect the spontaneous metastatic cellular events in patients. We have also derived M- and NM-CSCs from HEYA8 cells, and similar results were obtained (FIG. 17A, B).

TABLE 1

Comparison of tumorigenic and metastatic abilities

|  | NM-CSCs | M-CSCs | Patient samples |
| --- | --- | --- | --- |
| Tumorigenesis | Yes (5/5) | Yes (5/5) | Yes (7/7) |
| Metastasis | No (0/8) | Yes (8/8) | Yes (7/7) |
| Metastases (no.) | — | 39 ± 5 (orthotopic) ** 23 ± 3 (i.p.) ** | 13 ± 1 |
| Ascites volume (mL) | — | 0.5 ± 0.1 (orthotopic) ** 0.3 ± 0.1 (i.p.) ** | 3.65 ± 0.4 |

Results are represented with mean ± SEM from two independent experiments, unpaired Student's t test.
ns, not significant.
** P < 0.01.

Figure 2A:
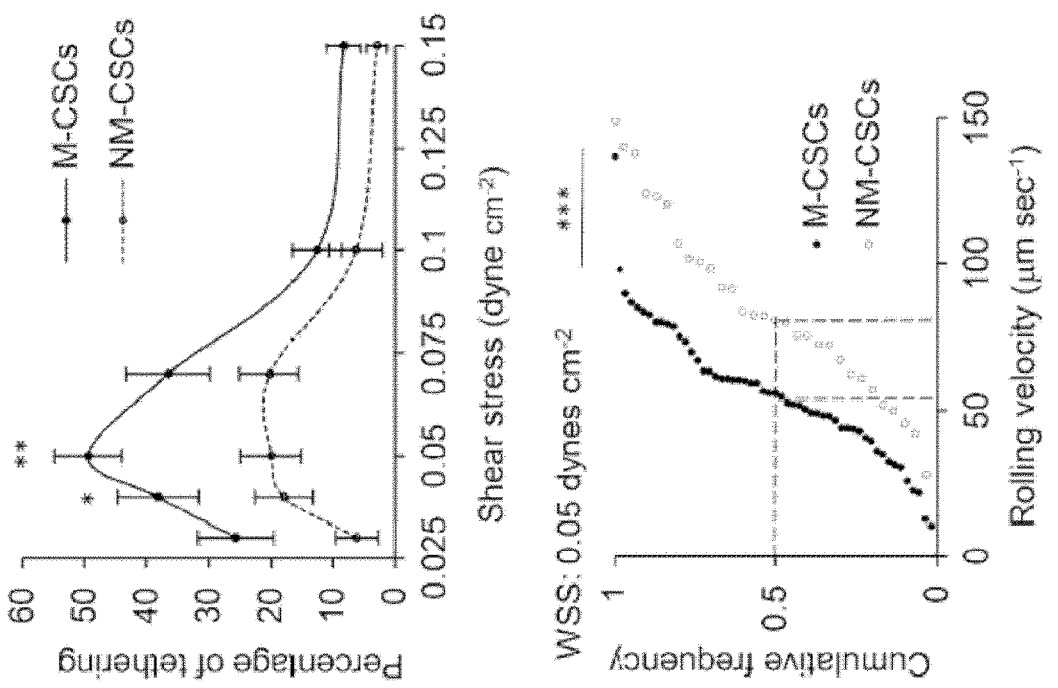
Figure 2B:
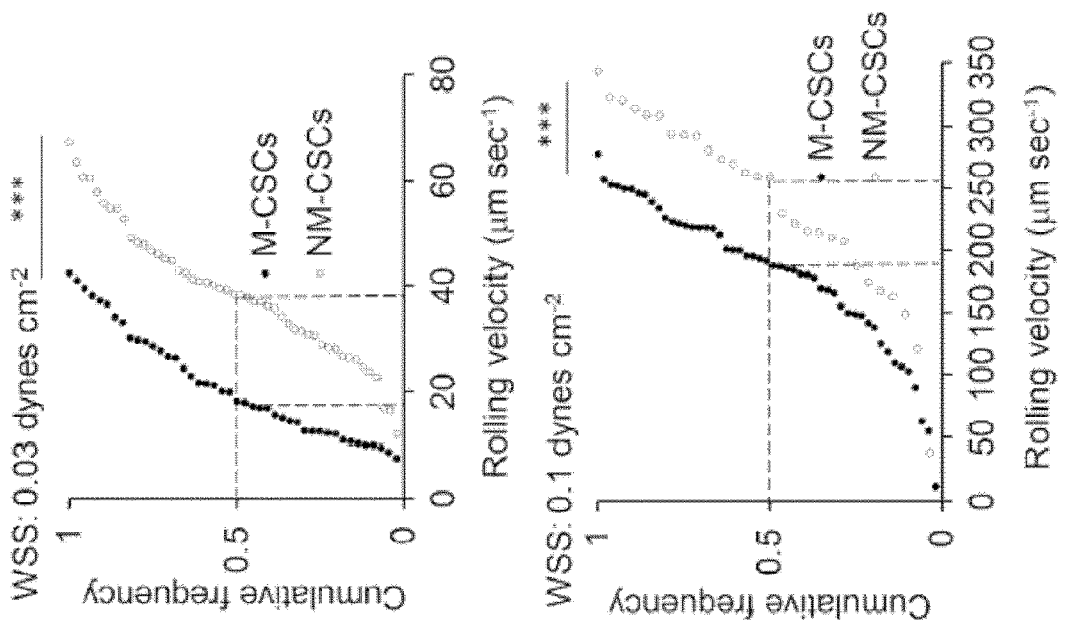
Figure 2C:
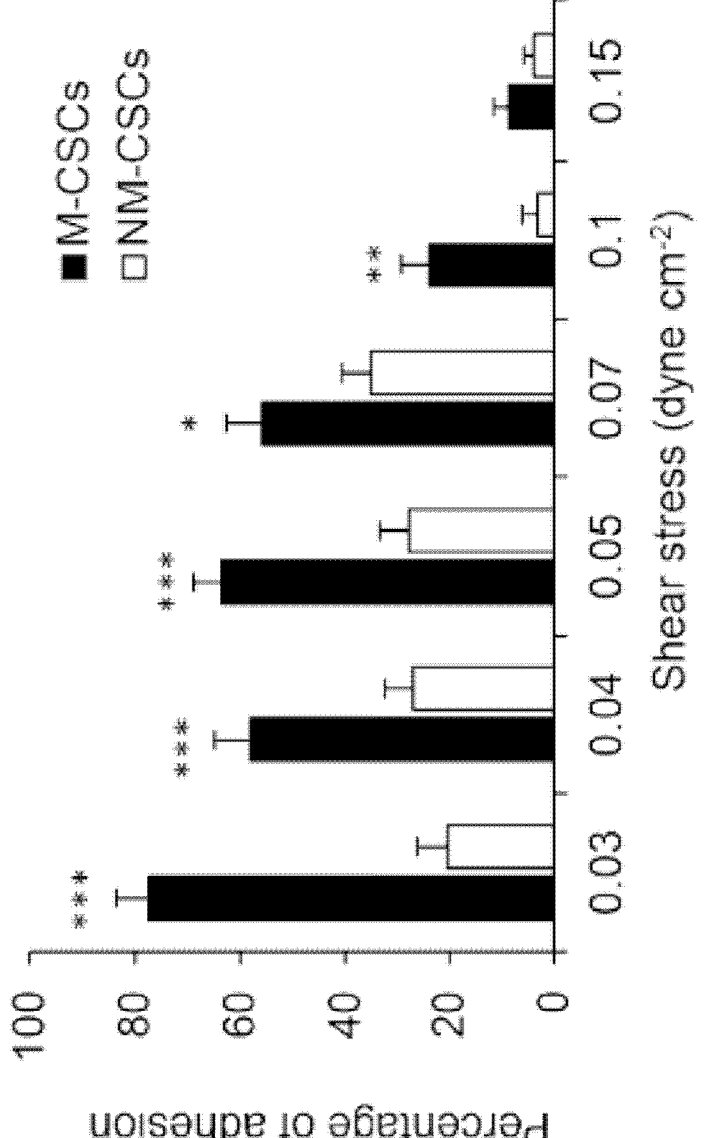

Differential capabilities in tethering, rolling and adhesion. To evaluate whether the distinct metastatic phenotypes in the two CSCs populations have different abilities in tumor-mesothelial interaction, we have developed a customizable microfluidic platform to overcome the technical limitations of the conventional approaches and to recapitulate peritoneal dissemination in dynamic flow[13]. CSCs spheroids were perfused to the microfluidic chip coated with primary human peritoneal mesothelial cells (HPMCs) under well-defined flow rate. As shown, the CSCs were effectively captured to HPMCs at 0.03-0.15 dynes $cm^{-2}$ (a physiologically relevant range of shear stress of the ascites[14]) with maximal activity at a shear stress of 0.05 dynes $cm^{-2}$ (FIG. 2A), consistent with a catch bond that requires a clear threshold shear to initiate rolling[15]. Strikingly, both the kinetic and mechanical properties that govern tumor-mesothelial interaction were significantly different between the two CSCs populations. Compared with NM-CSC, M-CSCs had a higher tethering frequency (1.8-fold at 0.05 dynes $cm^{-2}$) (FIG. 2A, FIG. 17C) and lower rolling velocity (FIG. 2B, FIG. 17D) on HPMCs, resulting in a higher percentage of firm adhesion of M-CSCs to HPMCs (2.3-fold at 0.05 dynes $cm^{-2}$) (FIG. 2C, FIG. 17E). Although HPMCs is sufficient to induce EMT in certain cell contexts[16], we showed that these cells retained their epithelial cell morphology, consisting of tightly packed colonies of cells (FIG. 18B) and N-cadherin and vimentin mRNA levels were similar between the primary culture and the later subculture (FIG. 18B).

Figures 3A, 3B:
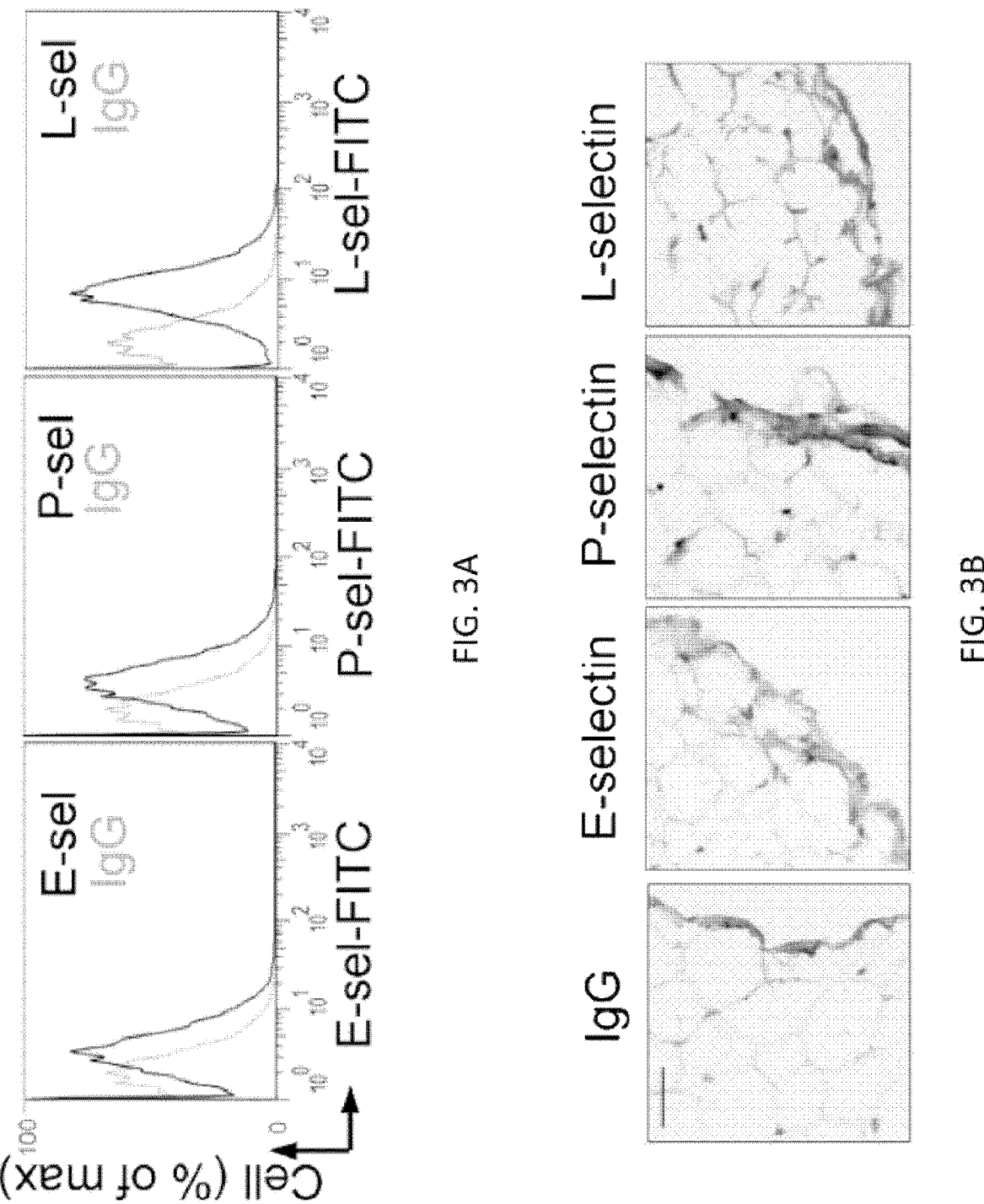
Figures 3C, 3D:
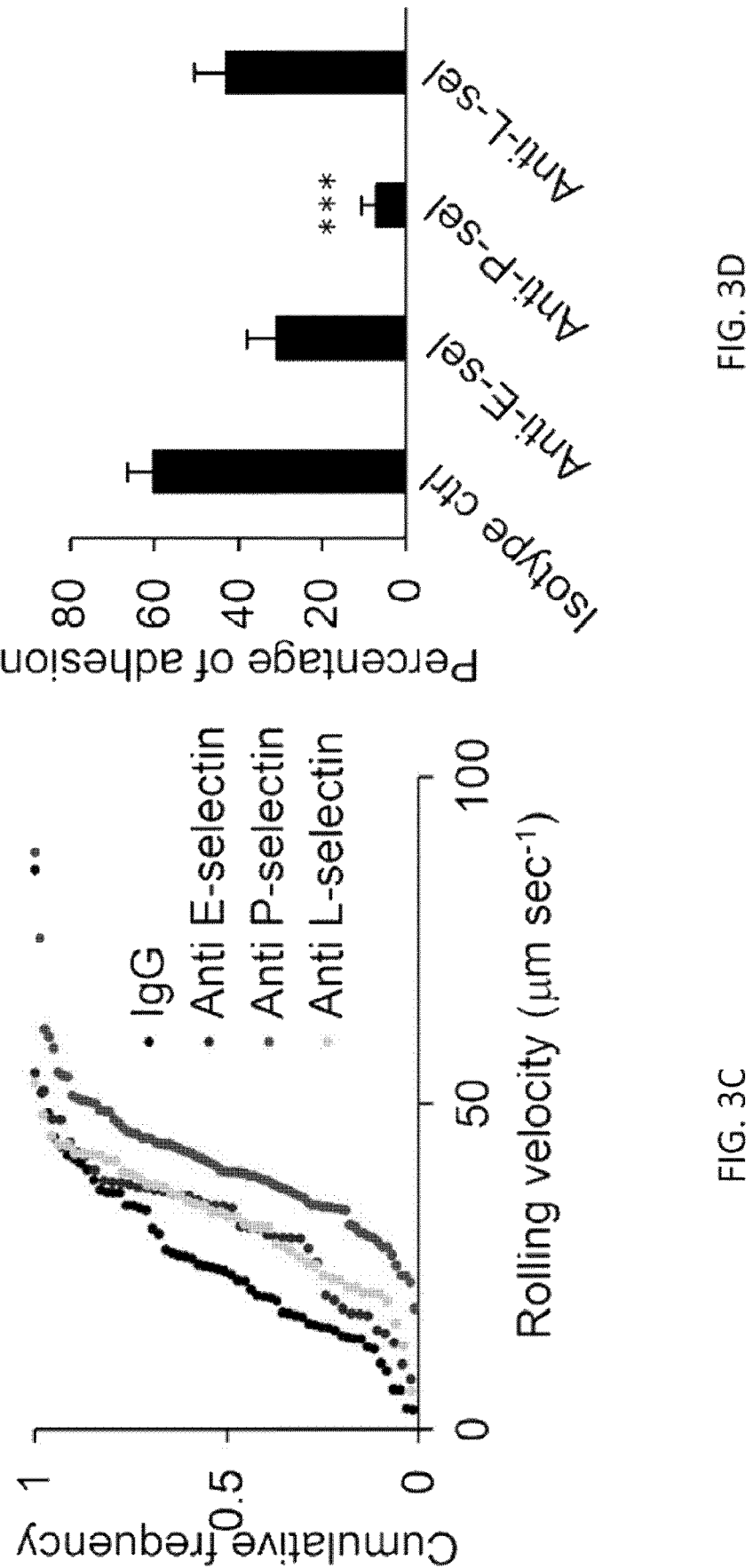
Figure 3F:
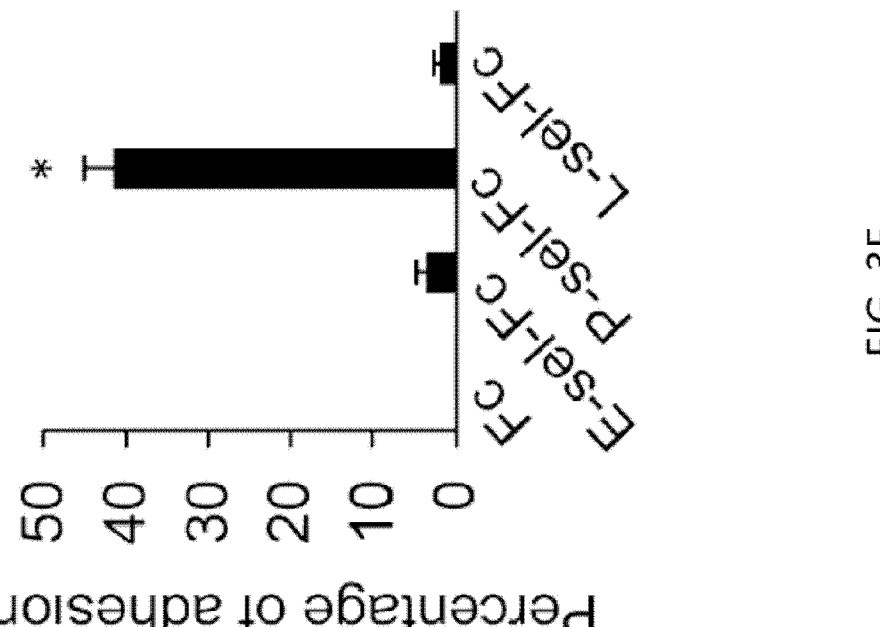
Figure 3E:
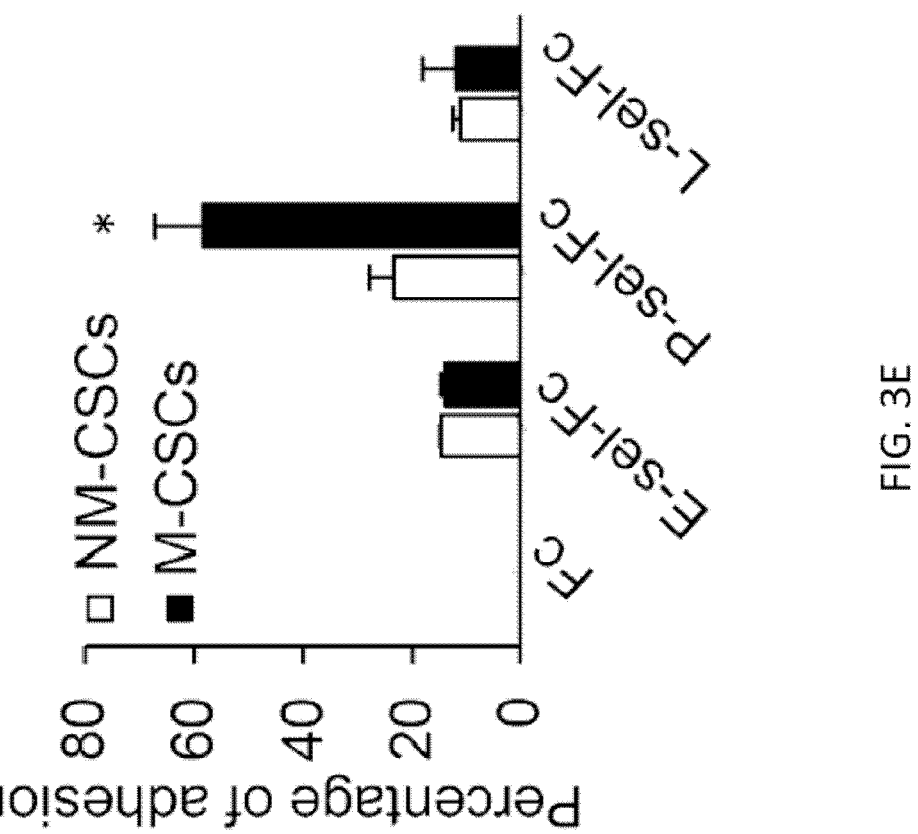
Figure 3H:
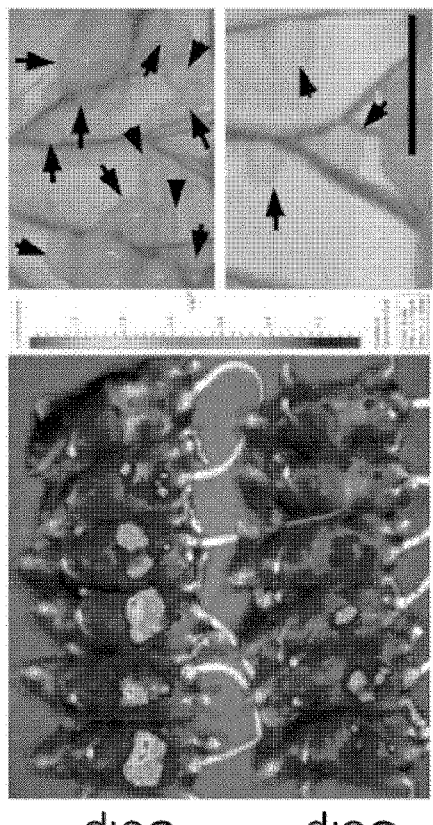
Figure 3G:
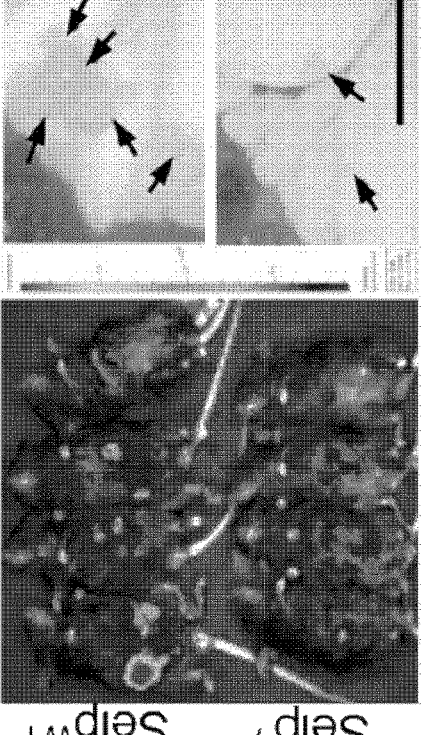
Figure 3K:
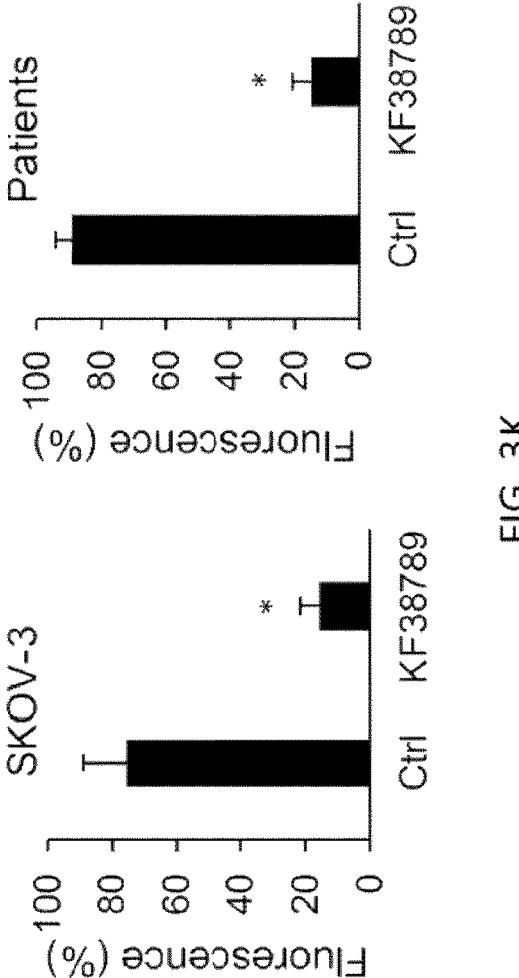
Figure 3J:
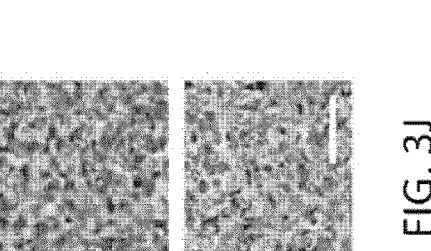
Figure 3I:

P-selectin mediates M-CSC-HPMC interaction under flow. HPMCs clearly showed constitutive cell surface expression of selectins (FIG. 3A, B). We also performed real-time PCR expression to verify the expression of E-, P- and L-selectin. Like endothelial cells, used as a reference cell population, selectins are expressed on HPMCs, suggesting that their expression outside the vasculature is present, which are consistent with previous observations[9,10] (FIG. 18C). To determine which selectin on HPMCs plays a major role in capturing M-CSCs under flow, anti-selectin blocking antibodies were used. Treatment with anti-E-, P- or L-selectin increased the rolling velocities of M-CSCs when compared with that of isotype control (24.8% increase by anti-E-selectin, 63.3% increase by anti-P-selectin, and 22.5% increase by anti-L-selectin in median rolling velocities) (FIG. 3c, FIG. 19A). Notably, blockade of P-selectin almost completely abrogated (~88%) tumor-mesothelial adhesion at 0.05 dynes $cm^{-2}$, whereas inhibition of E-selectin or L-selectin had partial effects (48% by anti-E-selectin; 28% by anti-L-selectin) (FIG. 3D, FIG. 19B). Consistently, significant adherence to P-selectin-Fc (59%), but not E-selectin- or L-selectin-Fc, was observed with M-CSCs (FIG. 3E, FIG. 19C), confirming a predominant role for P-selectin. In contrast, NM-CSCs did not show similar interactions with selectin-Fcs. We further showed that CSCs in ovarian cancer patients' ascites utilized P-selectin-dependent binding as observed in M-CSCs, since tumor spheroids isolated from ascites rolled and adhered onto the P-selectin-Fc but not Fc control (FIG. 3F). The P-selectin-Fc-mediated binding was shear-resistant and $Ca^{2+}$-dependent. Once the M-CSCs had adhered to the HPMCs, the bonding between M-CSCs and HPMCs was strong that the M-CSCs can only be completely dissociated when a maximal shear stress of 4 dynes $cm^{-2}$ was applied (FIG. 20A). Treatment of M-CSCs with EDTA inhibited the adhesion of M-CSCs to HPMC (FIG. 20B) and could easily detach the adherent M-CSCs from the HMPCs and P-selectin chimera, even at shear stress around 1 dynes $cm^{-2}$ (FIG. 20C).

Figures 4A, 4B:
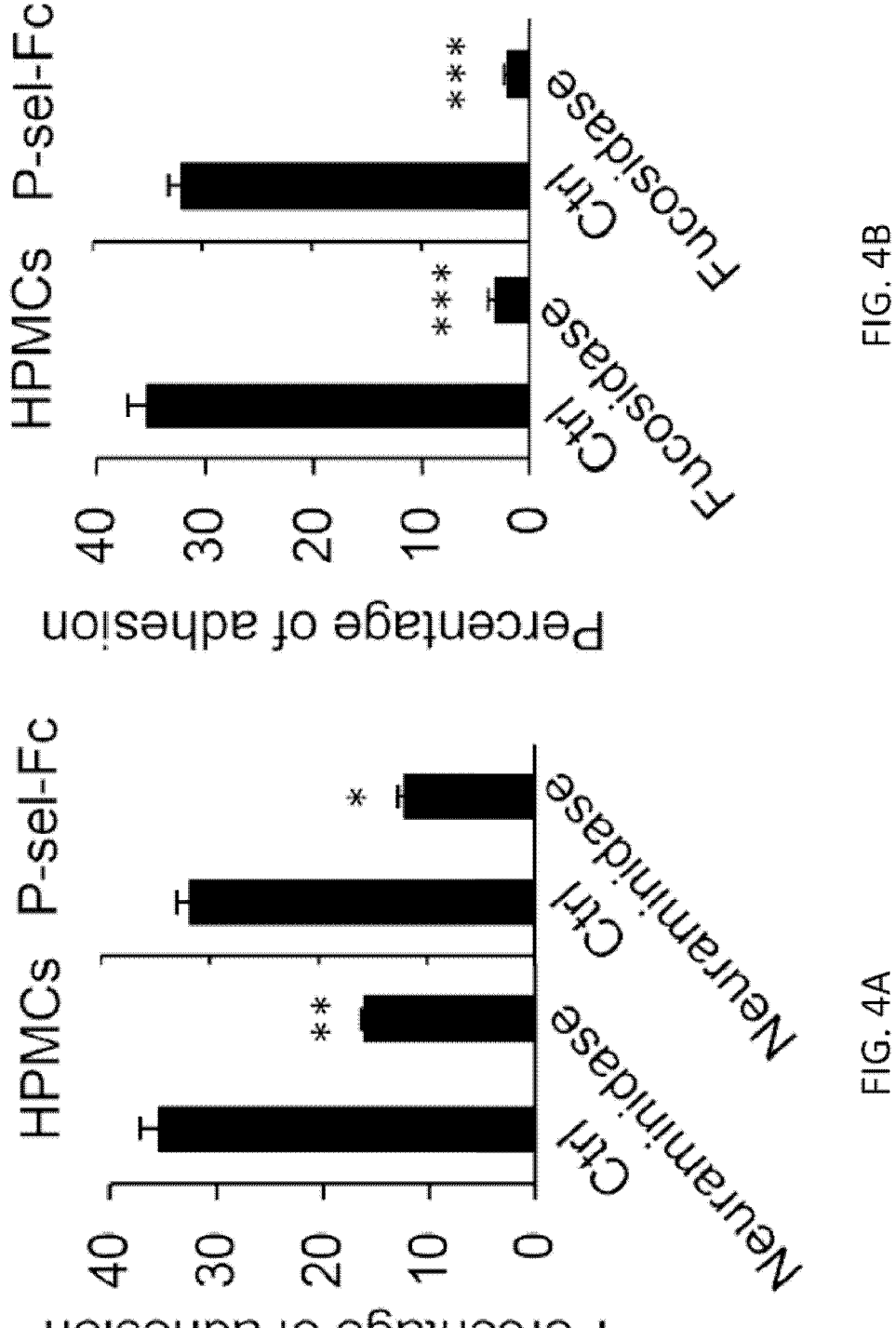
Figures 4C, 4D:
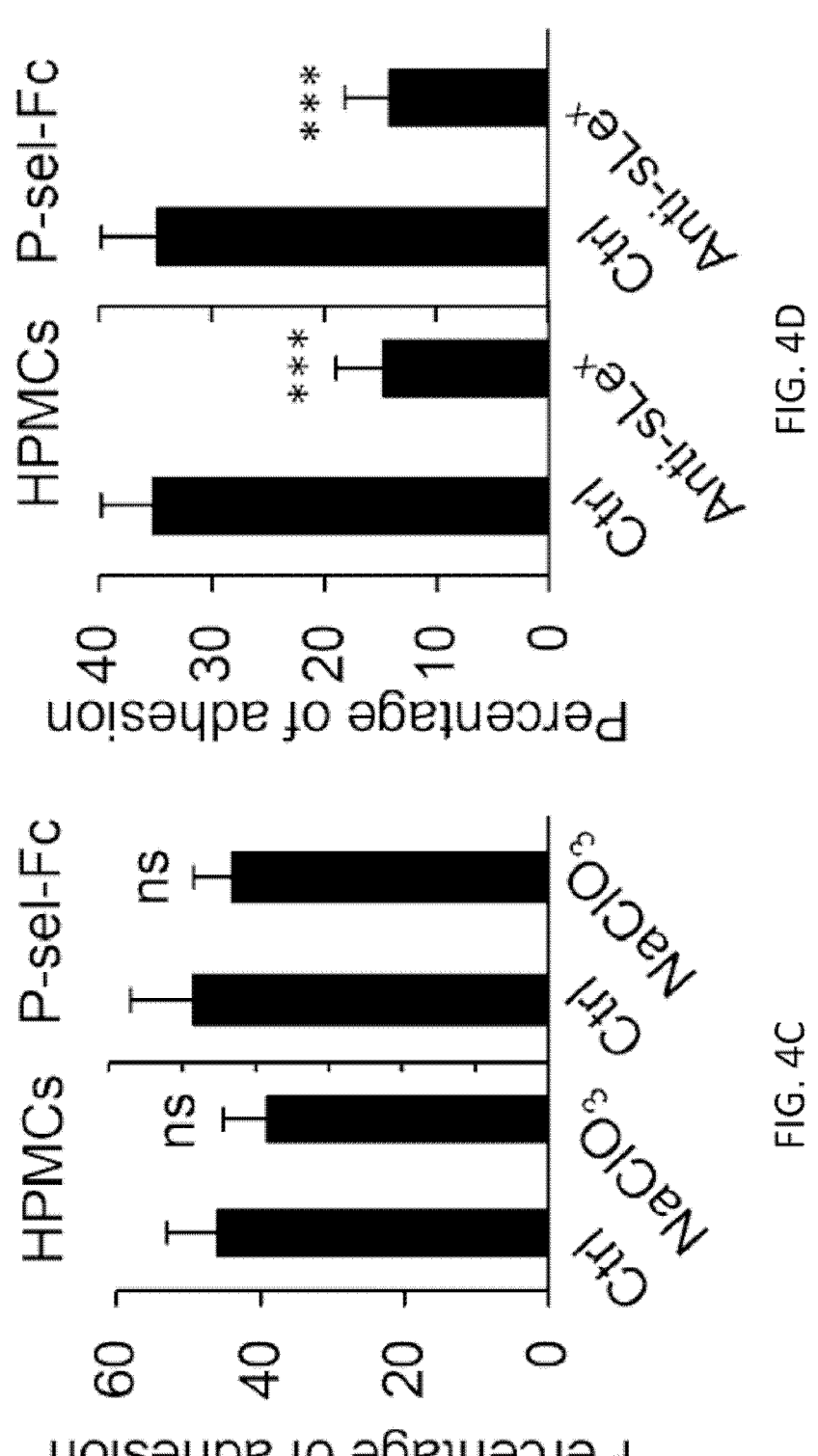
Figures 4E, 4F:
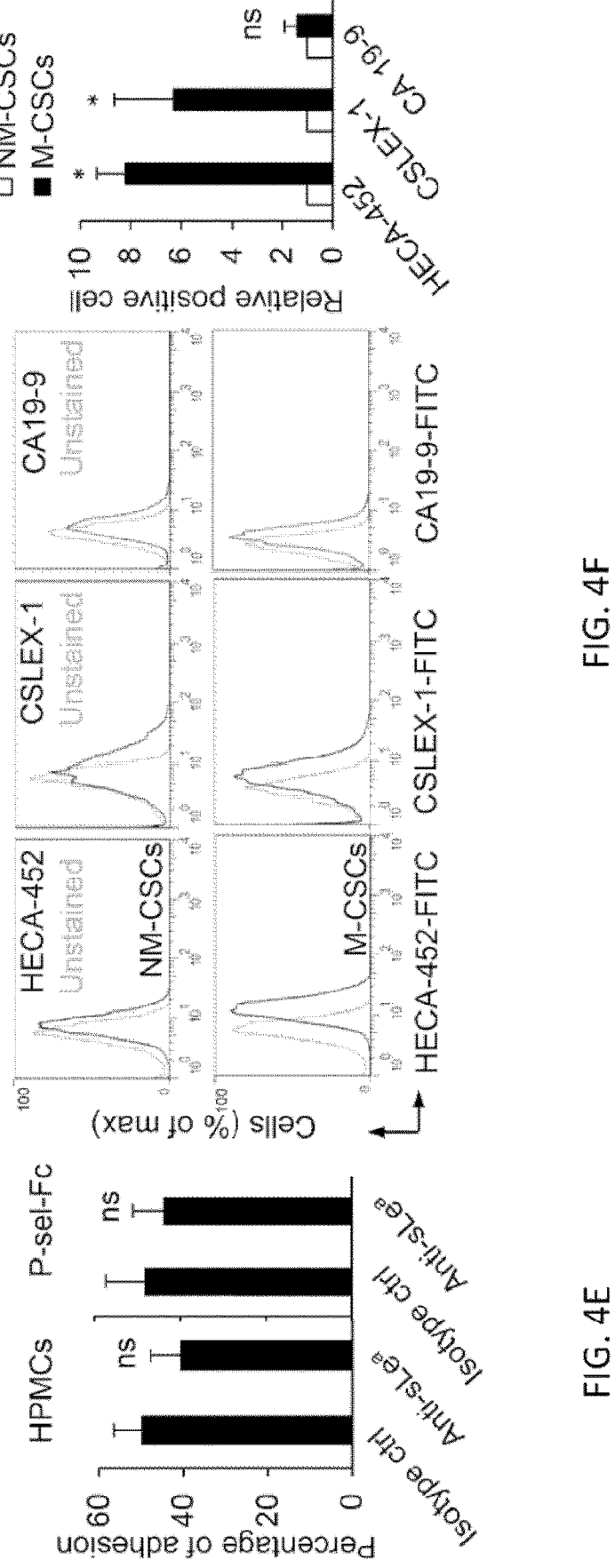
Figures 4G, 4H, 4I, 4J:
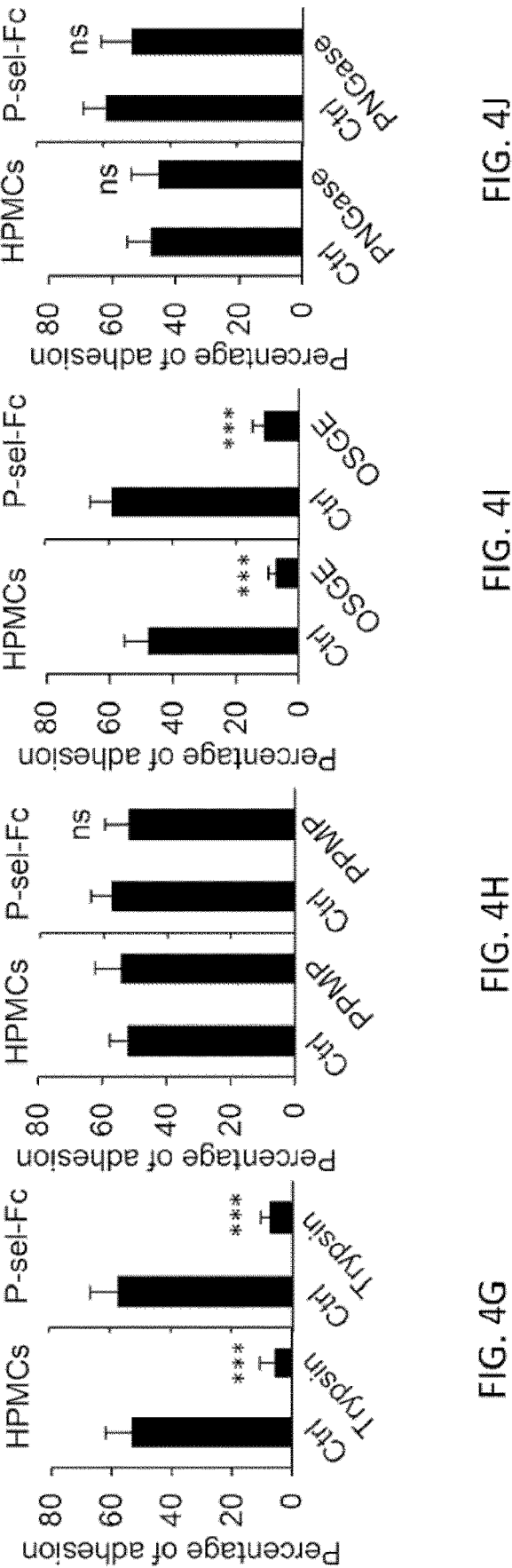
Figure 5A:
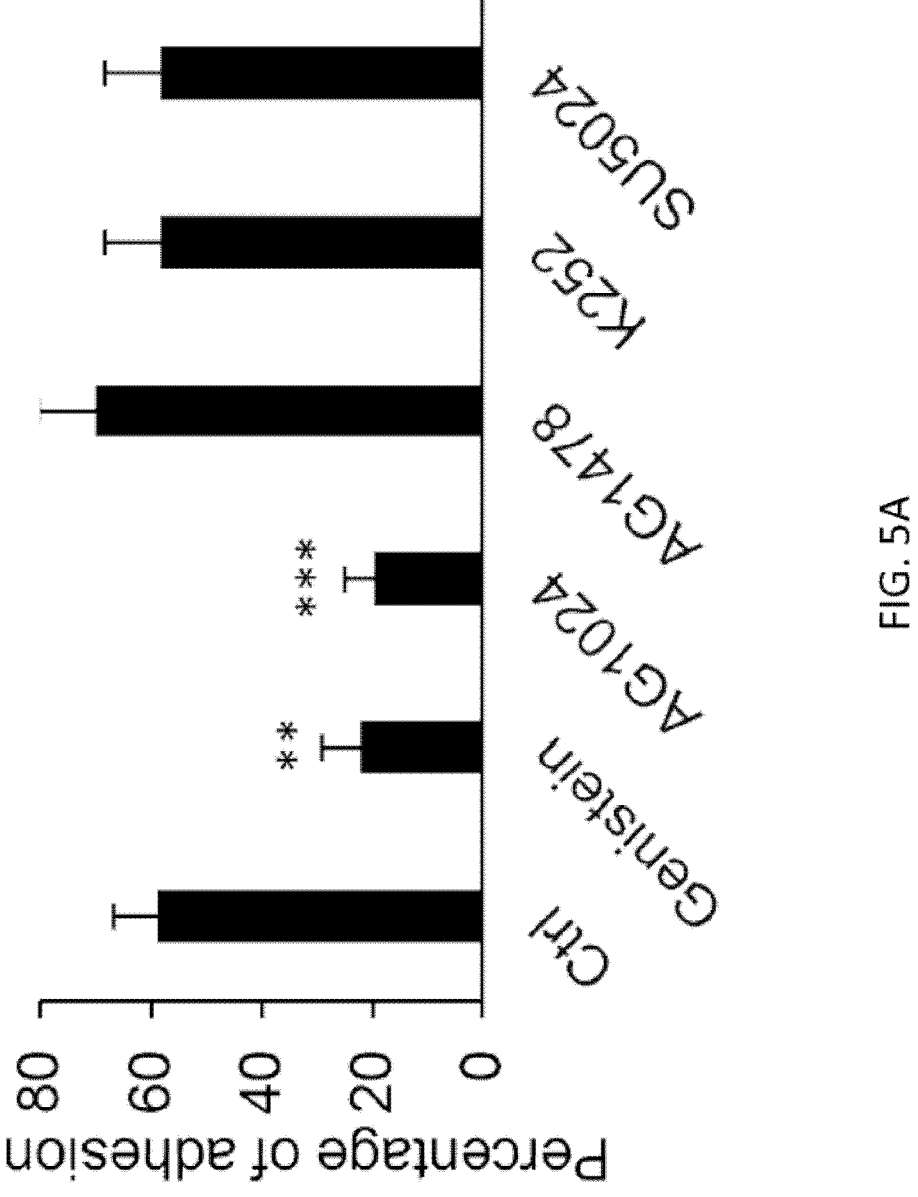
Figure 5B:
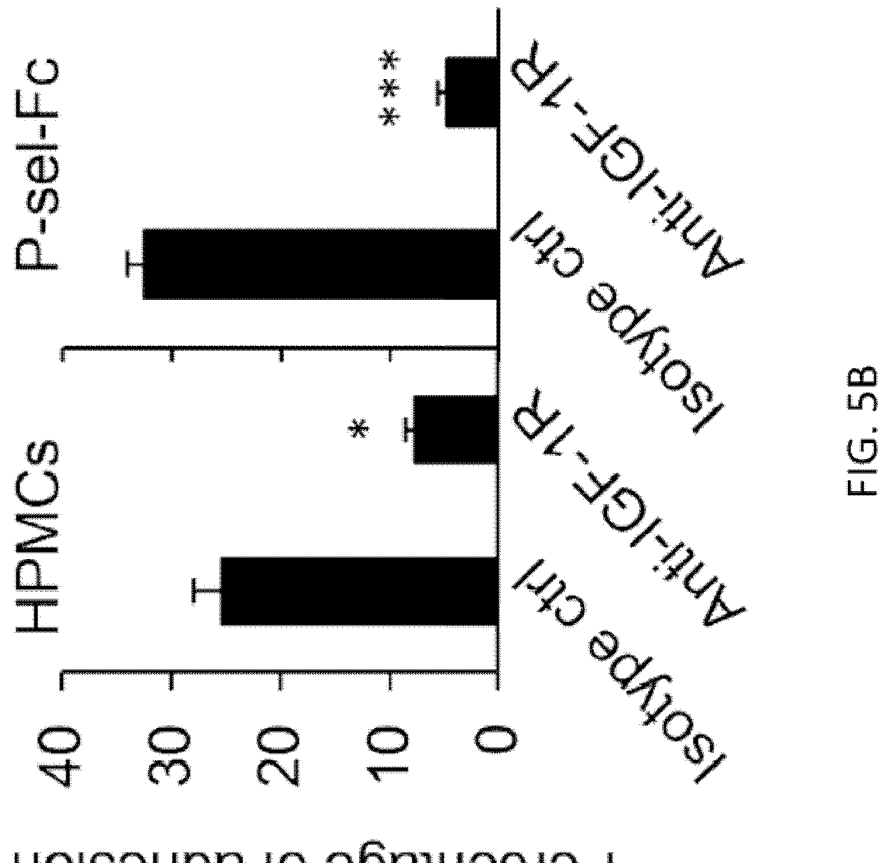
Figures 5C, 5D:
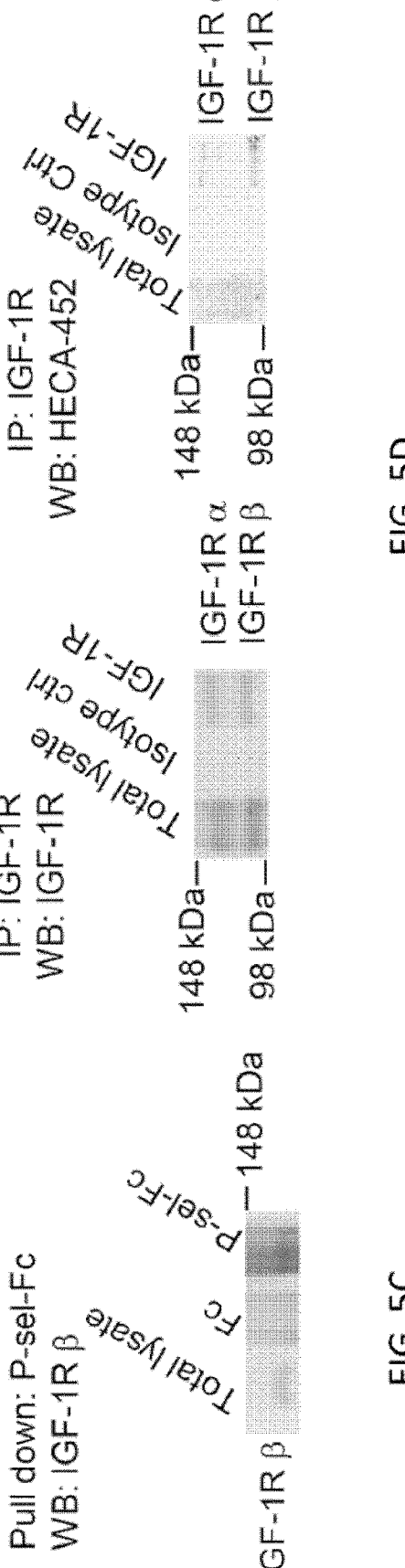
Figure 5F:
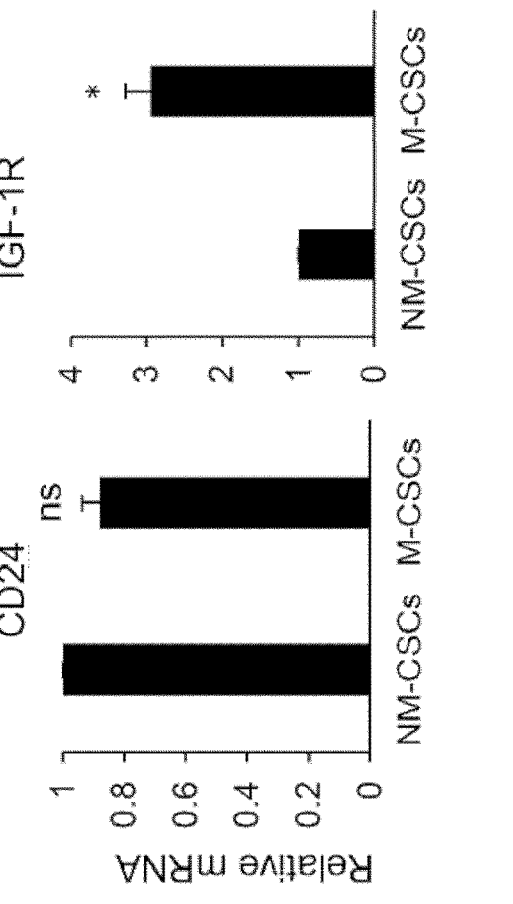
Figure 5E:
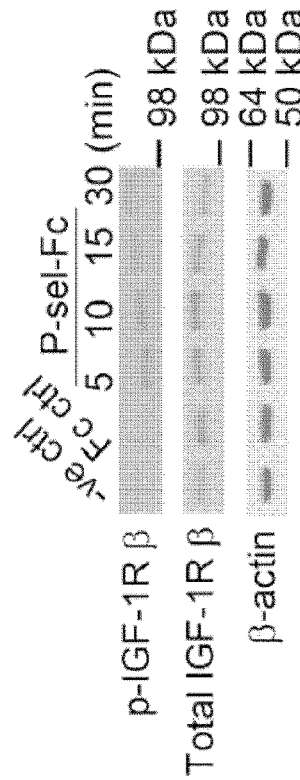

P-selectin is required for peritoneal metastasis in vivo. Next, we took advantage of the $Selp^{-/-}$ $Rag2^{-/-}$ mice to study the requirement of P-selectin in intraperitoneal metastasis of M-CSCs. In mice with wildtype P-selectin ($Selp^{WT}$ $Rag2^{-/-}$), M-CSCs quickly disseminated throughout the peritoneal cavity after orthotopic or i.p. injection (FIG. 3G, H) with visible tumor nodules growing on the omentum, mesenteries and small bowels (FIG. 3G, H) and developed massive ascites (FIG. 15). In contrast, the metastatic progression was markedly reduced in $Selp^{-/-}$ $Rag2^{-/-}$ mice (FIG. 3G, H) with no significant difference in primary tumor growth (FIG. 3, J). To further confirm the role of P-selectin and to explore whether therapeutic agent against P-selectin is able to eliminate tumor-mesothelium adhesion, we tested KF38789, a selective inhibitor of P-selectin-mediated cell-cell adhesion in vivo. Concurrent with the above results, KF38789 significantly inhibited the extent of tumor metastases on the omentum, mesenteries and peritoneal wall when treated 1 h prior to the injection of M-CSCs derived from both SKOV-3 and ovarian cancer patients (FIG. 3K), confirming the specific role for P-selectin in mediating M-CSCs adhesion.

sLe$^x$ on an O-glycoprotein is P-selectin ligand on M-CSCs. Sialylation, fucosylation, and sulfation are the main features of P-selectin ligands[17]. As shown, the removal of sialic acid with neuraminidase reduced M-CSCs binding to HPMCs or P-selectin-Fc by ~50% (FIG. 4A). Notably, almost completely abolished M-CSCs binding to HPMCs or P-selectin-Fc was observed upon the removal of fucose with fucosidase (FIG. 4B), whereas inhibition of sulfation by sodium chlorate did not alter the binding activity (FIG. 4C), indicating that the binding between M-CSCs and HPMCs or P-selectin-Fc is highly fucosylation- and relatively weaker sialyation-, but not sulfation-dependent. We next examined the involvement of fucosylated and sialylated glycans, sLe$^x$ or sLe$^a$, in mediating M-CSCs adhesion. As shown in FIGS. 4D and E, preincubation of M-CSCs with anti-sLe$^x$ blocking antibody reduced binding of M-CSCs to HPMCs or P-selectin-Fc, whereas anti-sLe$^a$ blocking antibody did not affect the interaction. By flow cytometry, while M-CSCs, but not NM-CSCs, displayed reactivity of HECA-452 and CSLEX-1, which recognizes sLe$^{a/x}$ and sLe$^x$ respectively, they showed no difference on anti-sLe$^a$ (CA19-9) expression (FIG. 4F, FIG. 21). We further found sLe$^x$-containing glycan is modified on a protein but not a lipid, since protease (trypsin) treatment on M-CSCs almost completely abolished the adhesion of M-CSCs on both HPMCs and P-selectin-Fc (FIG. 4G), whereas glycolipid synthesis inhibitor (PPMP) treatment had no effect (FIG. 4H). Treatment of O-sialoglycoprotein endopeptidase (OSGE) substantially reduced the adhesion of M-CSCs on both HPMCs and P-selectin-Fc (FIG. 4I), whereas treatment of Peptide:N-glycosidase F (PNGase) for removal of N-glycans had no effect (FIG. 4J). P-selectin ligand on M-CSCs is mainly conferred by IGF-1R. To identify the protein presenting the sLe$^x$ on M-CSCs that mediates the P-selectin interaction on HPMCs, we examined a set of inhibitors at effective concentrations that specifically target various cell surface receptor tyrosine kinase (RTK), including c-Met, EGFR, FGFR, and IGF-1R, which have been previously implicated in the progression of ovarian cancer[18-21]. We found that only genistein (general RTK inhibitor) and AG1024 (IGF-1R inhibitor) led to a marked decrease in the binding of M-CSCs to HPMCs or P-selectin-Fc (FIG. 5A, FIG. 22). Moreover, blockade of M-CSCs adhesion on HPMCs or P-selectin-Fc binding was observed with the anti-IGF-1R (FIG. 5B). Furthermore, endogenous IGF-1R could be readily detected in the P-selectin-Fc immunoprecipitate (FIG. 5C). Significant amount of sLe$^x$ was detected in both IGF-1R subunits (FIG. 5D). The levels of phospho-IGF-1R was elevated soon upon P-selectin-Fc binding (FIG. 5E). These experiments were all performed in the absence of IGF-1, suggesting a ligand-independent activation of IGF-1R upon P-selectin binding. The known P-selectin ligands bearing sLe$^x$, such as CD24, was detected. However, unlike IGF-1R, there was no differential expression of CD24 between M-CSCs and NM-CSCs (FIG. 5F).

Figure 6A:
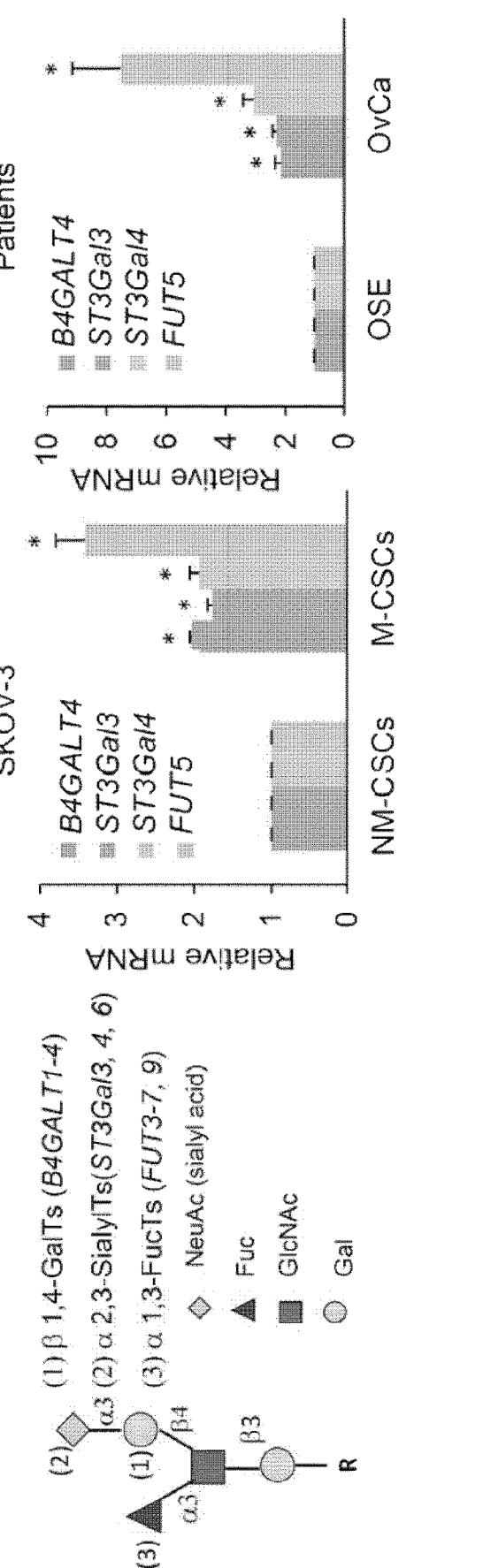
Figure 6B:
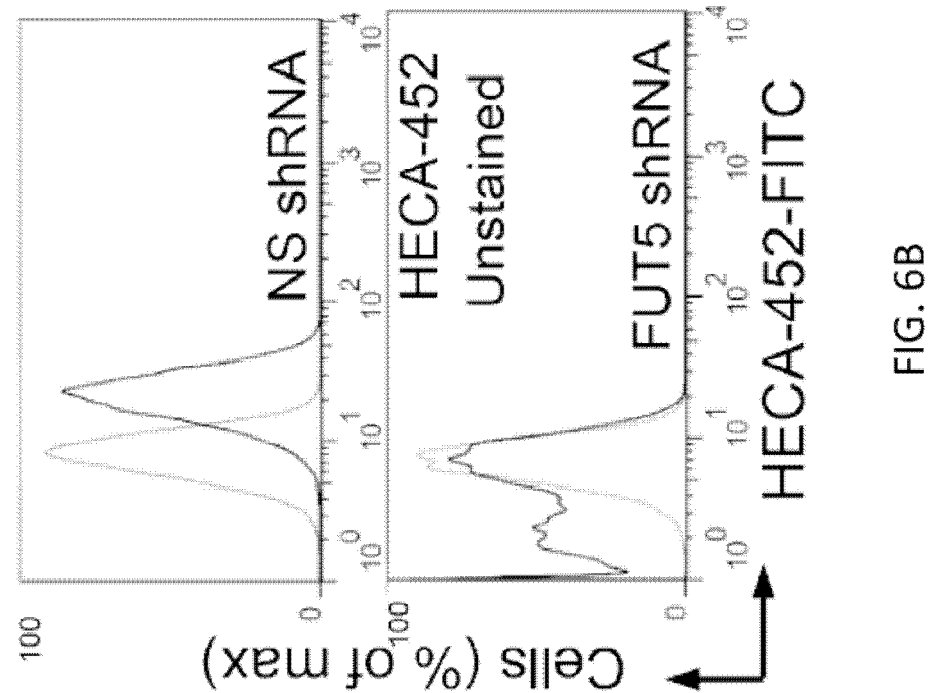
Figure 6D:
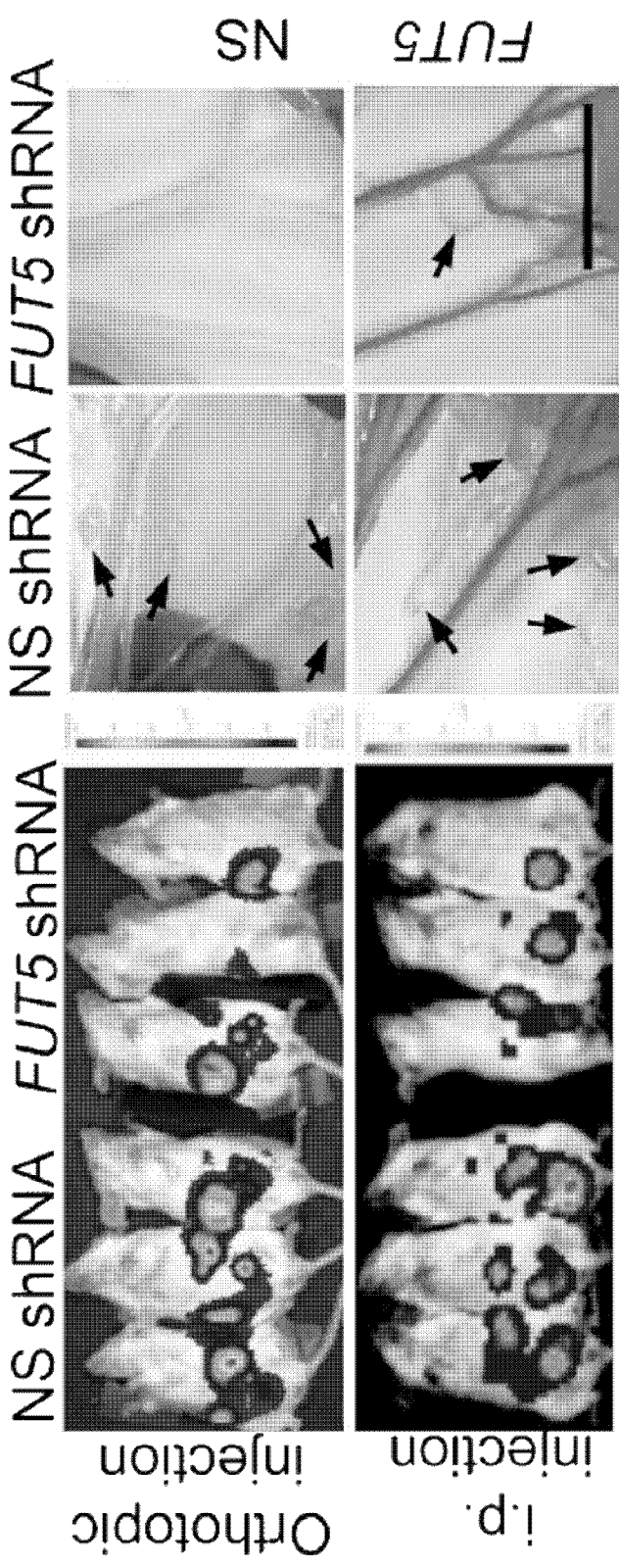
Figures 6E, 6F, 6G:
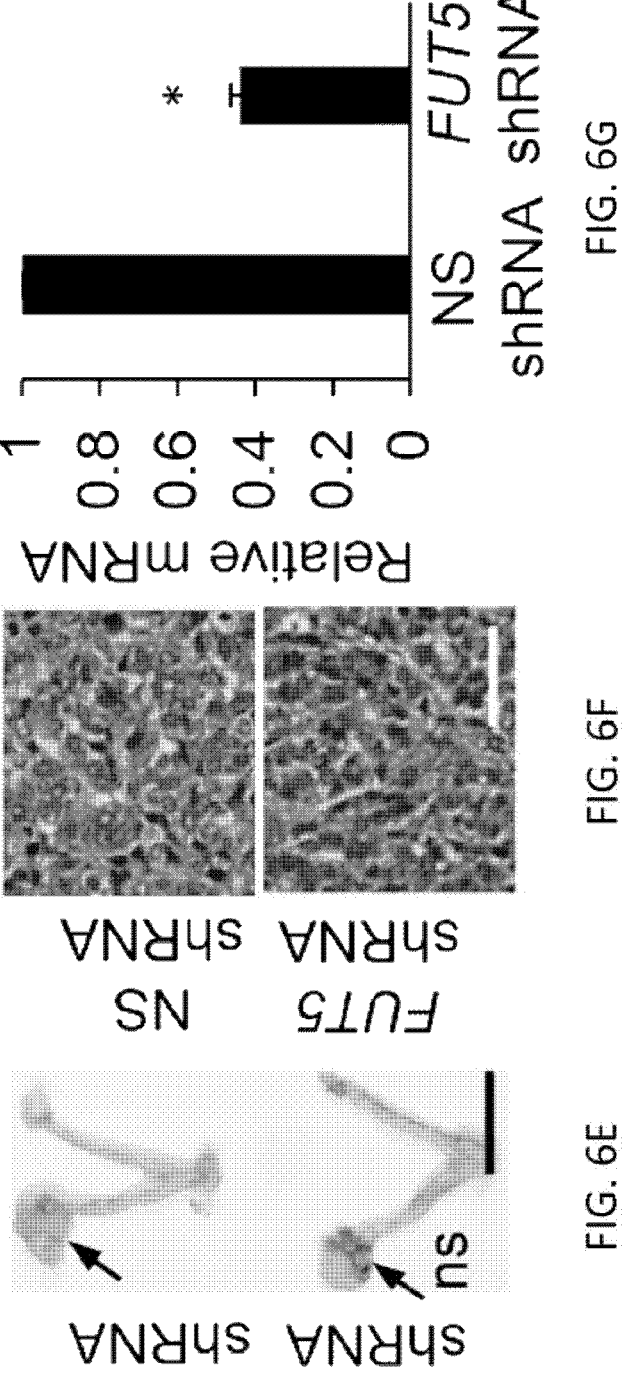
Figure 7:
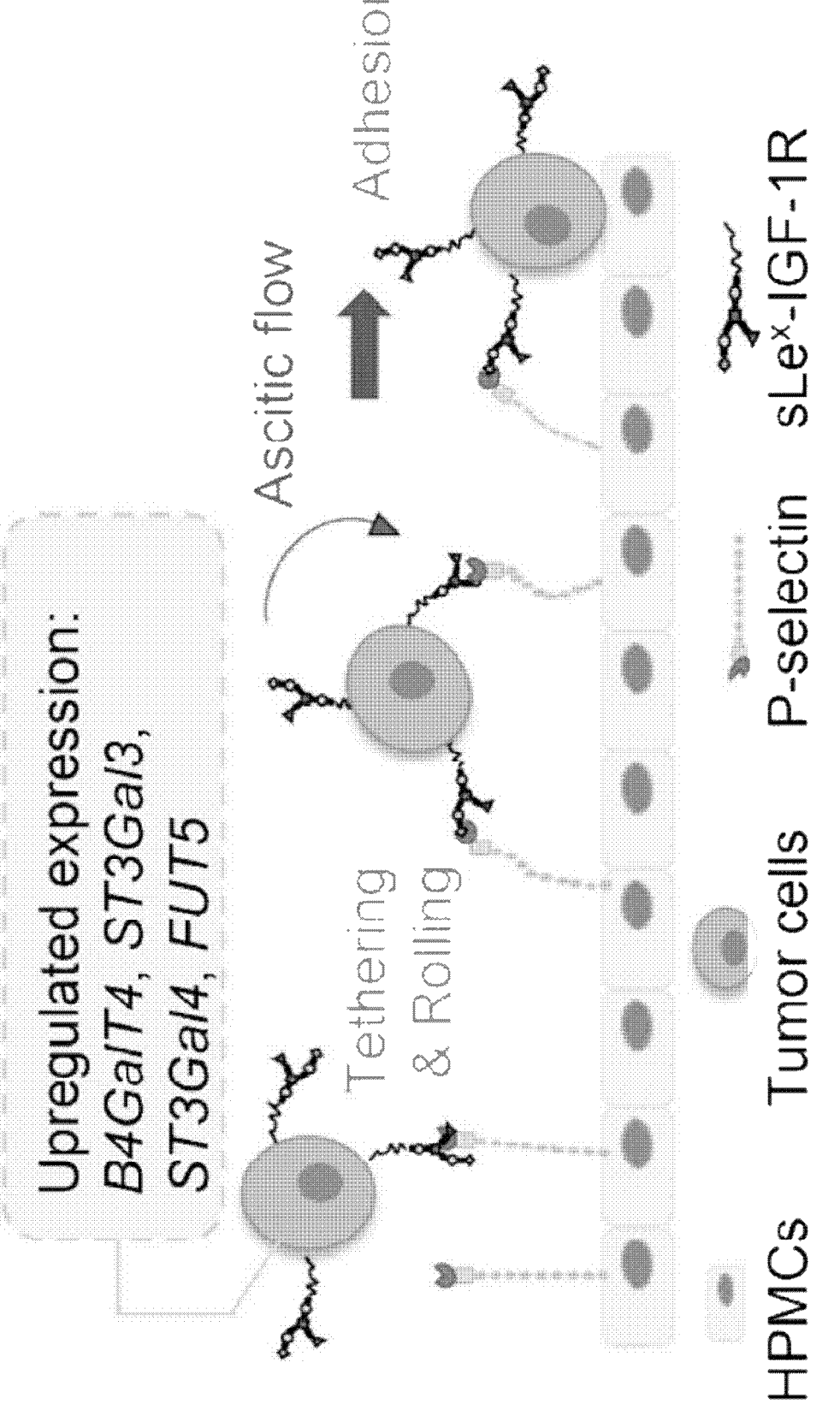
Figure 8A:
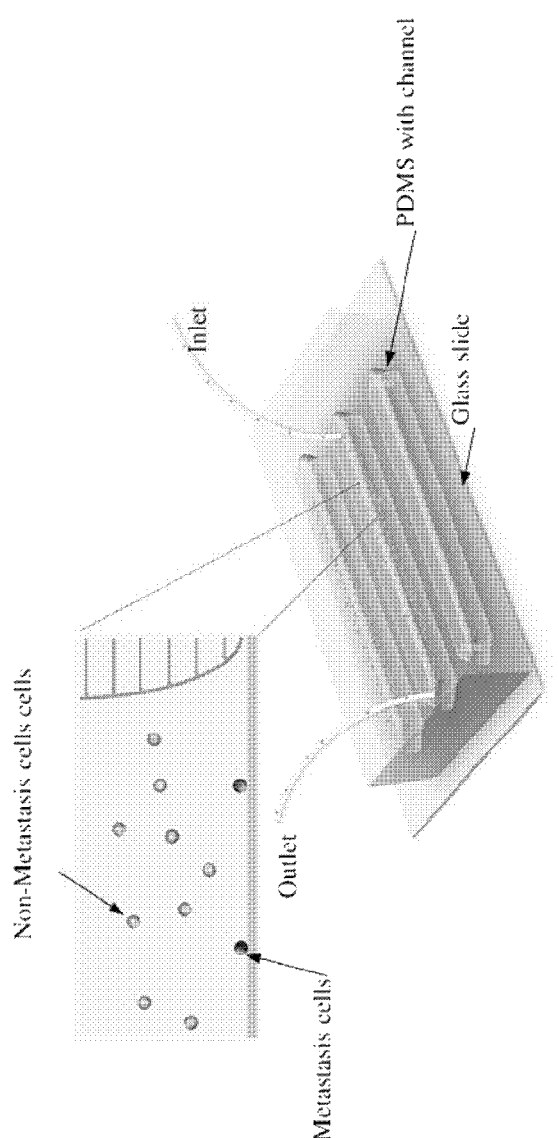
Figure 8B:
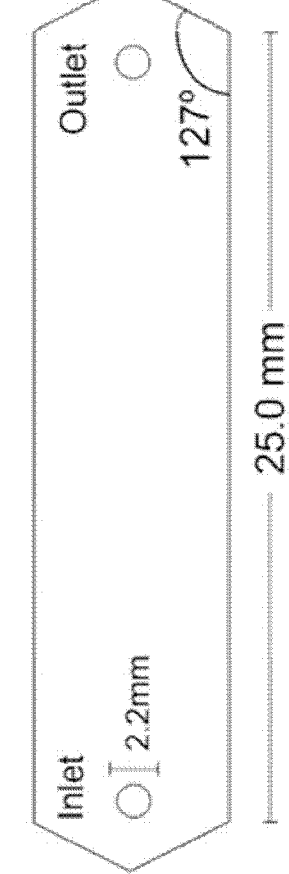
Figure 9C:
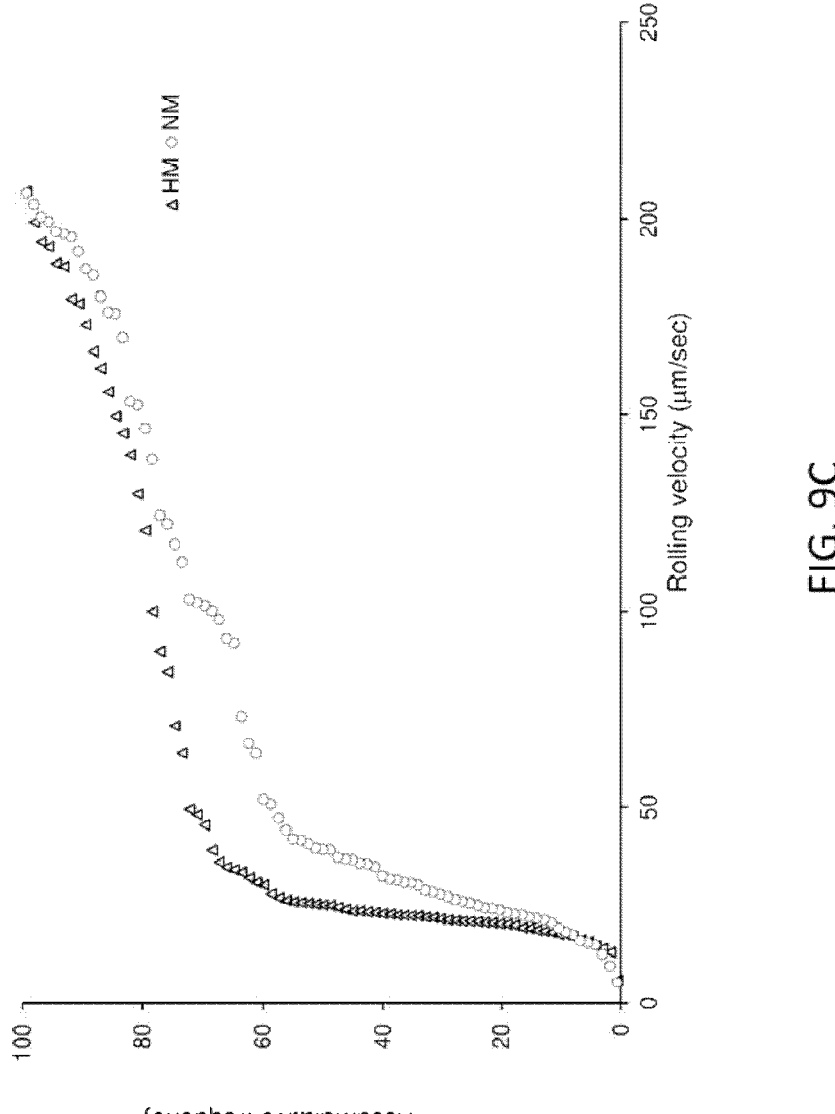
Figure 9E:
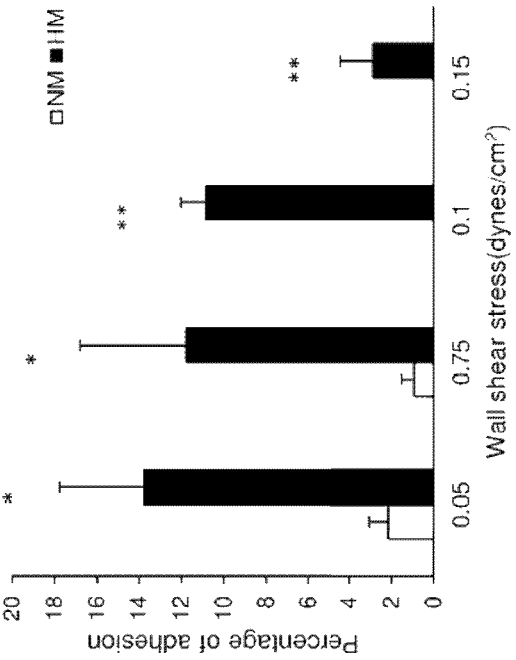
Figure 9D:
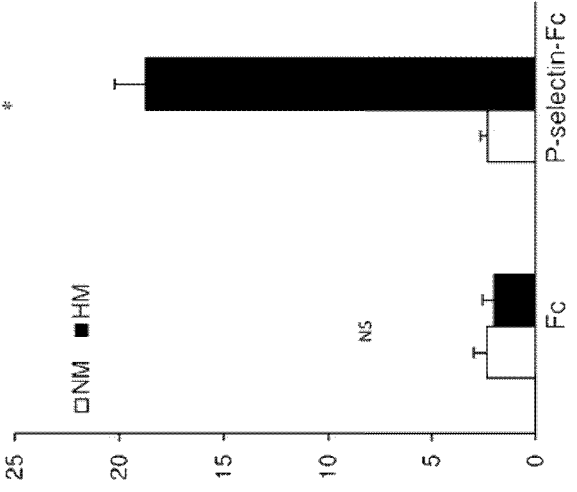
Figure 10B:
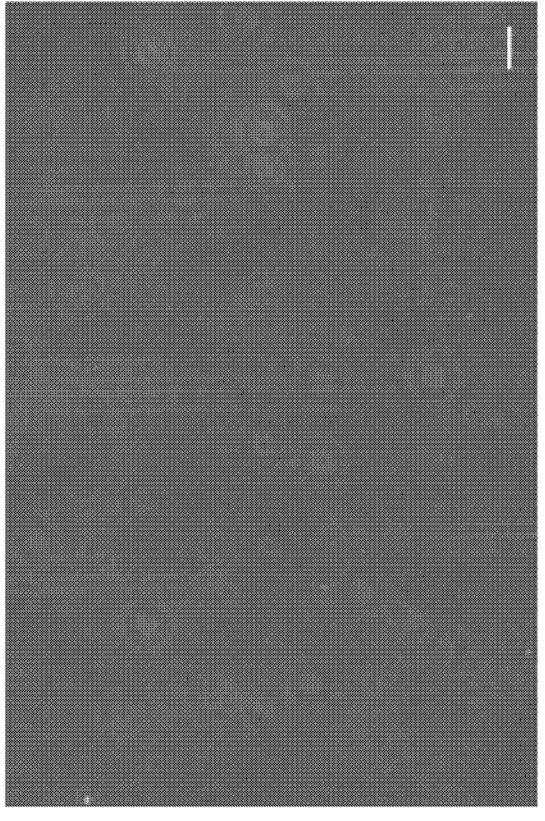
Figure 10A:
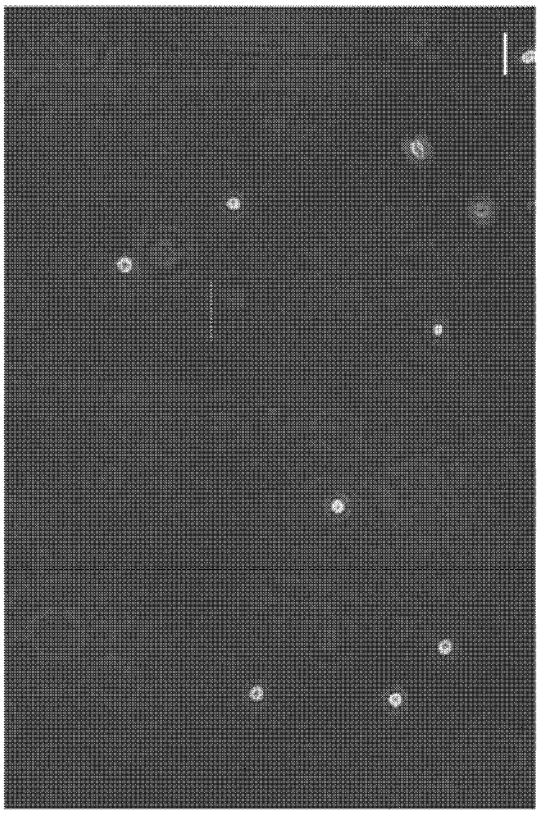

FUT5 is critical for ovarian tumor progression. To further define the molecular properties that contribute to P-selectin binding, we examined the expression profile of glycosyltransferases involved in sLe$^x$ synthesis (FIG. 6A) in M-CSCs and NM-CSCs. We found that several glycogenes, including B4GalT4, ST3Gal3, ST3Gal4 and FUT5, were significantly increased in M-CSCs when compared to NM-CSCs (FIG. 6A, FIG. 23A). Similar higher expression of these genes on patients' derived CSCs was also observed (FIG. 6A). The high mRNA expression of glycosyltransferases correlates with poorer progression-free survival in patients with advanced stage (FIGO stage III, IV) ovarian cancer (FIG. 23B). Among these genes, we are particularly interested in FUT5 which encodes a rate-limiting enzyme 1,3-fucosyltransferase catalyzing the addition of fucose residue for sLe$^x$ synthesis[22,23]. FUT5 knockdown abolished sLe$^x$ cell surface expression on M-CSCs (FIG. 6B) and largely reduced the adhesion of M-CSCs to HPMCs and P-selectin-Fc under shear stress (FIG. 6C). Moreover, mice inoculated with orthotopic or i.p. xenograft (FIG. 6D) of M-CSCs carrying FUT5 shRNA had significantly reduced metastatic implants and ascites formation in the peritoneal cavity when compared to mice injected with nonspecific shRNA M-CSCs (FIG. 16), with no apparent difference in primary tumor growth (FIG. 6E, F). Real-time PCR of tumor samples harvested from mice at the end of the study confirmed successful target gene knockdown of FUT5 (FIG. 6G).

8. DISCUSSION

Tumor microenvironment is one of the major factors controlling the metastatic progression; however, the detailed molecular mechanisms that operate the dissemination of ovarian cancer within the peritoneal cavity, particularly under ascitic shear stress, have not been explored. In this study, we have provided evidence that a sLe$^x$ bearing glycan on IGF-1R of ovarian M-CSCs interacts with P-selectin on HPMCs controls the tethering, rolling, and subsequent adhesion in peritoneal dissemination under shear stress.

Several lines of evidence suggest that CSCs may be a key player in the metastasis of ovarian cancer. First, ovarian CSCs are enriched in cells that can undergo epithelial-mesenchymal transition, a key process in metastasis[24]. Second, CSCs have higher tumorigenicity[25]. Third, ovarian cancer cells possess a stem-like gene signature correlates with poor progression-free and overall survival in cancer patients[26]. Fourth, the existence of these CSCs at an early stage of ovarian cancer may well explain the clinical observation of early metastasis[2]. In recent years, several studies in various cancer types, including breast and colorectal cancer, showed only a subpopulation of CSCs are able to metastasize[27-29]. In this report, we showed that the highly metastatic subpopulation CSCs in ovarian cancer ascites; and more importantly, we provided a detailed molecular understanding on their metastatic ability through a direct interaction with the peritoneal microenvironment which not been studied in previous metastatic CSC models.

Very little is known about the selectin ligands on ovarian carcinoma cells[30]. Our present work has uncovered a sLe$^x$-bearing P-selectin ligand in ovarian cancer cells, which is distinct from those previously defined P-selectin ligands, in particular the well-known ligand PSGL-1 which bears tyrosine sulfation. Much evidence hinted the casual relationship between sLe$^x$ and ovarian cancer metastasis. For example, antibodies against sLe$^x$ epitope have been previously shown to react with human ovarian cancer cells[31]. Glycosyltransferases which catalyze the synthesis of sLe$^x$ are significantly elevated in ovarian carcinoma tissues and cell lines[32,33]. High sLe$^x$ expression is associated with poor survival of patients with ovarian cancer[34]. The sLe$^x$-bearing glycan present on M-CSCs binds P-selectin in a rigid fucosylation-dependent and relatively loose sialyation-dependent manner, instead of a simple sLe$^x$ structure that relies equally on fucose and sialic acid moieties[35]. Such biochemistry is of biological significance, as fucosylation has been shown with increased affinity and bind selectin more efficiently[36-38]. Whereas sulfation is a common feature of P-selectin ligands[39,40], our results suggest that the sLe$^x$-bearing glycan on M-CSCs does not require sulfation for its binding to P-selectin. There is evidence that sulfated moieties of P-selectin ligands tend to be more resilient to stress for binding under high shear conditions[41].

While consistent with a direct role for P-selectin in mediating the tumor-mesothelial interaction, our findings also appear to differ somewhat from those of a recent work to show the sLe$^x$-bearing P-selectin ligand[10]; however, the use of cells with different genetic backgrounds in this recent work may explain the difference. While CD24 expression is higher in some cell lines, the cell adhesion via P-selectin seems less, suggesting that there is other sLe$^x$-containing ligand(s) of P-selectin. Using carefully controlled conditions and in comparison with a non-metastatic counterpart, while we have also shown CD24 expression in M-CSCs and NM-CSCs, there was no differential expression on CD24, unlike IGF-1R, in M-CSCs and NM-CSCs, suggesting the importance of IGF-1R in mediating the adhesion of M-CSCs. Moreover, our findings are in agreement with a large literature that links IGF-1R with tumor progression.

The sLe$^x$-bearing P-selectin ligand is presented on IGF-1R, which is frequently overexpressed in ovarian cancer and other peritoneal metastasis models and confers a poor clinical prognosis[42,43]. Recently, sLe$^x$ has been identified to be decorated on various unexpected proteins, and functions of the sLe$^x$ are largely unknown[44]. IGF-1R, which to the best of our knowledge has not been shown previously to possess sLe$^x$. Although incompletely understood, there is growing appreciation for a role of sLe$^x$ in modulating protein activity. In gastric cancer cells, increased sLe$^x$ of c-Met was associated with increased dimerization and phosphorylation, which resulted in increased c-Met-mediated signaling associated with tumor invasiveness[45]. While we surmise that IGF-1R is functionally relevant for ovarian cancer progression and metastasis, our work suggests that blocking the sLe$^x$ mediating IGF-1R will be required to provide a promising effect.

Additionally, our findings underscore a critical role for FUT5 during the development and maintenance of the metastasis. Higher incidence of sLe$^x$ in M-CSCs coincided with higher expression of glycosyltransferases. Ovarian cancer patients with FUT5 overexpressing tumors correlates with poorer survival compared to patients with low or no FUT5 expressing tumors. Importantly, blocking FUT5 expression in M-CSCs serves as an effective strategy for the treatment of peritoneal dissemination. Most of the glycosyltransferases genes involved in sLe$^x$ synthesis are constitutively expressed to produce sLe$^x$ direct precursor, while, FUTs encoding at 1-3 fucosyltransferases catalyzing the last and rate-limiting step of sLe$^x$ synthesis by adding fucose to the precursor are normally switched off[22,23]. Moreover, peritoneal colonization of gastric cancer cells was reported to be suppressed by the downregulation of FUT5[46]. These data suggest that it is the context in which the glycan is expressed contributes to organotropism.

In summary, this study provides evidence showing P-selectin as a key molecule on HPMCs and IGF-1R carrying sLe$^x$ on HM-CSCs as a ligand in mediating peritoneal dissemination under ascitic flow-induced shear stress (FIG.

7). This research is not only relevant to ovarian cancer, but also applicable to other tumor types, such as breast and colon cancers, in which peritoneal metastasis is an important pathological process, indicating that sLe$^x$-P-selectin could become promising therapeutic targets.

The following numbered items provide further nonlimiting details on the embodiment described herein.

1. A method for detecting peritoneal metastatic cells in a sample obtained from a subject comprising: (a) contacting peritoneal metastatic cells and peritoneal non-metastatic cells in the sample with P-selectin; and (b) detecting selective binding of the peritoneal metastatic cells to the P-selectin.

2. The method of item 1 wherein the peritoneal metastatic cells are from gastrointestinal cancer or gynecological cancer.

3. The method of any of the preceding items wherein the gynecological cancer is ovarian cancer, uterine cancer, cervical cancer or vaginal cancer.

4. The method of any of the preceding items wherein the gastrointestinal cancer is liver cancer, colon cancer, prostate cancer, bladder cancer and rectal cancer.

5. The method of any of the preceding items further comprising a step of isolating the peritoneal metastatic cells.

6. The method of any of the preceding items further comprising a step of culturing the peritoneal metastatic cells.

7. The method of any of the preceding items further comprises characterizing the peritoneal metastatic cells.

8. A method for detecting peritoneal metastatic cells in a sample obtained from a subject comprising: (a) introducing the sample into an inlet of a microfluidic device wherein the microfluidic device comprises a channel that is coated with P-selectin; (b) flowing the sample at an effective wall shear stresses; (c) separating the peritoneal metastatic cells from non-peritoneal metastatic cells, wherein the peritoneal metastatic cells binds to P-selectin; and (d) detecting the peritoneal metastatic cells.

9. The method of any of the preceding items wherein the effective wall shear stresses is about 0.1 dyne/cm$^2$.

10. The method of any of the preceding items wherein the device is a microfluidic chip.

11. The method of any of the preceding items wherein the peritoneal metastatic cells are detected by a label.

12. The method of any of the preceding items wherein the peritoneal metastatic cells are from gastrointestinal cancer or gynecological cancer.

13. The method of any of the preceding items wherein the gynecological cancer is ovarian cancer, uterine cancer, cervical cancer or vaginal cancer.

14. The method of any of the preceding items wherein the gastrointestinal cancer is liver cancer, colon cancer, prostate cancer, bladder cancer and rectal cancer.

15. The method of any of the preceding items further comprising a step of isolating the peritoneal metastatic cells.

16. The method of any of the preceding items further comprising a step of culturing the peritoneal metastatic cells.

17. A method for separating peritoneal metastatic cells in a sample obtained from a subject comprising: (a) introducing the sample into an inlet of a microfluidic device wherein the microfluidic device comprises a channel that is coated with a detectable P-selectin; (b) separating the peritoneal metastatic cells from non-peritoneal metastatic cells in the sample by selective binding of the peritoneal metastatic cells to the detectable P-selectin.

18. The method of any of the preceding items wherein the effective wall shear stresses is about 0.1 dyne/cm2.

19. The method of any of the preceding items wherein the device is a microfluidic chip.

20. The method of any of the preceding items wherein the peritoneal metastatic cells are detected by a label.

21. The device of any of the preceding items wherein the peritoneal metastatic cells are from gastrointestinal cancer or gynecological cancer.

22. The device of any of the preceding items wherein the gynecological cancer is ovarian cancer, uterine cancer, cervical cancer or vaginal cancer.

23. The device of any of the preceding items wherein the gastrointestinal cancer is liver cancer, bladder cancer and rectal cancer.

24. The method of any of the preceding items further comprising a step of isolating the peritoneal metastatic cells.

25. The method of any of the preceding items further comprising a step of culturing the peritoneal metastatic cells.

26. A method of screening anti-metastatic drugs comprising: (a) contacting metastatic cells with a test agent; (b) selective binding of the treated metastatic cells to P-selectin; and (c) detecting metastatic cells contacted with the test agent that does not selectively bind to the P-selectin, wherein metastatic cells that does not bind to the P-selectin indicates that the cells were contacted with a test agent that has anti-metastatic property.

27. The method of any of the preceding items wherein the peritoneal metastatic cells are detected by a label.

28. The device of any of the preceding items wherein the peritoneal metastatic cells are from gastrointestinal cancer or gynecological cancer.

29. The device of any of the preceding items wherein the gynecological cancer is ovarian cancer, uterine cancer, cervical cancer or vaginal cancer.

30. The device of any of the preceding items wherein the gastrointestinal cancer is liver cancer, bladder cancer and rectal cancer.

31. The method of any of the preceding items further comprising a step of isolating the peritoneal metastatic cells.

32. The method of any of the preceding items further comprising a step of culturing the peritoneal metastatic cells.

33. A kit for detecting peritoneal metastatic cells in a sample obtained from a subject, said kit comprising a microfluidic chip and a detectable P-selectin.

REFERENCES

1. Siegel, R. L., Miller, K. D. & Jemal, A. Cancer Statistics, 2019. CA: Cancer J Clin 69, 7-34(2019).

2. Lengyel, E. Ovarian cancer development and metastasis. Am J Pathol 177, 1053-1064 (2010).

3. Massague, J. & Obenauf, A. C. Metastatic colonization by circulating tumour cells. Nature 529, 298-306 (2016).

4. Kipps, E., Tan, D. S. & Kaye, S. B. Meeting the challenge of ascites in ovarian cancer: new avenues for therapy and research. Nat Rev Cancer 13, 273-282 (2013).

5. McEver, R. P. & Zhu, C. Rolling cell adhesion. Ann Rev Cell Dev Biol 26, 363-396 (2010).

6. Laubli, H. & Borsig, L. Selectins promote tumor metastasis. Semin Cancer Biol 20, 169-177(2010).

7. Friederichs, J. et al. The CD24/P-selectin binding pathway initiates lung arrest of human A125 adenocarcinoma cells. Cancer Res 60, 6714-6722 (2000).

8. Dimitroff, C. J., Lechpammer, M., Long-Woodward, D. & Kutok, J. L. Rolling human bone-metastatic prostate tumor cells on human bone marrow endothelium under shear flow is mediated by E-selectin. Cancer Res 64, 5261-5269 (2004).

9. Gebauer, F. et al. Selectin binding is essential for peritoenal carcinomatosis in a xenograft model of human pancreatic adenocarcinoma in pfp−/rag2− mice. Gut 62, 741-750 (2013).

10. Carroll, M. J. et al. Alternatively-activated macrophages upregulate mesothelial expression of P-selectin to enhance adhesion of ovarian cancer cells. Cancer Res 78, 3560-3573 (2018).

11. Nagy, J. A., Herzberg, K. T., Dvorak, J. M. & Dvorak, H. F. Pathogenesis of malignant ascites formation: initiating events that lead to fluid accumulation. Cancer Res 53, 2631-2643 (1993).

12. Chau, W. K., Ip, C. K., Mak, A. S., Lai, H. C. & Wong, A. S. c-Kit mediates chemoresistance and tumor-initiating capacity of ovarian cancer cells through activation of Wnt/beta-catenin-ATP-binding cassette G2 signaling. Oncogene 32, 2767-2781 (2013).

13. Ip, C. K. et al. Sternness and chemoresistance in epithelial ovarian carcinoma cells under shear stress. Sci Rep 6, 26788 (2016).

14. Nagy, J. A. et al. Pathogenesis of ascites tumor growth: vascular permeability factor, vascular hyperpermeability, and ascites fluid accumulation. Cancer Res 55, 360-368 (1995).

15. Lawrence, M. B., Kansas, G. S., Kunkel, E. J. & Ley, K. Threshold levels of fluid shear promote leukocyte adhesion through selectins (CD62L,P,E). J Cell Biol 136, 717-727 (1997).

16. Yanez-Mo, M. et al. Peritoneal dialysis and epithelial-to-mesenchymal transition of mesothelial cells. N Engl J Med 348, 403-413 (2003).

17. Varki, A. Selectin ligands. Proc Natl Acad Sci USA 91, 7390-7397 (1994).

18. Steele, I. A. et al. Induction of FGF receptor 2-IIIb expression and response to its ligands in epithelial ovarian cancer. Oncogene 20, 5878-5887 (2001).

19. Brokaw, J. et al. IGF-I in epithelial ovarian cancer and its role in disease progression. Growth Factors 25, 346-354 (2007).

20. Sawada, K. et al. c-Met overexpression is a prognostic factor in ovarian cancer and an effective target for inhibition of peritoneal dissemination and invasion. Cancer Res 67, 1670-1679 (2007).

21. Ellerbroek, S. M. et al. Phosphatidylinositol 3-kinase activity in epidermal growth factor-stimulated matrix metalloproteinase-9 production and cell surface association. Cancer Res 61, 1855-1861 (2001).

22. de Vries, T., Knegtel, R M., Holmes, E. H. & Macher, B. A. Fucosyltransferases: structure/function studies. Glycobiology 11, 119R-128R (2001).

23. Lofling, J. & Holgersson, J. Core saccharide dependence of sialyl Lewis X biosynthesis. Glycoconj J 26, 33-40 (2009).

24. Yin, G. et al. Constitutive proteasomal degradation of TWIST-1 in epithelial-ovarian cancer stem cells impacts differentiation and metastatic potential. Oncogene 32, 39-49 (2013).

25. Zhang, S. et al. Identification and characterization of ovarian cancer-initiating cells from primary human tumors. Cancer Res 68, 4311-4320 (2008).

26. Vathipadiekal, V. et al. Identification of a potential ovarian cancer stem cell gene expression profile from advanced stage papillary serous ovarian cancer. PloS One 7, e29079 (2012).

27. Baccelli, I. et al. Identification of a population of blood circulating tumor cells from breast cancer patients that initiates metastasis in a xenograft assay. Nat Biotechnol 31, 539-544 (2013).

28. Dieter, S. M. et al. Distinct types of tumor-initiating cells form human colon cancer tumors and metastases. Cell Stem Cell 9, 357-365 (2011).

29. Pang, R et al. A subpopulation of CD26+ cancer stem cells with metastatic capacity in human colorectal cancer. Cell Stem Cell 6, 603-615 (2010).

30. Elmasri, V. M., Casagrande, G., Hoskins, E., Kimm, D. & Kohn, E. C. Cell adhesion in ovarian cancer. Cancer Treat Res 149, 297-318 (2009).

31. Inoue, M., Fujita, M., Nakazawa, A, Ogawa, H. & Tanizawa, O. Sialyl-Tn, sialyl-Lewis Xi, CA 19-9, CA 125, carcinoembryonic antigen, and tissue polypeptide antigen in differentiating ovarian cancer from benign tumors. Obstet Gynecol 79, 434-440(1992).

32. Escrevente, C. et al. Different expression levels of alpha3/4 fucosyltransferases and Lewis determinants in ovarian carcinoma tissues and cell lines. Int J Oncol 29, 557-566 (2006).

33. Wang, P. H. et al. Altered mRNA expressions of sialyltransferases in ovarian cancers. Gynecol Oncol 99, 631-639 (2005).

34. Saldova, R et al. Ovarian cancer is associated with changes in glycosylation in both acute-phase proteins and IgG. Glycobiology 17, 1344-1356 (2007).

35. Zhou, Q. et al. The selectin GMP-140 binds to sialylated, fucosylated lactosaminoglycans on both myeloid and nonmyeloid cells. J Cell Biol 115, 557-564 (1991).

36. Toppila, S. et al. Enzymatic synthesis of alpha3'sialylated and multiply alpha3fucosylated biantennary polylactosamines. A bivalent [sialyl diLex]-saccharide inhibited lymphocyte-endothelium adhesion organ-selectively. Eur J Biochem 261, 208-215 (1999).

37. Phillips, M. L. et al. ELAM-1 mediates cell adhesion by recognition of a carbohydrate ligand, sialyl-Lex. Science 250, 1130-1132 (1990).

38. Listinsky, J. J., Siegal, G. P. & Listinsky, C. M. Alpha-L-fucose: a potentially critical molecule in pathologic processes including neoplasia. Am J Clin Pathol 110, 425-440 (1998).

39. Aruffo, A. et al. CD62/P-selectin recognition of myeloid and tumor cell sulfatides. Cell 67, 35-44 (1991).

40. Sako, D. et al. A sulfated peptide segment at the amino terminus of PSGL-1 is critical for P-selectin binding. Cell 83, 323-331 (1995).

41. Rodgers, S. D., Camphausen, R T. & Hammer, D. A. Tyrosine sulfation enhances but is not required for PSGL-1 rolling adhesion on P-selectin. Biophys J 81, 2001-2009 (2001).

42. Spentzos, D. et al. IGF axis gene expression patterns are prognostic of survival in epithelial ovarian cancer. Endocr Relat Cancer 14, 781-790 (2007).

43. Takahari, D. et al. Relationships of insulin-like growth factor-1 receptor and epidermal growth factor receptor expression to clinical outcomes in patients with colorectal cancer. Oncology 76, 42-48 (2009).

44. Varki A, Kannagi R, Toole B P. Glycosylation Changes in Cancer. In: Varki A, Cummings R D, Esko J D, et al., editors. Essentials of Glycobiology. 2nd edition. Cold Spring Harbor (N.Y.): Cold Spring Harbor Laboratory Press; 2009. Chapter 44.

45. Gomes, C. et al. Expression of ST3GAL4 leads to SLe(x) expression and induces c-Met activation and an invasive phenotype in gastric carcinoma cells. PloS One 8, e66737 (2013).

46. Padro, M., Cobler, L., Garrido, M. & de Bolos, C. Down-regulation of FUT3 and FUT5 by shRNA alters Lewis antigens expression and reduces the adhesion capacities of gastric cancer cells. Biochim Biophys Acta 1810, 1141-1149 (2011).

47. Yung, S., Li, F. K. & Chan, T. M. Peritoneal mesothelial cell culture and biology. Perit Dial Int 26, 162-173 (2006).

48. Gokturk, H. S. et al. The role of ascitic fluid viscosity in the differential diagnosis of ascites. Can J Gastroenterol 24, 255-259 (2010).

49. Chen, S., Alon, R., Fuhlbrigge, R C. & Springer, T. A. Rolling and transient tethering of leukocytes on antibodies reveal specializations of selectins. Proc Natl Acad Sci USA 94, 3172-3177 (1997).

50. SUPP REF: Gyorffy, B., Lanczky, A. & Szallasi, Z. Implementing an online tool for genome-wide validation of survival-associated biomarkers in ovarian-cancer using microarray data from 1287 patients. Endocr Relat Cancer 19, 197-208 (2012).

The foregoing description of the specific embodiments will so fully reveal the general nature of the disclosure that others can, by applying knowledge within the skill of the relevant art(s) (including the contents of the documents cited and incorporated by reference herein), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure. Thus, the present disclosure should not be limited by any of the above-described exemplary embodiments, but should be defined only in accordance with the following claims and their equivalents.

The invention claimed is:

1. A method for detecting peritoneal metastatic cells in a sample obtained from a subject comprising: (a) flowing the sample using a microfluidic device at an effective wall shear stress, wherein a channel bottom of the microfluidic device is coated with P-selectin, wherein the effective wall shear stress is about 0.1-0.15 dyne/cm$^2$, and contacting peritoneal metastatic cells and peritoneal non-metastatic cells in the sample with P-selectin such that the peritoneal non-metastatic cells are all washed away, and the peritoneal metastatic cells selectively bind to the P-selectin; and (b) detecting selective binding of the peritoneal metastatic cells to the P-selectin.

2. The method of claim 1, wherein the peritoneal metastatic cells are from gastrointestinal cancer or gynecological cancer.

3. The method of claim 2, wherein the gynecological cancer is ovarian cancer, uterine cancer, cervical cancer or vaginal cancer.

4. The method of claim 1, wherein the gastrointestinal cancer is liver cancer, colon cancer, prostate cancer, bladder cancer and rectal cancer.

5. The method of claim 1, further comprising a step of isolating the peritoneal metastatic cells.

6. The method of claim 1, further comprising a step of culturing the peritoneal metastatic cells.

7. The method of claim 1, further comprising a step of characterizing the peritoneal metastatic cells.

8. The method of claim 1, wherein the effective wall shear stress is about 0.1 dyne/cm$^2$.

9. The method of claim 1. wherein the microfluidic device is a microfluidic chip.

10. The method of claim 1, wherein the peritoneal metastatic cells are detected by a label.

11. The method of claim 1, wherein the P-selectin is a P-selectin-Fc recombinant protein.

12. The method of claim 1, wherein the channel bottom is prepared by incubating with 1 μg mL$^{-1}$ selectin-Fc recombinant protein in PBS at 4° C. overnight.

13. The method of claim 12, further comprising a step of EDTA detachment, wherein the step of EDTA detachment comprises introducing the sample in a binding buffer into the channel bottom coated with P-selectin recombinant protein at a shear stress of 0.1 dynes/cm$^2$ for 1 min followed by perfusion with PBS for 1 min at the shear stress of 0.1 dynes/cm$^2$.

\* \* \* \* \*